US011518807B2

(12) United States Patent
Davis et al.

(10) Patent No.: US 11,518,807 B2
(45) Date of Patent: *Dec. 6, 2022

(54) HEAVY CHAIN CONSTANT REGIONS WITH REDUCED BINDING TO FC GAMMA RECEPTORS

(71) Applicant: Regeneron Pharmaceuticals, Inc., Tarrytown, NY (US)

(72) Inventors: Samuel Davis, New York, NY (US); Eric Smith, New York, NY (US); Tong Zhang, Fort Lee, NJ (US); Supriya Patel, Mamaroneck, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 70 days.

This patent is subject to a terminal disclaimer.

(21) Appl. No.: 16/720,623

(22) Filed: Dec. 19, 2019

(65) Prior Publication Data

US 2020/0109203 A1 Apr. 9, 2020

Related U.S. Application Data

(63) Continuation of application No. 15/562,881, filed as application No. PCT/US2016/025051 on Mar. 30, 2016, now Pat. No. 10,556,952.

(60) Provisional application No. 62/140,350, filed on Mar. 30, 2015.

(51) Int. Cl.
*C07K 16/28* (2006.01)

(52) U.S. Cl.
CPC ...... *C07K 16/2809* (2013.01); *C07K 16/2803* (2013.01); *C07K 16/2887* (2013.01); *C07K 2317/24* (2013.01); *C07K 2317/31* (2013.01); *C07K 2317/526* (2013.01); *C07K 2317/53* (2013.01); *C07K 2317/71* (2013.01); *C07K 2317/732* (2013.01); *C07K 2317/90* (2013.01)

(58) Field of Classification Search
None
See application file for complete search history.

(56) References Cited

U.S. PATENT DOCUMENTS

| 5,624,821 | A  | 4/1997  | Winter et al. |
| 5,648,260 | A  | 7/1997  | Winter et al. |
| 6,180,377 | B1 | 1/2001  | Morgan et al. |
| 7,396,917 | B2 | 7/2008  | Bowdish et al. |
| 7,563,441 | B2 | 7/2009  | Graus et al. |
| 7,597,889 | B1 | 10/2009 | Armour et al. |
| 7,608,260 | B2 | 10/2009 | Schenerman et al. |
| 7,700,097 | B2 | 4/2010  | Braslawsky et al. |
| 7,700,099 | B2 | 4/2010  | Strohl |
| 7,728,114 | B2 | 6/2010  | Mach et al. |
| 7,820,166 | B2 | 10/2010 | Lanzavecchia et al. |
| 7,824,684 | B2 | 11/2010 | Graus et al. |
| 7,867,491 | B2 | 1/2011  | Yang et al. |
| 7,960,512 | B2 | 6/2011  | Stavenhagen et al. |
| 8,075,884 | B2 | 12/2011 | Bowdish et al. |
| 8,084,026 | B2 | 12/2011 | Glaser et al. |
| 8,153,583 | B2 | 4/2012  | Carton et al. |
| 8,236,314 | B2 | 8/2012  | Kai et al. |
| 8,268,972 | B2 | 9/2012  | Whitfeld et al. |
| 8,383,109 | B2 | 2/2013  | Lazar et al. |
| 8,409,568 | B2 | 4/2013  | Gao et al. |
| 8,961,967 | B2 | 2/2015  | Strohl et al. |
| 9,359,437 | B2 | 6/2016  | Davis et al. |
| 10,106,610 | B2 | 10/2018 | Davis et al. |
| 10,179,819 | B2 | 1/2019  | Kirshner et al. |
| 10,556,952 | B2 | 2/2020  | Davis et al. |
| 10,738,130 | B2 | 8/2020  | Haber et al. |
| 10,772,972 | B2 | 9/2020  | Rudge et al. |
| 10,988,537 | B2 | 4/2021  | Davis et al. |
| 2004/0171123 | A1* | 9/2004 | Rosen ............ A61P 21/04 435/325 |
| 2005/0226876 | A1 | 10/2005 | Graus et al. |
| 2005/0244403 | A1 | 11/2005 | Lazar et al. |

(Continued)

FOREIGN PATENT DOCUMENTS

| EP | 0327378 B1 | 12/1996 |
| EP | 2447372 A2 | 5/2012 |

(Continued)

OTHER PUBLICATIONS

"IgG-Fc Engineering for Therapeutic Use," InvivoGen Insight, 1 page, (2006). [Author Unknown] [Retrieved from the Internet Apr. 4, 2014: <URL: http://www.invivogen.comiclocs/Insight200605 pdf>].

"IgG-Fe engineering for therapeutic use," Invivogen, 2 pages, (2007). [Author Unknown] [Retrieved from the Internet Jan. 12, 2011: <URL: http://www.invivogen.com/ressource.php?ID=22>].

Aalberse et al., "IgG4 breaking the rules," Immunology, 105(1):9-19, (2002).

Advani et al., "New immune strategies for the treatment of acute lymphoblastic leukemia: antibodies and chimeric antigen receptors," Hematology, vol. 2013 (No. 1): (Dec. 1, 2013).

(Continued)

*Primary Examiner* — Nelson B Moseley, II
(74) *Attorney, Agent, or Firm* — Schwabe, Williamson & Wyatt PC; Todd Samelman

(57) ABSTRACT

The invention provides antibody heavy chain constant regions with a hinge region modified to reduce binding to Fcγ receptors. The modification occurs within positions 233-236 by replacement of natural residues by glycine(s) and/or deletion(s). Such modifications can reduce binding of an antibody bearing such a constant region to Fcγ receptors to background levels. The constant regions can be incorporated into any format of antibody or Fc fusion protein. Such antibodies or fusion proteins can be used in methods of treatment, particularly those in which the mechanisms of action of the antibody or Fc fusion protein is not primarily or at all dependent on effector functions, as is the case when an antibody inhibits a receptor-ligand interaction or agonizes a receptor.

40 Claims, 18 Drawing Sheets

Specification includes a Sequence Listing.

(56) References Cited

U.S. PATENT DOCUMENTS

| | | |
|---|---|---|
| 2005/0037000 A1 | 12/2005 | Stavenhagen et al. |
| 2006/0134709 A1* | 6/2006 | Stavenhagen .......... C07K 16/30 530/388.3 |
| 2007/0009523 A1 | 1/2007 | Presta |
| 2007/0041972 A1 | 2/2007 | Rother et al. |
| 2009/0117133 A1 | 5/2009 | Arnason et al. |
| 2009/0162901 A1 | 6/2009 | Chen et al. |
| 2009/0252729 A1 | 10/2009 | Farrington et al. |
| 2010/0105874 A1 | 4/2010 | Schuurman et al. |
| 2010/0166749 A1 | 7/2010 | Presta |
| 2010/0267934 A1 | 10/2010 | Winkel et al. |
| 2010/0298542 A1 | 11/2010 | Igawa et al. |
| 2010/0325744 A1 | 12/2010 | Schuurman et al. |
| 2010/0331527 A1 | 12/2010 | Davis et al. |
| 2011/0077383 A1 | 3/2011 | Dall'Acqua et al. |
| 2011/0212087 A1 | 9/2011 | Strohl et al. |
| 2011/0245473 A1 | 10/2011 | Igawa et al. |
| 2011/0263830 A1 | 10/2011 | Goetsch et al. |
| 2011/0293607 A1 | 12/2011 | Labrijn et al. |
| 2012/0065379 A1 | 3/2012 | Igawa et al. |
| 2012/0071634 A1 | 3/2012 | Igawa et al. |
| 2012/0100140 A1 | 4/2012 | Reyes et al. |
| 2012/0189643 A1 | 7/2012 | Carton et al. |
| 2012/0225058 A1 | 9/2012 | Lazar et al. |
| 2012/0237515 A1 | 9/2012 | Bell et al. |
| 2012/0238729 A1 | 9/2012 | Kuramochi et al. |
| 2012/0251531 A1 | 10/2012 | Baehner et al. |
| 2012/0276096 A1 | 11/2012 | Yang et al. |
| 2012/0276097 A1 | 11/2012 | Yang et al. |
| 2013/0011386 A1 | 1/2013 | Brerski et al. |
| 2013/0101581 A1 | 4/2013 | Kuramochi et al. |
| 2013/0108623 A1 | 5/2013 | D'Angelo et al. |
| 2013/0129723 A1 | 5/2013 | Blankenship et al. |
| 2013/0251707 A1 | 9/2013 | Kontermann et al. |
| 2014/0088295 A1 | 3/2014 | Smith et al. |
| 2014/0112914 A1 | 4/2014 | Nezu et al. |
| 2014/0120581 A1 | 5/2014 | Niwa et al. |
| 2015/0166661 A1 | 6/2015 | Chen et al. |
| 2015/0203579 A1 | 7/2015 | Papadopoulos et al. |
| 2016/0130347 A1 | 5/2016 | Bruenker et al. |
| 2016/0168247 A1 | 6/2016 | Van Den Brink et al. |
| 2016/0347839 A1 | 12/2016 | Davis et al. |
| 2017/0008951 A1 | 1/2017 | Block et al. |
| 2017/0051074 A1 | 2/2017 | Kirshner et al. |
| 2018/0104357 A1 | 4/2018 | Rudge et al. |
| 2018/0112001 A1 | 4/2018 | Haber et al. |
| 2018/0118848 A1 | 5/2018 | Haber et al. |
| 2018/0303953 A1 | 10/2018 | Van Berkel et al. |
| 2019/0127480 A1 | 5/2019 | Kirshner et al. |
| 2019/0389966 A1 | 12/2019 | Crawford |
| 2020/0317810 A1 | 10/2020 | Haber et al. |

FOREIGN PATENT DOCUMENTS

| | | |
|---|---|---|
| EP | 2918604 A1 | 9/2015 |
| WO | 97/028267 A1 | 8/1997 |
| WO | 99/043713 A1 | 9/1999 |
| WO | 99/058572 A1 | 11/1999 |
| WO | 00/042072 A2 | 7/2000 |
| WO | 03/026490 A2 | 4/2003 |
| WO | 2008/147143 A2 | 12/2008 |
| WO | 10/054212 A1 | 5/2010 |
| WO | 10/063785 A2 | 6/2010 |
| WO | 10/085682 A2 | 7/2010 |
| WO | 11/137362 A1 | 11/2011 |
| WO | 12/022982 A2 | 2/2012 |
| WO | 12/035141 A1 | 3/2012 |
| WO | 12/087746 A1 | 6/2012 |
| WO | 2012/073985 A1 | 6/2012 |
| WO | 13/012733 A1 | 1/2013 |
| WO | 13/026839 A1 | 2/2013 |
| WO | 13/112986 A1 | 8/2013 |
| WO | 13/157105 A1 | 10/2013 |
| WO | 13/184761 A1 | 12/2013 |
| WO | 14/012085 A2 | 1/2014 |
| WO | 14/022540 A1 | 2/2014 |
| WO | 14/047231 A1 | 3/2014 |
| WO | 14/051433 A1 | 4/2014 |
| WO | 14/056783 A1 | 4/2014 |
| WO | 14/121087 A1 | 8/2014 |
| WO | 2015/006749 A2 | 1/2015 |
| WO | 15/091738 A1 | 6/2015 |
| WO | 15/143079 A1 | 9/2015 |
| WO | 16/161010 A2 | 10/2016 |
| WO | 17/053856 A1 | 3/2017 |
| WO | 21/021469 A1 | 2/2021 |

OTHER PUBLICATIONS

Alegre et al., "Effect of a Single Amino Acid Mutation on the Activating and Immunosuppressive Properties of a Humanized OKT3 Monoclonal Antibody", J Immunol, 148(11):3461-3468, ISSN: 0022-1767, (1992).

Almagro et al., "Humanization of antibodies," Front Biosci, vol. 13, pp. 1619-163, (2008).

An et al., "IgG2m4, an engineered antibody isotype with reduced Fc function," Landes Bioscience, 1(6):572-579, (2009).

Anonymous, "Clinical Trails Register: A Phase I Study to Assess Safety and Tolerability of REGN1979, an anti-CD20 x anti-CD3 bispecific monoclonal antibody, and REGN2810, and anti-programmed death-1 (PD-1) monoclonal antibody, in Patients with B-cell Malignancies," p. 1, section A.3; p. 3, section E.1 [Retrieved from the Internet Mar. 14, 2017: <URL: https://www.clinicaltrailsregister.eu/ctr-search/trial/2015-001697-17/ES>].

Anonymous, "Study of REGN2810 and REGN1979 in Patients with Lymphoma or Acute Lymphoblastic Leukemia." [Retrieved from the Internet Mar. 15, 2017: <URL: https://www.api.liveclinicaltrials.com/trialpage?dcn=10963&city=Baltimore&country=UnitedStates&start=20&state=Maryland&conditions=lymphoma&id-207048402254>].

Armour et al., "Differential binding to human FcγRIIa and FcγRIIb receptors by human IgG wildtype and mutant antibodies," Molecular Immunology, 40:585-593, (2003).

Armour et al., "Recombinant human IgG molecules lacking Fcγ receptor I binding and monocyte triggering activities", J. Immunol., 29:2613-2624, (1999).

Baeuerle et al., "Bispecific T-cell engaging antibodies for cancer therapy," Cancer Res, 69(12):4941-4944, doi: 10.1158/0008-5472.CAN-09-0547, (2009).

Bargou et al., "Tumor egression in Cancer Patients by Very Low Doses of a T Cell-Engaging Antibody," Science Magazine, vol. 321: 974-977, (2008).

Becker et al., "Evaluation of a combinatorial cell engineering approach to overcome apoptotic effects in XBP-1(s) expressing cells," Journal of Biotechnology, vol. 164:198-206, (2010).

Bloom et al., "Intrachain disulfide bond in the core hinge region of human IgG4," Protein Science, 6:407-415, (1997).

Bortoletto et al., "Optimizing anti-CD3 affinity for effective T cell targeting against tumor cells," Eur. J. Immunol, vol. 32:3102-3107 (2002).

Brekke et al., "The structural requirements for complement activation by IgG: does it hinge on the hinge?" Today, 16(2):85-90, (1995).

Buhmann et al., "Immunotherapy of recurrent B-cell malignancies after allo-SCT with Bi20 (FBTA05), a trifunctional anti-CD3 x anti-CD20 antibody and donor lymphocyte infusion," Bone Marrow Transplantation, 43:383-397, (2009).

Buhmann et al., "Immunotherapy with FBTA05 (Bi20), a trifunctional bispecific anti-CD3 x anti-CD20 antibody and donor lymphocyte infusion (DLI) in relapsed or refractory B-cell lymphoma after allogeneic stem cell transplantation: study protocol of an investigator-driven, open-label, non-randomized, uncontrolled, doseescalating Phase I/II-trial," Journal of Translation Medicine, vol. 11:160, (2013); 9 pages. [Retrieved from the Internet at: <http://www.translational-medicine.com/content/11/1/1160>].

(56) References Cited

OTHER PUBLICATIONS

Canfield et al., "The Binding Affinity of Human IgG for Its High Affinity Fc Receptor is Determined by Multiple Amino Acids in the $C_H2$ Domain and is Modulated by the Hinge Region," J. Exp. Med., 173(6):1483-1491, (1991).
Cao et al., "Multiformat T-Cell-Engaging Bispecific Antibodies Targeting Human Breast Cancers," Angew Chern Int Ed Engl, 54(24):7022-7027, doi: 10.1002/anie.201500799, (2015).
Chappel et al., "Identification of a Secondary FcγRI Binding Site within a Genetically Engineered Human IgG," Journal of Biological Chemistry, 268(33): 25124-25131, (1993).
Chappel et al., "Identification of the FC-Gamma Receptor Class I Binding Site in Human Igg Through the Use of Recombinant Igg1-Igg2 Hybrid and Point-Mutated Antibodies," Proc. Natl. Acad. Sci. USA, 88(20):9036-9040, (1991).
Clark, "IgG Effector Mechanisms," Chem Immunol. Basel, Karger, 65:88-110, (1997).
Dall'Acqua et al., "Modulation of the Effector Functions of a Human IgG1 through Engineering of Its Hinge Region," Journal of Immunology, 177:1129-1138, (2006).
Damschroder et al., "Analysis of human and primate CD2 molecules by protein sequence and epitope mapping with anti-human CD2 antibodies," Molecular Immunology, vol. 41:985-1000, (2004).
Dangl et al., "Segmental flexibility and complement fixation of genetically engineered chimeric human, rabbit and mouse antibodies," The EMBO Journal, 7(7):1989-1994, (1988).
Duncan et al., "Localization of the binding site for the human high-affinity Fc receptor on IgG", Nature, 332:563-564, (1988).
Fossati et al., "Immunological changes in the ascites of cancer patients after intraperitoneal administration of the bispecific antibody catumaxomab (anti-EpCAManti-CD3)," Gynecol Oncol, 138(2):343-351, doi: 10.1016/J.YGYNO.2015.06.003, (2015).
Gergely et al., "The two binding-site models of human IgG binding Fcγ receptors", The FASEB Journal, 4:3275-3283, (1990).
Greenwood et al., "Structural Motifs Involved In Human IGG Antibody Effector Functions," Eur. J. Immunology, 23(5):1098-1104, (1993).
Grubb, "Human immunoglobulin allotypes and Mendelian polymorphisma of the human immunoglobulin genes," Oss CJ, Regenmortel MHV (eds): Immunochemistry, New York, Dekker; pp. 47-68 (1994).
Harlow et al., Antibodies, A Laboratory Manual, Cold Spring Harbor Laboratory; (1998) pp. 37-47.
Haso et al., "Anti-CD22-chimeric antigen receptors targeting B-cell precursor acute lymphoglastic leukemia," Blood, vol. 121 (No. 7):1165-1174, Feb. 14, 2013.
Hezareh et al., "Effector function activities of a panel of mutants of a broadly neutralizing antibody against human immunodeficiency virus type 1," J Virol, 75(24):12161-12168, doi: 10.1128/JVI.75.24.12161-12168.2001, (2001).
Jacobsen et al., "Molecular and Functional Characterization of Cynomolgus Monkey IgG Subclasses," Journal Immunology, 186:341-349, (2011).
Jefferis et al., "Interaction sites on human IgG-Fc for FcγR: current models", Immunology Letters, 82:57-65, (2002).
Jefferis et al., "Recognition sites on human IgG for Fcγ receptors: the role of glycosylation," Immunology Letters, 44:111-117, (1995).
Jung et al., "Target Cell-Induced T Cell Activation with Bi- and Trispecific Antibody Fragments", Eur J Immunol, vol. 21, pp. 2431-2435, doi: 10.1002/EJI.1830211020, (1991).
Kapur et al., "IgG-effector functions: The Good, The Bad and The Ugly," El Sevier, vol. 160:139-144, (2014).
Kohnke et al., "Increase of PD-L1 expressing B-precursor ALL cells in a patient resistant to the CD19/CD3-bispecific T cell engager antibody blinatumomab," Journal of Hematology & Oncology, vol. 8 (No. 111): 5 pages, (2015).
Kumar et al., "Expression of CD20 in B Cell Precursor Acute Lymphoblastic Leukemia," Indian J Hematol Blood Transfus, vol. 30 (No. 1):16-18, (2014).

Labrijn et al., "When binding is enough: nonactivating antibody formats", Current Opinion in Immunology, 20:479-485, (2008).
Lau et al., "Chimeric Anti-CD14 IGG2/4 Hybrid Antibodies for Therapeutic Intervention in Pig and Human Models of Inflammation," J Immunol, 191:4769-4777, doi: 10.4049/jimmunol.1301653, (2013).
Li et al., "A Novel Bispecific Antibody, S-Fab, Induces Potent Cancer Cell Killing," J Immunother, 38(9):350-356, doi: 10.1097/CJI.0000000000000099, (2015).
Lum et al., "CD20-Targeted T Cells after Stem Cell Transplantation for High Risk and Refractory Non-Hodgkin's Lymphoma," Pbiol Blood Marrow Transplant, 19(6):925-933, (2013).
Lum et al., "Multiple infusions of CD20-targeted T cells and low-dose IL-2 after SCT for high-risk non-Hodgkin's Tymphoma: A pilot study," Bone Marrow Transplantation, 49:73-79, (2004). [Published online Sep. 23, 2013].
Lund et al., "Human FcγRI and FcγRII Interact with Distinct but Overlapping Sites on Human IgG", Journal of Immunology, 147(8):2657-2662, (1991).
Michaelsen et al., "Antibody Dependent Cell-Mediated Cytotoxicity Induced by Chimeric Mouse-Human IgG Subclasses and IgG3 Antibodies with Altered Hinge Region," Molecular Immunology, 29(3):319-326, (1992).
Morgan et al., "The N-terminal end of the CH2 domain of chimeric human IgG1 anti-HLA-DR is necessary for Gig, FcγRI and FcγRII binding," Immunology, 86:319-324, (1995).
Mueller et al., "Humanized Porcine VCAM-Specific Monoclonal Antibodies with Chimeric IgG2/G4 Constant Regions Block Human Leukocyte Binding to Porcine Endothelial Cells," Molecular Immunology, 34(6): 441-452, (1997).
Natsume et al., "Engineered Antibodies of IgG1IIgG3 Mixed Isotype with Enhanced Cytotoxic Activities," Cancer Research, 68:(10):3863-3872, (2008).
NCBI MedGen 44126 definition for "Pre-B Acute Lumphoblastic Leukemia"; retrieved from the Internet on Dec. 11, 2018, pp. 1-4, available at <https://www.ncbi.nlm.nih.gov/medgen/44126/> (2018).
Oganesyan et al., "Structural characterization of a human Fc fragment engineered for lack of effector functions," Acta Crystallographica Section D Biological Crystallography, D64:700-704, (2008).
Ontology Lookup Service, EFO 0000220, "acute lumphoblastic leukemia", retrieved from the Internet on Dec. 11, 2018, pp. 1-6, available at <https://www.ebi.ac.uk/ols/ontologies/efo/terms7short_form=EFO_0000220> (2018).
Patel et al., "IGG subclass variation of a monoclonal antibody binding to human Fc-gamma receptors", American Journal of Biochemistry and Biotechnology, 9(3):206-218, (2013).
Peters et al., "Engineering an Improved IgG4 Molecule with Reduced Disulfide Bond Heterogeneity and Increased Fab Domain Thermal Stability," Journal of Biological Chemistry, 287(29): 24525-24533, (2012).
Reddy et al., "Elimination of Fc Receptor-Dependent Effector Functions of a Modified IgG4 Monoclonal Antibody to Human CD4," Journal of Immunology, 164:1925-1933, (2000).
Rother et al., "Discovery and development of the complement inhibitor eculizumab for the treatment of paroxysmal nocturnal hemoglobinuna," Nature Biotechnology, 25(11):1256-1264, (2007).
Roux et al., "Comparisons of the ability of human IgG3 hinge mutants, IgM, IgE and IgA2, to form small immune complexes: Arole for flexibility and geometry," The Journal of Immunology, 161:4083-4090, (1998).
Roux et al., "Flexibility of Human IgG Subclasses," Journal of Immunology, 159:3372-3382, (1997).
Ruf et al., "Induction of a long-lasting antitumor immunity by a trifunctional bispecific antibody," Blood Journal, vol. 98, No. 9: 2526-2534, (2001).
Salfeld, "Isotype selection in antibody engineering," Nature Biotechnology, 25(12):1369-1372, (2007).
Sarmay et al., "Mapping and Comparison of the Interaction Sites on the Fc Region of IgG Responsible for Triggering Antibody Dependent Cellular Cytotoxicity (ADCC) through Different Types of Human Fcγ Receptor," Molecular Immunology, 29(5):633-639, (1992).

(56) References Cited

OTHER PUBLICATIONS

Sathish et al., "Challenges and approaches for the development of safer immunomodulatory biologics," Nature Reviews Drug Discovery, 12:306-324, (2013).
Schaefer et al., "Immunoglobulin domain crossover as a generic approach for the production of bispecific IgG antibodies," PNAS, 108(27):11187-11192, doi: 10.1073/pnas.1019002108, (2011).
Schuster et al., "Immunotherapy with the trifunctional anti-CD20 x anti-CD3 antibody FBTA05 Lymphomun) in paediatric high-risk patients with recurrent CD20-positive B cell malignancies," British Journal of Haematolgy, vol. 169 (No. 1): (Apr. 11, 2015); pp. 90-102.
Sensel et al., "Amino Acid Differences in the N-Terminus of CH2 Influence the Relative Abilities of IgG2 and IgG3 to Activate Complement", Molecular Immunology, 34(14):1019-1029, (1997).
Shields et al., High resolution mapping of the binding site on human IgG1 for FcγRI, FcγRII, Fcγ RIII, and FcRn and design of IgG1 variants with improved binding to the FcγR, J Biol Chem, 276(9):6591-6604, doi: 10.1074/JBC.M009483200, (2001).
Siberil et al., "Molecular aspects of human FcγR interactions with IgG: Functional and therapeutic consequences," Immunology Letters, 106:111-118, (2006).
Smith et al., "A novel, native-format bispecific antibody triggering T-cell killing of B-cell is robustly active in mouse tumor models and cynomolgus monkeys," Scientific Reports, vol. 5(No. 11):(Dec. 11, 2015); p. 17943.
Stanglmaier et al., "Bi20 (FBTA05), a novel trifunctional bispecific antibody (anti-CD20 x anti-CD3), mediates efficient killing of B-cell lymphoma cells even with very low CD20 expression levels", Int. J. Cancer, 123(5):1181-1189, (2008).
Stevenson, "Chemical Engineering at the Antibody Hinge," Chem Immunol. Basel, Karger, 65:57-72, (1997).
Strop et al., "Generating Bispecific Human IgG1 and IgG2 Antibodies from Any Antibody Pair", J. Mol. Biol., 420(3):204-219, (2012).
Stubenrauch et al., "Impact of Molecular Processing in the Hinge Region of Therapeutic IgG4 Antibodies on Disposition Profiles in Cynomolgus Monkeys," Drug Metabolism and Disposition, vol. 38(No. 1):84-91, (2010).
Sun et al., "Anti-CD20/CD3 T cell-dependent bispecific antibody for the treatment of B cell malignancies," Science Translational Medicine, 7(287):287ra70, 10 pages, (2015).
Tan et al., "Influence of the hinge region on complement activation, C1q binding, and segmental flexibility in chimeric human immunoglobulins,", Proc. Natl. Acad. Sci. USA, 87:162-166, (1990).
Thomas et al., "Chemoimmunotherapy with a Modified Hyper-CVAD and Rituximab Regimen Improves Outcome in De Novo Philadelphia Chromosome-Negative Precursor B-Lineage Acute Lymphoblastic Leukemia," Journal of Clinical Oncology, vol. 28 (No. 24):3880-3889; Aug. 20, 2010.
Topp et al., "Safety and activity of blinatumomab for adult patients with relapsed or refractory B-precursor acute lymphoblastic leukemia: a multicentre, single-arm, phase 2 study," Publication, vol. 16:57-66, (Jan. 2015).
Tsai et al., "Regulation of CD20 in Rituximab-Resistant Cell Lines and B-cell Non-Hodgkin Lymphoma," Clinical Cancer Research, vol. 18(No. 4):1039-1050, (2012).
U.S. Appl. No. 14/170,166, Non-Final Office Action dated Dec. 21, 2015.
U.S. Appl. No. 14/170,166, Notice of Allowance dated Apr. 11, 2016.
U.S. Appl. No. 14/170,166, Requirement for Restriction/Election dated Jul. 27, 2015.
U.S. Appl. No. 15/147,791, Non-Final Office Action dated Sep. 27, 2017.
U.S. Appl. No. 15/147,791, Notice of Allowance dated Mar. 1, 2018.
U.S. Appl. No. 15/147,791, Notice of Allowance dated Jun. 12, 2018.
U.S. Appl. No. 15/562,881, Notice of Allowance dated Jun. 12, 2019.
U.S. Appl. No. 15/562,881, Notice of Allowance dated Sep. 25, 2019.
Vafa, et al., "An engineered Fc variant of an IgG eliminates all immune effector functions via structural perturbations", 65:114-126, (2014). (057Published online Jul. 17, 2013).
Vidarsson et al., "IgG Subclasses and Allotypes: From Structure to Effector Functions," Frontiers in Immunology, vol. 5, Article 520, 18 pages, doi: 10.3389/fimmu.2014.00520, (2014).
Ward et al., "The effector functions of immunoglobulins: implications for therapy," Therapeutic Immunology, 2:77-94, (1995).
WIPO Application No. PCT/US2014/014175, PCT International Preliminary Report on Patentability dated Aug. 13, 2015.
WIPO Application No. PCT/US2014/014175, PCT International Search Report and Written Opinion of the International Searching Authority dated Jul. 9, 2014.
WIPO Application No. PCT/US2016/025051, PCT International Search Report and Written Opinion of the International Searching Authority dated Oct. 12, 2016.
WIPO Application No. PCT/US2016/053525, PCT International Search Report and Written Opinion of the International Searching Authority dated Mar. 8, 2017.
Wolach et al., "Blinatumomab for the Treatment of Philadelphia Chromosome-Negative, Precursor B-cell Acute Lymphoblastic Leukemia," Clinical Cancer Research, vol. 21 (No. 19):4262-4269, (2015).
Wu et al., "Fab-based bispecific antibody formats with robust biophysical properties and biological activity," MABS, pp. 470-482, ISSN: 1942-0870, (2015).
Wypych et al., "Human IgG2 Antibodies Display Disulfide-mediated Structural Isoforms," Journal of Biological Chemistry, 283(23):16194-16205, (2008).
Xu et al., "Residue at Position 331 in the Igg1 and Igg4 Ch2 Domains Contributes to Their Differential Ability to Blind and Activate Complement," Journal of Biological Chemistry, 269(5):3469-3474, (1994).
PCT/US2014/014175, Jan. 31, 2014, WO 2014/022540, Expired, 8550-WO.
U.S. Appl. No. 17/355,532, filed Jun. 23, 2021, Pending, 9250US04.
U.S. Appl. No. 16/128,907, filed Sep. 12, 2018, US 2018-0371090, Pending, 8550US03.
U.S. Appl. No. 15/489,666, filed Apr. 17, 2017, US 2017-0320948, Pending, 9250US02.
U.S. Appl. No. 15/934,447, filed Mar. 23, 2018, US 2018-0215823, Pending, 9250US03.
PCT/U52013/060511, Sep. 19, 2013, WO 2014/047231, Expired, 9250-WO.
U.S. Appl. No. 16/716,980, filed Dec. 17, 2019, Pending, A0015US02.
U.S. Appl. No. 15/527,002, filed Nov. 17, 2015, US 2018-0194841, Pending, 10162US01.
U.S. Appl. No. 16/443,313, filed Jun. 17, 2019, Pending, 10241US02.
PCT/US2016/053525, Sep. 23, 2016, WO 2017/053856, Pending, 10151WO01.
U.S. Appl. No. 15/780,504, filed Sep. 23, 2016, US 2018-0355038, Pending, 10151US01.
U.S. Appl. No. 62/861,100, filed Jun. 13, 2019, Pending, 10496P3-US.
U.S. Appl. No. 16/556,885, filed Aug. 30, 2019, Pending, 10496US01.
PCT/US2019/049027, Aug. 30, 2019, WO 2020/047389, Pending, 10496WO01.
Bae et al., "Identification of the amino acid residues involved in human IgG transport into egg yolk of Japanese quail," Molucular Immunology, vol. 47:1404-1410, (2010).
Chan et al., "Therapeutic antibodies for autoimmunity and inflammation," Macmillan Publishers Limited (Nature Reviews, Immunology), vol. (10):301-316, (2010).
Richards et al., "Optimization of antibody binding to FcγRIIa enhances macrophage phagocytosis of tumor cells," Molecular Cancer Therapeutics (Xencor, Inc.), vol. (8):2517-2527, (2008). [Retrieved from the Internet Sep. 16, 2020: <URL: met.aacrjournals.org>].

(56) References Cited

OTHER PUBLICATIONS

Sun, "Structural Recognition of Immunoglobulins by Fcγ Receptors," Elsevier Science & Technology, Ch. 7:131-144, (2013).
U.S. Appl. No. 15/780,504, Requirement for Restriction/Election dated Apr. 7, 2020.
U.S. Appl. No. 16/128,907, Non-Final Office Action dated Sep. 22, 2020.
U.S. Appl. No. 15/780,504, Non-Final Office Action dated Oct. 20, 2020.
U.S. Appl. No. 16/128,907, Notice of Allowance dated Dec. 31, 2020.
Weinglass et al., "Engineering Conformational Flexibility in the Lactose Permease of *Escherichia coli*: Use of Glycine-Scanning Mutagenesis to Rescue Mutant Glu325—Asp," Biochemistry, vol. 40:769-776, (2001).
U.S. Appl. No. 61/759,578, filed Feb. 1, 2013, Expired, 8550P1.
U.S. Appl. No. 14/170,166, filed Jan. 31, 2014, U.S. Pat. No. 9,359,437, Issued, 8550-US.
U.S. Appl. No. 15/147,791, filed May 5, 2016, U.S. Pat. No. 10,106,610, Issued, 8550US02.
U.S. Appl. No. 16/128,907, filed Sep. 12, 2018, U.S. Pat. No. 10,988,537, Issued, 8550US03.
PCT/US2014/014175, Jan. 31, 2014, WO 2014/022540, Expired, 8550-WO.
U.S. Appl. No. 17/217,567, filed Mar. 30, 2021, US-2021-0246207, Published, 8550US04.
U.S. Appl. No. 61/704,029, filed Sep. 21, 2012, Expired, 9250P1.
U.S. Appl. No. 61/753,461, filed Jan. 17, 2013, Expired, 9250P2.
U.S. Appl. No. 61/763,110, filed Feb. 11, 2013, Expired, 9250P3.
U.S. Appl. No. 61/827,098, filed May 24, 2013, Expired, 9250P4.
U.S. Appl. No. 14/031,075, filed Sep. 19, 2013, U.S. Pat. No. 9,657,102, Issued, 9250-US.
U.S. Appl. No. 15/489,666, filed Apr. 17, 2017, U.S. Pat. No. 11,072,656, Issued, 9250US02.
U.S. Appl. No. 15/934,447, filed Mar. 23, 2018, U.S. Pat. No. 11,155,621, Issued, 9250US03.
PCT/US2013/060511, Sep. 19, 2013, WO 2014/047231, Expired, 9250-WO.
U.S. Appl. No. 17/355,532, filed Jun. 23, 2021, US-2022-0144947, Published, 9250US04.
U.S. Appl. No. 61/955,663, filed Mar. 19, 2014, Expired, A0015P1.
U.S. Appl. No. 61/981,641, filed Apr. 18, 2014, Expired, A0015P2.
U.S. Appl. No. 62/007,385, filed Jun. 3, 2014, Expired, A0015P3.
U.S. Appl. No. 62/033,460, filed Aug. 5, 2014, Expired, A0015P4.
U.S. Appl. No. 14/661,334, filed Mar. 18, 2015, U.S. Pat. No. 10,550,193, Issued, A0015US01.
PCT/US2015/021322, Mar. 18, 2015, WO 2015/143079, Expired, A0015WO01.
U.S. Appl. No. 16/716,980, filed Dec. 17, 2019, US-2020-0115464, Published, A0015US02.
U.S. Appl. No. 62/080,716, filed Nov. 17, 2014, Expired, 10162P1-US.
U.S. Appl. No. 62/160,788, filed May 13, 2015, Expired, 10162P2-US.
PCT/US2015/061139, Nov. 17, 2015, WO 2016/081490, Expired, 10162WO01.
U.S. Appl. No. 15/527,002, filed Nov. 17, 2015, U.S. Pat. No. 10,662,244, Issued, 10162US01.
U.S. Appl. No. 62/306,031, filed Mar. 9, 2016, Expired, 10241P1-US.
U.S. Appl. No. 15/386,443, filed Dec. 21, 2016, US 2017-0174781, Abandoned, 10241US01.
PCT/US2016/068003, Dec. 21, 2016, WO 2017/112762, Expired, 10241WO01.
U.S. Appl. No. 16/443,313, filed Jun. 17, 2019, Abandoned, 10241US02.
U.S. Appl. No. 62/140,350, filed Mar. 30, 2015, Expired, 10140P1-US.
PCT/US2016/025051, Mar. 30, 2016, WO 2016/161010, Expired, 10140WO01.
U.S. Appl. No. 15/562,881, filed Mar. 30, 2016, U.S. Pat. No. 10,556,952, Issued, 10140US01.
U.S. Appl. No. 62/222,605, filed Sep. 23, 2015, Expired, 10151P1-US.
PCT/US2016/053525, Sep. 23, 2016, WO 2017/053856, Expired, 10151WO01.
U.S. Appl. No. 15/780,504, filed Sep. 23, 2016, US 2018-0355038, Abandoned, 10151US01.
U.S. Appl. No. 17/207,462, filed Mar. 19, 2021, US-2021-0253701, Published, 10151US02.
U.S. Appl. No. 62/726,137, filed Aug. 31, 2018, Expired, 10496P1-US.
U.S. Appl. No. 62/774,019, filed Nov. 30, 2018, Expired, 10496P2-US.
U.S. Appl. No. 62/861,100, filed Jun. 13, 2019, Expired, 10496P3-US.
U.S. Appl. No. 16/556,885, filed Aug. 30, 2019, US-2020-0129617, Published, 10496US01.
PCT/US2019/049027, Aug. 30, 2019, WO 2020/047389, Published, 10496WO01.
Bannerji et al., "Phase 1 Study of REGN1979, an Anti-CD20 x Anti-CD3 Bispecific Monoclonal Antibody, in Patients with CD20+ B-Cell Malignancies Previously Treated with CD20-Directed Antibody Therapy," Blood, vol. 128 (22): 621 (2016). [http://doi.org/10.1182/blood.V128.22.621.621].
U.S. Appl. No. 16/556,885, Non-Final Office Action dated Mar. 29, 2022.
Varghese et al., "A Novel CD20-CD3 Bispecific Fully Human Antibody Induces Potent Anti-Tumor Effects Against B Cell Lymphoma in Mice," Blood, vol. 124 (21) 4501 (2014). [http://doi.org/10.1182/blood.V124.21.4501.4501].

\* cited by examiner

Figure 2:
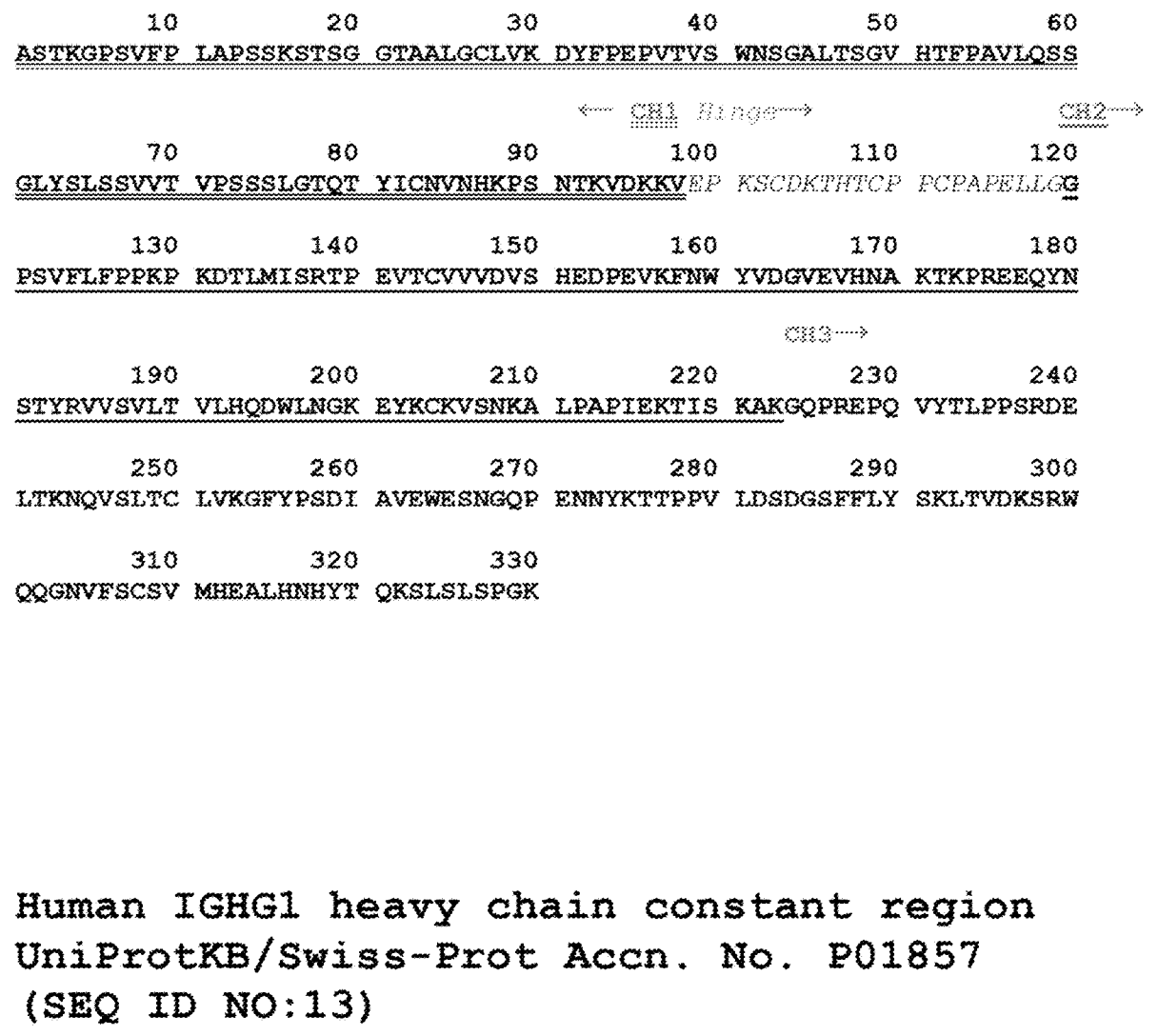

```
          10          20          30          40          50          60
ASTKGPSVFP LAPSSKSTSG GTAALGCLVK DYFPEPVTVS WNSGALTSGV HTFPAVLQSS
                                                                    CH2--->
          70          80          90         100         110         120
GLYSLSSVVT VPSSSLGTQT YICNVNHKPS NTKVDKKV EP KSCDKTHTCP PCPAPELLGG
                                 <---CH1   Hinge--->

130         140         150         160         170         180
PSVFLFPPKP KDTLMISRTP EVTCVVVDVS HEDPEVKFNW YVDGVEVHNA KTKPREEQYN
                                                           CH3--->
         190         200         210         220         230         240
STYRVVSVLT VLHQDWLNGK EYKCKVSNKA LPAPIEKTIS KAKGQPREPQ VYTLPPSRDE 250         260         270         280         290         300
LTKNQVSLTC LVKGFYPSDI AVEWESNGQP ENNYKTTPPV LDSDGSFFLY SKLTVDKSRW 310         320         330
QQGNVFSCSV MHEALHNHYT QKSLSLSPGK
```

Human IGHG1 heavy chain constant region
UniProtKB/Swiss-Prot Accn. No. P01857
(SEQ ID NO:13)

FIG. 3

```
         10         20         30         40         50         60
ASTKGPSVFP LAPCSRSTSE STAALGCLVK DYFPEPVTVS WNSGALTSGV HTFPAVLQSS
                                            <--CH1 hinge-->      CH2-->
         70         80         90        100        110        120
GLYSLSSVVT VPSSNFGTQT YTCNVDHKPS NTKVDKTVER KCCVECPPCP APPVAGPSVF 130        140        150        160        170        180
LFPPKPKDTL MISRTPEVTC VVVDVSHEDP EVQFNWYVDG VEVHNAKTKP REEQFNSTFR
                                            <--CH3-->
        190        200        210        220        230        240
VVSVLTVVHQ DWLNGKEYKC KVSNKGLPAP IEKTISKTKG QPREPQVYTL PPSREEMTKN 250        260        270        280        290        300
QVSLTCLVKG FYPSDISVEW ESNGQPENNY KTTPPMLDSD GSFFLYSKLT VDKSRWQQGN 310        320
VFSCSVMHEA LHNHYTQKSL SLSPGK
```

Human IGHG2 heavy chain constant region
UniProtKB/Swiss-Prot Accn. No. P01859
(SEQ ID NO:14)

FIG. 4

```
         10         20         30         40         50         60
ASTKGPSVFP LAPCSRSTSE STAALGCLVK DYFPEPVTVS WNSGALTSGV HTFPAVLQSS
                                              <---CH1 HINGE---->  <----CH2
         70         80         90        100        110        120
GLYSLSSVVT VPSSSLGTKT YTCNVDHKPS NTKVDKRVES KYGPPCPSCP APEFLGGPSV
        130        140        150        160        170        180
FLFPPKPKDT LMISRTPEVT CVVVDVSQED PEVQFNWYVD GVEVHNAKTK PREEQFNSTY
                                          <---CH3---->
        190        200        210        220        230        240
RVVSVLTVLH QDWLNGKEYK CKVSNKGLPS SIEKTISKAK GQPREPQVYT LPPSQEEMTK
        250        260        270        280        290        300
NQVSLTCLVK GFYPSDIAVE WESNGQPENN YKTTPPVLDS DGSFFLYSRL TVDKSRWQEG
        310        320
NVFSCSVMHE ALHNHYTQKS LSLSLGK
```

Human IGHG4 heavy chain constant region
UniProtKB/Swiss-Prot Accn. No. P01861
(SEQ ID NO: 15)

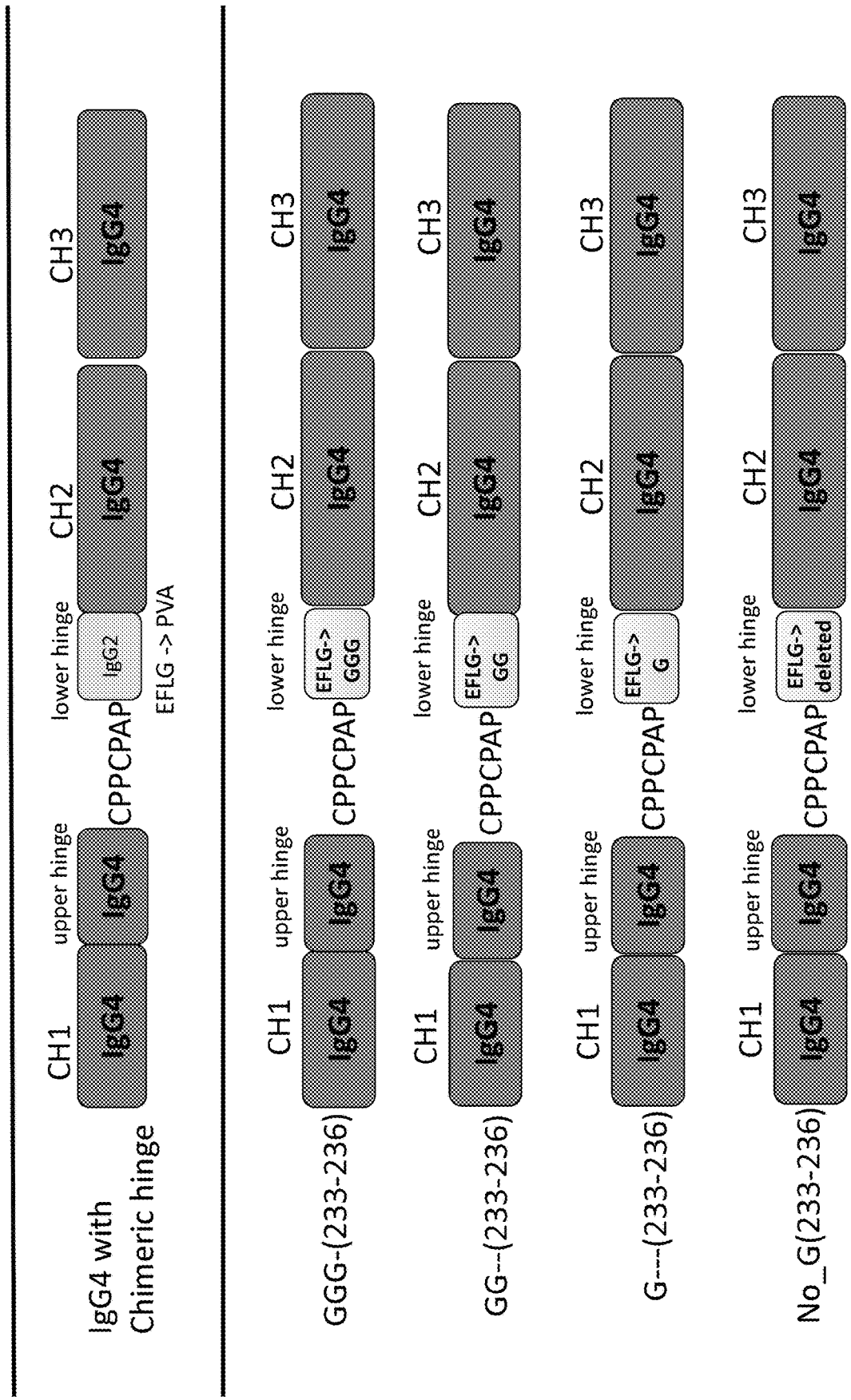

FIG. 6

| mAb designation | Target arm | Construct description | hFcRy1 captured (RU) | mAb-5uM bound (RU) | ka | kd | KD | t1/2 (min) | Rmax |
|---|---|---|---|---|---|---|---|---|---|
| 9F7_VH_IgG4__GGG-(233-236) | aCD3(9F7) bivalent | lower hinge of IgG4 at 233-236 replaced with GGG (and S228P) | 171 | 1 | NB | NB | NB | NB | NB |
| 9F7_VH_IgG4__GG--(233-236) | aCD3(9F7) bivalent | lower hinge of IgG4 at 233-236 replaced with GG (and S228P) | 171 | -1 | NB | NB | NB | NB | NB |
| 9F7_VH_IgG4_G---(233-236) | aCD3(9F7) bivalent | lower hinge of IgG4 at 233-236 replaced with G (and S228P) | 170 | 0 | NB | NB | NB | NB | NB |
| 9F7_VH_IgG4_No_G(233-236) | aCD3(9F7) bivalent | lower hinge of IgG4 at 233-236 deleted (and S228P) | 169 | -1 | NB | NB | NB | NB | NB |
| Control Ab A (Lot-L2) 9F7_VH_IgG4 | aCD3(9F7) bivalent | wild type IgG4 Fc (except CH3 mutation 435R and 436F) | 168 | 112 | 8.20E+05 | 2.30E-03 | 2.81E-09 | 5 | 94 |
| Control Ab D (Lot-L5) 9F7_VLx3B9_VH_IgG4_PVA | aCD3(9F7) x aCD20(3B9) | Bispecific mAb with lower hinge of IgG4 at 233-236 replaced with PVA (and S228P) | 169 | 0 | NB | NB | NB | NB | NB |
| Control Ab B (Lot-L2) 9F7_VH_IgG1 | aCD3(9F7) bivalent | wild type IgG1 Fc | 170 | 128 | 7.10E+05 | 8.84E-04 | 1.25E-09 | 13 | 110 |

NB: No binding

FIG. 7

| mAb designation | Target arm | Construct description | hFcRyIIa captured (RU) | mAb -5uM bound (RU) | ka | kd | KD* | t1/2 (min)* | Rmax |
|---|---|---|---|---|---|---|---|---|---|
| 9F7_VH_IgG4__GGG-(233-236) | aCD3(9F7) bivalent | lower hinge of IgG4 at 233-236 replaced with GGG (and S228P) | 323 | -1 | NB | NB | NB | NB | NB |
| 9F7_VH_IgG4__GG--(233-236) | aCD3(9F7) bivalent | lower hinge of IgG4 at 233-236 replaced with GG (and S228P) | 319 | -3 | NB | NB | NB | NB | NB |
| 9F7_VH_IgG4_G---(233-236) | aCD3(9F7) bivalent | lower hinge of IgG4 at 233-236 replaced with G (and S228P) | 318 | -2 | NB | NB | NB | NB | NB |
| 9F7_VH_IgG4_No_G(233-236) | aCD3(9F7) bivalent | lower hinge of IgG4 at 233-236 deleted (and S228P) | 320 | 4 | - | - | IC | - | 730 |
| Control Ab A (Lot-L2) 9F7_VH_IgG4 | aCD3(9F7) bivalent | wild type IgG4 Fc (except CH3 mutation 435R and 436F) | 320 | 156 | - | - | 16.8uM | - | 730 |
| Control Ab D (Lot-L5) 9F7_VLx3B9_VH_IgG4_PVA | aCD3(9F7) x aCD20(3B9) | Bispecific mAb with lower hinge of IgG4 at 233-236 replaced with PVA (and S228P) | 320 | 121 | - | - | 22.9uM | - | 730 |
| Control Ab B (Lot-L2) 9F7_VH_IgG1 | aCD3(9F7) bivalent | wild type IgG1 Fc | 321 | 411 | - | - | 3.12uM | - | 730 |

NB: No binding
IC: value cannot be determined

*KDs were derived using steady state equilibrium dissociation constant

FIG. 8

| mAb Designation | Target arm | Construct description | hFcRyIIb captured (RU) | mAb -5uM bound (RU) | ka | kd | KD* | t1/2 (min)* | Rmax |
|---|---|---|---|---|---|---|---|---|---|
| 9F7_VH_IgG4_GGG-(233-236) | aCD3(9F7) bivalent | lower hinge of IgG4 at 233-236 replaced with GGG (and S228P) | 392 | -31 | NB | NB | NB | NB | NB |
| 9F7_VH_IgG4_GG--(233-236) | aCD3(9F7) bivalent | lower hinge of IgG4 at 233-236 replaced with GG (and S228P) | 390 | -32 | NB | NB | NB | NB | NB |
| 9F7_VH_IgG4_G---(233-236) | aCD3(9F7) bivalent | lower hinge of IgG4 at 233-236 replaced with G (and S228P) | 386 | -31 | NB | NB | NB | NB | NB |
| 9F7_VH_IgG4_No_G(233-236) | aCD3(9F7) bivalent | lower hinge of IgG4 at 233-236 deleted (and S228P) | 387 | -36 | NB | NB | NB | NB | NB |
| Control Ab A (Lot-L2) 9F7_VH_IgG4 | aCD3(9F7) bivalent | wild type IgG4 Fc (except CH3 mutation 435R and 436F) | 388 | 276 | - | - | 2.20uM | - | 393 |
| Control Ab D (Lot-L5) 9F7_VLx3B9_VH_IgG4_PVA | aCD3(9F7) x aCD20(3B9) | Bispecific mAb with lower hinge of IgG4 at 233-236 replaced with PVA (and S228P) | 388 | 17 | - | - | 110uM | - | 393 |
| Control Ab B (Lot-L2) 9F7_VH_IgG1 | aCD3(9F7) bivalent | wild type IgG1 Fc | 387 | 221 | - | - | 4.0uM | - | 393 |

*KDs were derived using steady state equilibrium dissociation constant

NB: No binding

FIG. 9

| mAb Designation | Target arm | Construct description | hFcRyIIIA captured (RU) | mAb-5uM bound (RU) | ka | kd | KD* | t1/2 (min)* | Rmax |
|---|---|---|---|---|---|---|---|---|---|
| 9F7_VH_IgG4_GGG-(233-236) | aCD3(9F7) bivalent | lower hinge of IgG4 at 233-236 replaced with GGG (and S228P) | 398 | -48 | NB | NB | NB | NB | NB |
| 9F7_VH_IgG4_GG--(233-236) | aCD3(9F7) bivalent | lower hinge of IgG4 at 233-236 replaced with GG (and S228P) | 380 | -44 | NB | NB | NB | NB | NB |
| 9F7_VH_IgG4_G---(233-236) | aCD3(9F7) bivalent | lower hinge of IgG4 at 233-236 replaced with G (and S228P) | 381 | -51 | NB | NB | NB | NB | NB |
| 9F7_VH_IgG4_No_G(233-236) | aCD3(9F7) bivalent | lower hinge of IgG4 at 233-236 deleted (and S228P) | 382 | -56 | NB | NB | NB | NB | NB |
| Control Ab A (Lot-L2) 9F7_VH_IgG4 | aCD3(9F7) bivalent | wild type IgG4 Fc (except CH3 mutation 435R and 436F) | 383 | 17 | - | - | 140uM | - | 528 |
| Control Ab D Lot-L5 9F7_VLx3B9_VH_IgG4_PVA | aCD3(9F7) x aCD20(3B9) | Bispecific mAb with lower hinge of IgG4 at 233-236 replaced with PVA (and S228P) | 382 | -5 | NB | NB | NB | NB | NB |
| Control Ab B (Lot-L2) 9F7_VH_IgG1 | aCD3(9F7) bivalent | wild type IgG1 Fc | 382 | 399 | - | - | 1.76uM | - | 528 |

*KDs were derived using steady state equilibrium dissociation constant

NB: No binding

FIG. 10

| mAb designation | Target arm | Construct description | hFcRn captured (RU) | mAb-5uM bound (RU) | ka | kd | KD* | t1/2 (min)* |
|---|---|---|---|---|---|---|---|---|
| 9F7_VH_IgG4_GGG-(233-236) | aCD3(9F7) bivalent | lower hinge of IgG4 at 233-236 replaced with GGG (and S228P) | 214 | 22 | 2.42E+04 | 7.13E-02 | 2.95E-06 | 9.7 |
| 9F7_VH_IgG4_GG--(233-236) | aCD3(9F7) bivalent | lower hinge of IgG4 at 233-236 replaced with GG (and S228P) | 190 | 11 | 8.89E+04 | 9.06E-02 | 1.02E-06 | 7.6 |
| 9F7_VH_IgG4_G---(233-236) | aCD3(9F7) bivalent | lower hinge of IgG4 at 233-236 replaced with G (and S228P) | 171 | 14 | 2.68E+04 | 7.26E-02 | 2.71E-06 | 9.5 |
| 9F7_VH_IgG4_No_G(233-236) | aCD3(9F7) bivalent | lower hinge of IgG4 at 233-236 deleted (and S228P) | 155 | 43 | 5.23E+04 | 6.97E-02 | 1.33E-06 | 9.9 |
| Control Ab A (Lot- L2) 9F7_VH_IgG4 | aCD3(9F7) bivalent | wild type IgG4 Fc (except CH3 mutation 435R and 436F) | 299 | 25 | 9.46E+04 | 1.47E-01 | 1.55E-06 | 4.7 |
| Control Ab D (Lot- L5) 9F7_VLx3B9_VH_IgG4_PVA | aCD3(9F7) bivalent | Bispecific mAb with lower hinge of IgG4 at 233-236 replaced with PVA (and S228P) | 246 | 21 | 1.91E+05 | 1.77E-01 | 9.25E-07 | 3.9 |

*KDs were derived using steady state equilibrium dissociation constant

Testing the aCD3 supernatants for binding to FcγR1 : U937 calcein killing assay

Testing the aCD3 purified mAbs for binding to FcγR1 : U937 calcein killing assay

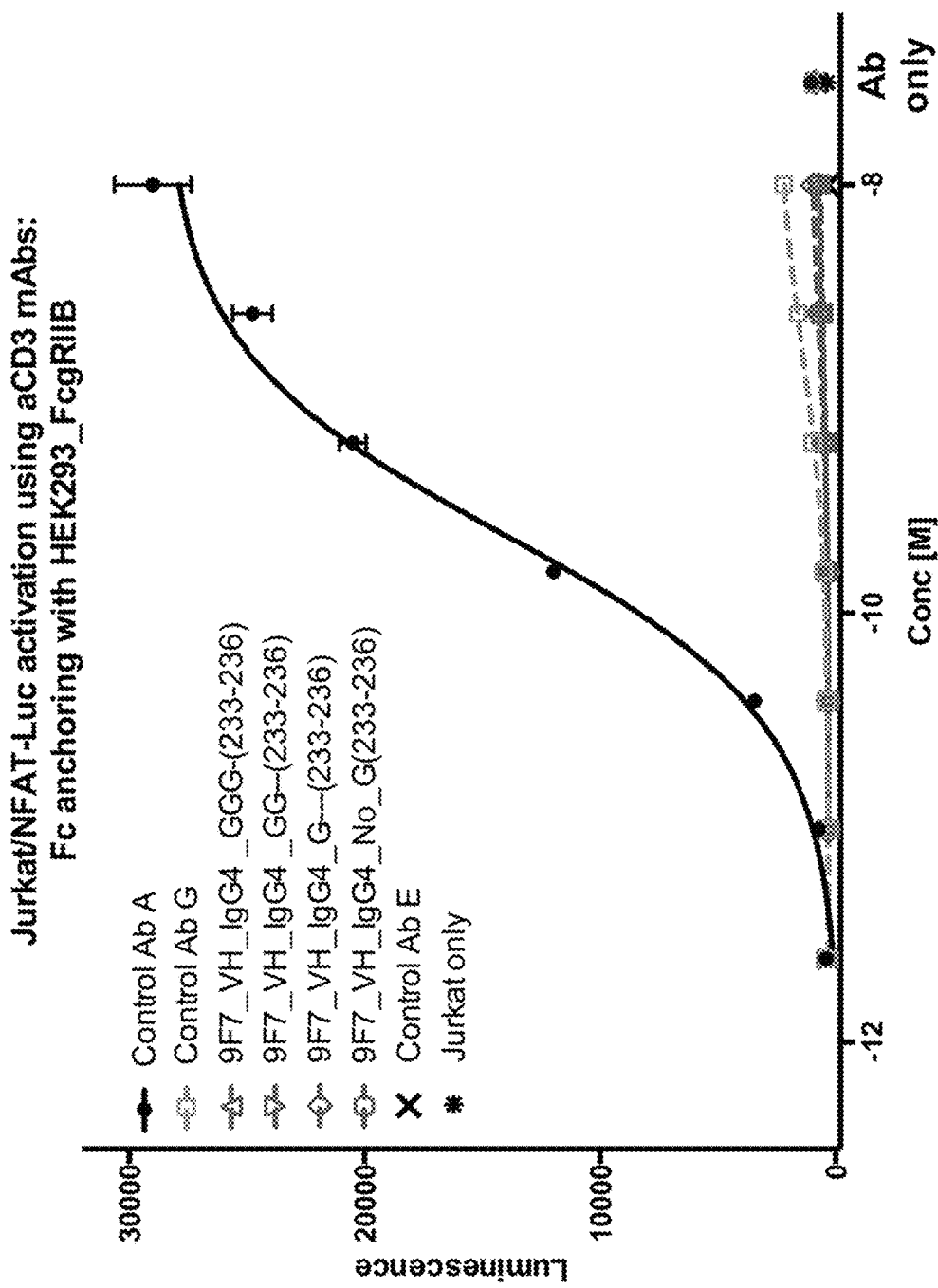

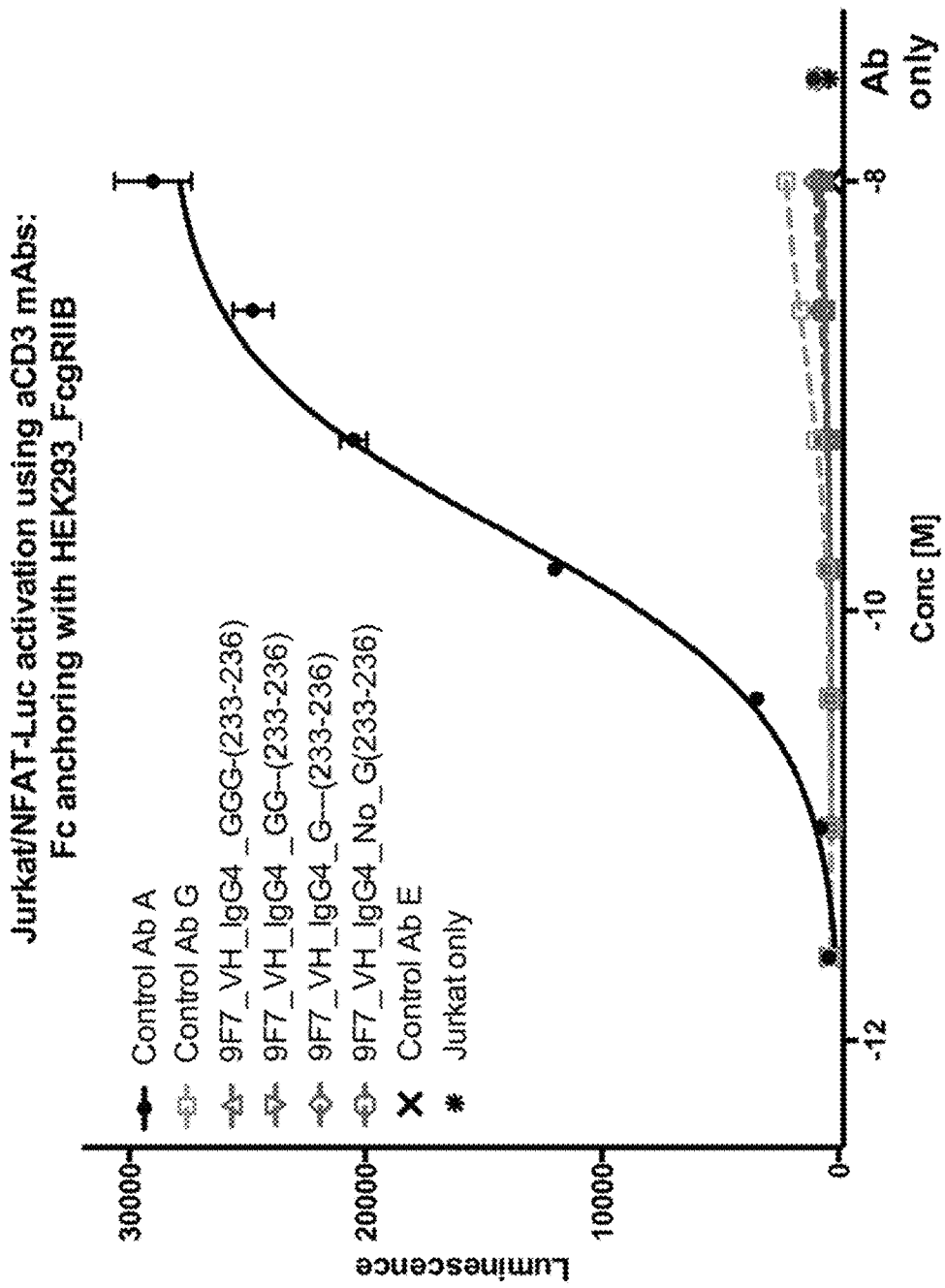

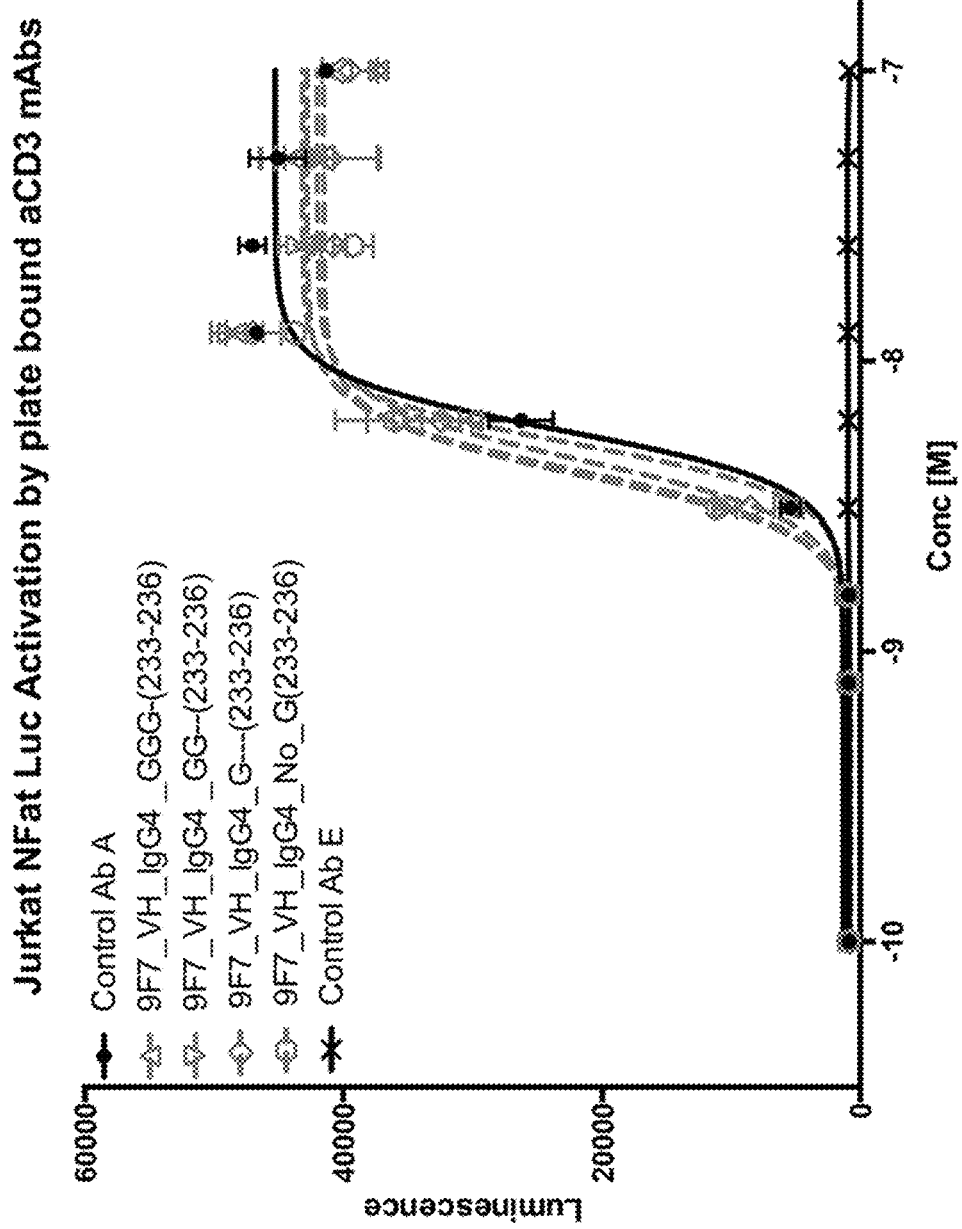

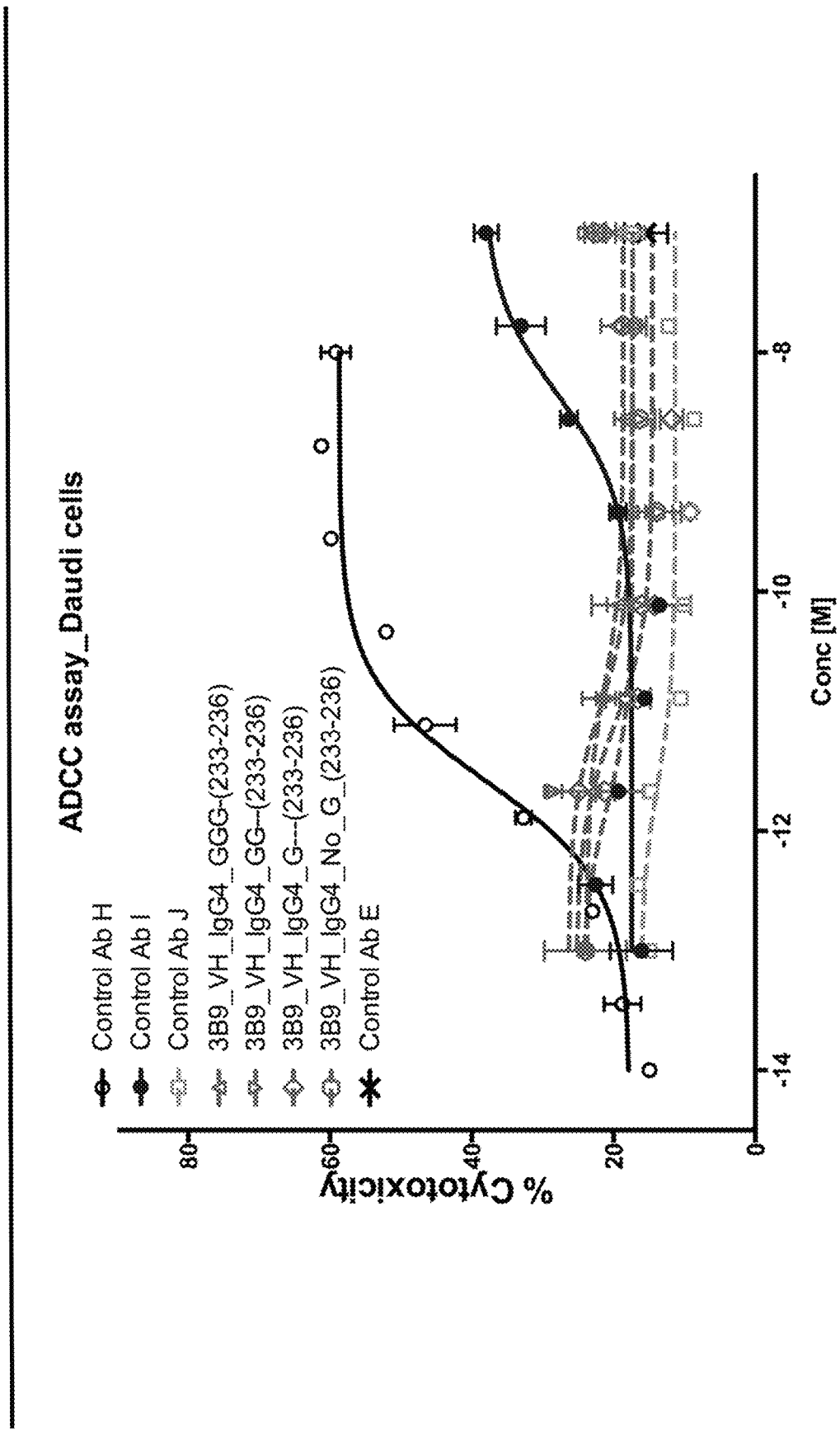

SEQUENCE LISTING

<160> NUMBER OF SEQ IDS NOS: 31

<210> SEQ ID NO 1
<211> LENGTH: 14
<212> TYPE: PRT
<213> ORGANISM: Artificial Sequence
<220> FEATURE:
<223> OTHER INFORMATION: Synthetic

<400> SEQUENCE: 1

Pro Pro Cys Pro Ala Pro Gly Gly Gly Gly Pro Ser Val Phe
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic

<400> SEQUENCE: 2

Cys Pro Pro Cys Pro Ala Pro Gly Gly Gly Pro Ser Val Phe
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic

<400> SEQUENCE: 3

Cys Pro Pro Cys Pro Ala Pro Gly Gly Pro Ser Val Phe
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

Cys Pro Pro Cys Pro Ala Pro Gly Pro Ser Val Phe
1               5                   10

<210> SEQ ID NO 5
<211> LENGTH: 326
<212> TYPE: PRT
<213> ORGANISM: Artificial Sequence
<220> FEATURE:
<223> OTHER INFORMATION: Synthetic

<400> SEQUENCE: 5

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Gly Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

```
Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
290                 295                 300

Ser Val Met His Glu Ala Leu His Asn His Tyr Thr Gln Lys Ser Leu
305                 310                 315                 320

Ser Leu Ser Leu Gly Lys
            325
```

<210> SEQ ID NO 6
<211> LENGTH: 325
<212> TYPE: PRT
<213> ORGANISM: Artificial Sequence
<220> FEATURE:
<223> OTHER INFORMATION: Synthetic

<400> SEQUENCE: 6

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Gly Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser Gln Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Tyr Arg Val Val Ser Val Leu Thr Val Leu His Gln Asp Trp Leu
            180                 185                 190

Asn Gly Lys Glu Tyr Lys Cys Lys Val Ser Asn Lys Gly Leu Pro Ser
        195                 200                 205

Ser Ile Glu Lys Thr Ile Ser Lys Ala Lys Gly Gln Pro Arg Glu Pro
    210                 215                 220

Gln Val Tyr Thr Leu Pro Pro Ser Gln Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Val Leu Asp Ser Asp Gly Ser Phe Phe Leu Tyr Ser Arg Leu
        275                 280                 285

Thr Val Asp Lys Ser Arg Trp Gln Glu Gly Asn Val Phe Ser Cys Ser
    290                 295                 300
```

```
Val Met His Glu Ala Leu His Asn His Tyr Thr Gln Lys Ser Leu Ser
305                 310                 315                 320

Leu Ser Leu Gly Lys
            325
```

<210> SEQ ID NO 7
<211> LENGTH: 324
<212> TYPE: PRT
<213> ORGANISM: Artificial Sequence
<220> FEATURE:
<223> OTHER INFORMATION: Synthetic

<400> SEQUENCE: 7

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Gly Pro Ser Val Phe Leu Phe Pro Pro Lys Pro Lys Asp Thr Leu
        115                 120                 125

Met Ile Ser Arg Thr Pro Glu Val Thr Cys Val Val Val Asp Val Ser
    130                 135                 140

Gln Glu Asp Pro Glu Val Gln Phe Asn Trp Tyr Val Asp Gly Val Glu
145                 150                 155                 160

Val His Asn Ala Lys Thr Lys Pro Arg Glu Glu Gln Phe Asn Ser Thr
                165                 170                 175

Tyr Arg Val Val Ser Val Leu Thr Val Leu His Gln Asp Trp Leu Asn
            180                 185                 190

Gly Lys Glu Tyr Lys Cys Lys Val Ser Asn Lys Gly Leu Pro Ser Ser
        195                 200                 205

Ile Glu Lys Thr Ile Ser Lys Ala Lys Gly Gln Pro Arg Glu Pro Gln
    210                 215                 220

Val Tyr Thr Leu Pro Pro Ser Gln Glu Glu Met Thr Lys Asn Gln Val
225                 230                 235                 240

Ser Leu Thr Cys Leu Val Lys Gly Phe Tyr Pro Ser Asp Ile Ala Val
                245                 250                 255

Glu Trp Glu Ser Asn Gly Gln Pro Glu Asn Asn Tyr Lys Thr Thr Pro
            260                 265                 270

Pro Val Leu Asp Ser Asp Gly Ser Phe Phe Leu Tyr Ser Arg Leu Thr
        275                 280                 285

Val Asp Lys Ser Arg Trp Gln Glu Gly Asn Val Phe Ser Cys Ser Val
    290                 295                 300

Met His Glu Ala Leu His Asn His Tyr Thr Gln Lys Ser Leu Ser Leu
305                 310                 315                 320

Ser Leu Gly Lys
```

<210> SEQ ID NO 8
<211> LENGTH: 323
<212> TYPE: PRT
<213> ORGANISM: Artificial Sequence
<220> FEATURE:
<223> OTHER INFORMATION: Synthetic

<400> SEQUENCE: 8

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Pro Ser Val Phe Leu Phe Pro Pro Lys Pro Lys Asp Thr Leu Met
        115                 120                 125

Ile Ser Arg Thr Pro Glu Val Thr Cys Val Val Val Asp Val Ser Gln
130                 135                 140

Glu Asp Pro Glu Val Gln Phe Asn Trp Tyr Val Asp Gly Val Glu Val
145                 150                 155                 160

His Asn Ala Lys Thr Lys Pro Arg Glu Glu Gln Phe Asn Ser Thr Tyr
                165                 170                 175

Arg Val Val Ser Val Leu Thr Val Leu His Gln Asp Trp Leu Asn Gly
            180                 185                 190

Lys Glu Tyr Lys Cys Lys Val Ser Asn Lys Gly Leu Pro Ser Ser Ile
        195                 200                 205

Glu Lys Thr Ile Ser Lys Ala Lys Gly Gln Pro Arg Glu Pro Gln Val
    210                 215                 220

Tyr Thr Leu Pro Pro Ser Gln Glu Glu Met Thr Lys Asn Gln Val Ser
225                 230                 235                 240

Leu Thr Cys Leu Val Lys Gly Phe Tyr Pro Ser Asp Ile Ala Val Glu
                245                 250                 255

Trp Glu Ser Asn Gly Gln Pro Glu Asn Asn Tyr Lys Thr Thr Pro Pro
            260                 265                 270

Val Leu Asp Ser Asp Gly Ser Phe Phe Leu Tyr Ser Arg Leu Thr Val
        275                 280                 285

Asp Lys Ser Arg Trp Gln Glu Gly Asn Val Phe Ser Cys Ser Val Met
    290                 295                 300

His Glu Ala Leu His Asn His Tyr Thr Gln Lys Ser Leu Ser Leu Ser
305                 310                 315                 320

Leu Gly Lys
```

<210> SEQ ID NO 9
<211> LENGTH: 326
<212> TYPE: PRT
<213> ORGANISM: Artificial Sequence
<220> FEATURE:
<223> OTHER INFORMATION: Synthetic

<400> SEQUENCE: 9

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Cys Pro Ala Pro
                100                 105                 110

Gly Gly Gly Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Leu Gly Lys
                325
```

<210> SEQ ID NO 10
<211> LENGTH: 325
<212> TYPE: PRT
<213> ORGANISM: Artificial Sequence
<220> FEATURE:
<223> OTHER INFORMATION: Synthetic

<400> SEQUENCE: 10

```
Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Gly Gly Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
    130                 135                 140

Ser Gln Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Tyr Arg Val Val Ser Val Leu Thr Val Leu His Gln Asp Trp Leu
            180                 185                 190

Asn Gly Lys Glu Tyr Lys Cys Lys Val Ser Asn Lys Gly Leu Pro Ser
        195                 200                 205

Ser Ile Glu Lys Thr Ile Ser Lys Ala Lys Gly Gln Pro Arg Glu Pro
    210                 215                 220

Gln Val Tyr Thr Leu Pro Pro Ser Gln Glu Glu Met Thr Lys Asn Gln
225                 230                 235                 240

Val Ser Leu Thr Cys Leu Val Lys Gly Phe Tyr Pro Ser Asp Ile Ala
                245                 250                 255

Val Glu Trp Glu Ser Asn Gly Gln Pro Glu Asn Asn Tyr Lys Thr Thr
            260                 265                 270

Pro Pro Val Leu Asp Ser Asp Gly Ser Phe Phe Leu Tyr Ser Arg Leu
        275                 280                 285

Thr Val Asp Lys Ser Arg Trp Gln Glu Gly Asn Val Phe Ser Cys Ser
    290                 295                 300

Val Met His Glu Ala Leu His Asn Arg Phe Thr Gln Lys Ser Leu Ser
305                 310                 315                 320

Leu Ser Leu Gly Lys
            325

<210> SEQ ID NO 11
<211> LENGTH: 324
<212> TYPE: PRT
<213> ORGANISM: Artificial Sequence
<220> FEATURE:
<223> OTHER INFORMATION: Synthetic

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
                100                 105                 110

Gly Gly Pro Ser Val Phe Leu Phe Pro Pro Lys Pro Lys Asp Thr Leu
            115                 120                 125

Met Ile Ser Arg Thr Pro Glu Val Thr Cys Val Val Val Asp Val Ser
130                 135                 140

Gln Glu Asp Pro Glu Val Gln Phe Asn Trp Tyr Val Asp Gly Val Glu
145                 150                 155                 160

Val His Asn Ala Lys Thr Lys Pro Arg Glu Glu Gln Phe Asn Ser Thr
                165                 170                 175

Tyr Arg Val Val Ser Val Leu Thr Val Leu His Gln Asp Trp Leu Asn
                180                 185                 190

Gly Lys Glu Tyr Lys Cys Lys Val Ser Asn Lys Gly Leu Pro Ser Ser
            195                 200                 205

Ile Glu Lys Thr Ile Ser Lys Ala Lys Gly Gln Pro Arg Glu Pro Gln
210                 215                 220

Val Tyr Thr Leu Pro Pro Ser Gln Glu Glu Met Thr Lys Asn Gln Val
225                 230                 235                 240

Ser Leu Thr Cys Leu Val Lys Gly Phe Tyr Pro Ser Asp Ile Ala Val
                245                 250                 255

Glu Trp Glu Ser Asn Gly Gln Pro Glu Asn Asn Tyr Lys Thr Thr Pro
            260                 265                 270

Pro Val Leu Asp Ser Asp Gly Ser Phe Phe Leu Tyr Ser Arg Leu Thr
            275                 280                 285

Val Asp Lys Ser Arg Trp Gln Glu Gly Asn Val Phe Ser Cys Ser Val
            290                 295                 300

Met His Glu Ala Leu His Asn Arg Phe Thr Gln Lys Ser Leu Ser Leu
305                 310                 315                 320

Ser Leu Gly Lys

<210> SEQ ID NO 12
<211> LENGTH: 323
<212> TYPE: PRT
<213> ORGANISM: Artificial Sequence
<220> FEATURE:
<223> OTHER INFORMATION: Synthetic

<400> SEQUENCE: 12

Ala Ser Thr Lys Gly Pro Ser Val Phe Pro Leu Ala Pro Cys Ser Arg
1                   5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys

-continued

```
                85                  90                  95
Arg Val Glu Ser Lys Tyr Gly Pro Pro Cys Pro Pro Cys Pro Ala Pro
            100                 105                 110

Gly Pro Ser Val Phe Leu Phe Pro Pro Lys Pro Lys Asp Thr Leu Met
        115                 120                 125

Ile Ser Arg Thr Pro Glu Val Thr Cys Val Val Val Asp Val Ser Gln
    130                 135                 140

Glu Asp Pro Glu Val Gln Phe Asn Trp Tyr Val Asp Gly Val Glu Val
145                 150                 155                 160

His Asn Ala Lys Thr Lys Pro Arg Glu Glu Gln Phe Asn Ser Thr Tyr
                165                 170                 175

Arg Val Val Ser Val Leu Thr Val Leu His Gln Asp Trp Leu Asn Gly
            180                 185                 190

Lys Glu Tyr Lys Cys Lys Val Ser Asn Lys Gly Leu Pro Ser Ser Ile
        195                 200                 205

Glu Lys Thr Ile Ser Lys Ala Lys Gly Gln Pro Arg Glu Pro Gln Val
    210                 215                 220

Tyr Thr Leu Pro Pro Ser Gln Glu Glu Met Thr Lys Asn Gln Val Ser
225                 230                 235                 240

Leu Thr Cys Leu Val Lys Gly Phe Tyr Pro Ser Asp Ile Ala Val Glu
                245                 250                 255

Trp Glu Ser Asn Gly Gln Pro Glu Asn Asn Tyr Lys Thr Thr Pro Pro
            260                 265                 270

Val Leu Asp Ser Asp Gly Ser Phe Phe Leu Tyr Ser Arg Leu Thr Val
        275                 280                 285

Asp Lys Ser Arg Trp Gln Glu Gly Asn Val Phe Ser Cys Ser Val Met
    290                 295                 300

His Glu Ala Leu His Asn Arg Phe Thr Gln Lys Ser Leu Ser Leu Ser
305                 310                 315                 320

Leu Gly Lys

<210> SEQ ID NO 13
<211> LENGTH: 330
<212> TYPE: PRT
<213> ORGANISM: Homo sapiens

<400> SEQUENCE: 13

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 326
<212> TYPE: PRT
<213> ORGANISM: Homo sapiens

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
                115                 120                 125

Thr Leu Met Ile Ser Arg Thr Pro Glu Val Thr Cys Val Val Val Asp
                130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175
```

Ser Thr Phe Arg Val Val Ser Val Leu Thr Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 15
<211> LENGTH: 327
<212> TYPE: PRT
<213> ORGANISM: Homo sapiens

<400> SEQUENCE: 15

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

```
Glu Pro Gln Val Tyr Thr Leu Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 16
<211> LENGTH: 329
<212> TYPE: PRT
<213> ORGANISM: Artificial Sequence
<220> FEATURE:
<223> OTHER INFORMATION: Synthetic

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Gly Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255
```

```
Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 17
<211> LENGTH: 328
<212> TYPE: PRT
<213> ORGANISM: Artificial Sequence
<220> FEATURE:
<223> OTHER INFORMATION: Synthetic

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Gly Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Asp Glu Leu Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285
```

```
Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Lys
                325
```

<210> SEQ ID NO 18
<211> LENGTH: 327
<212> TYPE: PRT
<213> ORGANISM: Artificial Sequence
<220> FEATURE:
<223> OTHER INFORMATION: Synthetic

<400> SEQUENCE: 18

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320
```

Leu Ser Leu Ser Pro Gly Lys
            325

<210> SEQ ID NO 19
<211> LENGTH: 326
<212> TYPE: PRT
<213> ORGANISM: Artificial Sequence
<220> FEATURE:
<223> OTHER INFORMATION: Synthetic

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 20

<211> LENGTH: 329
<212> TYPE: PRT
<213> ORGANISM: Artificial Sequence
<220> FEATURE:
<223> OTHER INFORMATION: Synthetic

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Gly Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn Arg Phe Thr Gln
305                 310                 315                 320

Lys Ser Leu Ser Leu Ser Pro Gly Lys
                325

<210> SEQ ID NO 21
<211> LENGTH: 328
<212> TYPE: PRT
<213> ORGANISM: Artificial Sequence
<220> FEATURE:
<223> OTHER INFORMATION: Synthetic

<400> SEQUENCE: 21

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Gly Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Asp Glu Leu Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn Arg Phe Thr Gln Lys
305                 310                 315                 320

Ser Leu Ser Leu Ser Pro Gly Lys
                325

<210> SEQ ID NO 22
<211> LENGTH: 327
<212> TYPE: PRT
<213> ORGANISM: Artificial Sequence
<220> FEATURE:
<223> OTHER INFORMATION: Synthetic

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
                    20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn Arg Phe Thr Gln Lys Ser
305                 310                 315                 320

Leu Ser Leu Ser Pro Gly Lys
                325

<210> SEQ ID NO 23
<211> LENGTH: 326
<212> TYPE: PRT
<213> ORGANISM: Artificial Sequence
<220> FEATURE:
<223> OTHER INFORMATION: Synthetic

<400> SEQUENCE: 23

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
```

```
            50                  55                  60
Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
               100                 105                 110

Pro Ala Pro Gly Pro Ser Val Phe Leu Phe Pro Pro Lys Pro Lys Asp
           115                 120                 125

Thr Leu Met Ile Ser Arg Thr Pro Glu Val Thr Cys Val Val Val Asp
       130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Pro Gly Lys
            325

<210> SEQ ID NO 24
<211> LENGTH: 326
<212> TYPE: PRT
<213> ORGANISM: Artificial Sequence
<220> FEATURE:
<223> OTHER INFORMATION: Synthetic

<400> SEQUENCE: 24

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
```

```
                    85                  90                  95
Thr Val Glu Arg Lys Cys Cys Val Glu Cys Pro Pro Cys Pro Ala Pro
                100                 105                 110

Gly Gly Gly Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 25
<211> LENGTH: 325
<212> TYPE: PRT
<213> ORGANISM: Artificial Sequence
<220> FEATURE:
<223> OTHER INFORMATION: Synthetic

<400> SEQUENCE: 25

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Gly Gly Gly Pro Ser Val Phe Leu Phe Pro Pro Lys Pro Lys Asp Thr
```

```
            115                 120                 125
Leu Met Ile Ser Arg Thr Pro Glu Val Thr Cys Val Val Asp Val
    130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ser
                245                 250                 255

Val Glu Trp Glu Ser Asn Gly Gln Pro Glu Asn Asn Tyr Lys Thr Thr
            260                 265                 270

Pro Pro Met Leu Asp Ser Asp Gly Ser Phe Phe Leu Tyr Ser Lys Leu
        275                 280                 285

Thr Val Asp Lys Ser Arg Trp Gln Gln Gly Asn Val Phe Ser Cys Ser
    290                 295                 300

Val Met His Glu Ala Leu His Asn His Tyr Thr Gln Lys Ser Leu Ser
305                 310                 315                 320

Leu Ser Pro Gly Lys
            325

<210> SEQ ID NO 26
<211> LENGTH: 324
<212> TYPE: PRT
<213> ORGANISM: Artificial Sequence
<220> FEATURE:
<223> OTHER INFORMATION: Synthetic

<400> SEQUENCE: 26

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Gly Gly Pro Ser Val Phe Leu Phe Pro Pro Lys Pro Lys Asp Thr Leu
        115                 120                 125

Met Ile Ser Arg Thr Pro Glu Val Thr Cys Val Val Val Asp Val Ser
    130                 135                 140

His Glu Asp Pro Glu Val Gln Phe Asn Trp Tyr Val Asp Gly Val Glu
```

```
145                 150                 155                 160
Val His Asn Ala Lys Thr Lys Pro Arg Glu Glu Gln Phe Asn Ser Thr
                165                 170                 175

Phe Arg Val Val Ser Val Leu Thr Val Val His Gln Asp Trp Leu Asn
                180                 185                 190

Gly Lys Glu Tyr Lys Cys Lys Val Ser Asn Lys Gly Leu Pro Ala Pro
                195                 200                 205

Ile Glu Lys Thr Ile Ser Lys Thr Lys Gly Gln Pro Arg Glu Pro Gln
            210                 215                 220

Val Tyr Thr Leu Pro Pro Ser Arg Glu Glu Met Thr Lys Asn Gln Val
225                 230                 235                 240

Ser Leu Thr Cys Leu Val Lys Gly Phe Tyr Pro Ser Asp Ile Ser Val
                245                 250                 255

Glu Trp Glu Ser Asn Gly Gln Pro Glu Asn Asn Tyr Lys Thr Thr Pro
                260                 265                 270

Pro Met Leu Asp Ser Asp Gly Ser Phe Phe Leu Tyr Ser Lys Leu Thr
                275                 280                 285

Val Asp Lys Ser Arg Trp Gln Gln Gly Asn Val Phe Ser Cys Ser Val
            290                 295                 300

Met His Glu Ala Leu His Asn His Tyr Thr Gln Lys Ser Leu Ser Leu
305                 310                 315                 320

Ser Pro Gly Lys

<210> SEQ ID NO 27
<211> LENGTH: 323
<212> TYPE: PRT
<213> ORGANISM: Artificial Sequence
<220> FEATURE:
<223> OTHER INFORMATION: Synthetic

<400> SEQUENCE: 27

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
                100                 105                 110

Gly Pro Ser Val Phe Leu Phe Pro Pro Lys Pro Lys Asp Thr Leu Met
                115                 120                 125

Ile Ser Arg Thr Pro Glu Val Thr Cys Val Val Val Asp Val Ser His
            130                 135                 140

Glu Asp Pro Glu Val Gln Phe Asn Trp Tyr Val Asp Gly Val Glu Val
145                 150                 155                 160

His Asn Ala Lys Thr Lys Pro Arg Glu Glu Gln Phe Asn Ser Thr Phe
                165                 170                 175

Arg Val Val Ser Val Leu Thr Val Val His Gln Asp Trp Leu Asn Gly
                180                 185                 190
```

Lys Glu Tyr Lys Cys Lys Val Ser Asn Lys Gly Leu Pro Ala Pro Ile
            195                 200                 205

Glu Lys Thr Ile Ser Lys Thr Lys Gly Gln Pro Arg Glu Pro Gln Val
210                 215                 220

Tyr Thr Leu Pro Pro Ser Arg Glu Glu Met Thr Lys Asn Gln Val Ser
225                 230                 235                 240

Leu Thr Cys Leu Val Lys Gly Phe Tyr Pro Ser Asp Ile Ser Val Glu
            245                 250                 255

Trp Glu Ser Asn Gly Gln Pro Glu Asn Asn Tyr Lys Thr Thr Pro Pro
            260                 265                 270

Met Leu Asp Ser Asp Gly Ser Phe Phe Leu Tyr Ser Lys Leu Thr Val
            275                 280                 285

Asp Lys Ser Arg Trp Gln Gln Gly Asn Val Phe Ser Cys Ser Val Met
290                 295                 300

His Glu Ala Leu His Asn His Tyr Thr Gln Lys Ser Leu Ser Leu Ser
305                 310                 315                 320

Pro Gly Lys

<210> SEQ ID NO 28
<211> LENGTH: 326
<212> TYPE: PRT
<213> ORGANISM: Artificial Sequence
<220> FEATURE:
<223> OTHER INFORMATION: Synthetic

<400> SEQUENCE: 28

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Cys Cys Val Glu Cys Pro Pro Cys Pro Ala Pro
        100                 105                 110

Gly Gly Gly Gly Pro Ser Val Phe Leu Phe Pro Pro Lys Pro Lys Asp
    115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
    195                 200                 205

Ala Pro Ile Glu Lys Thr Ile Ser Lys Thr Lys Gly Gln Pro Arg Glu
210                 215                 220

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ser Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Pro Gly Lys
            325

<210> SEQ ID NO 29
<211> LENGTH: 325
<212> TYPE: PRT
<213> ORGANISM: Artificial Sequence
<220> FEATURE:
<223> OTHER INFORMATION: Synthetic

<400> SEQUENCE: 29

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Gly Gly Gly Pro Ser Val Phe Leu Phe Pro Pro Lys Pro Lys Asp Thr
        115                 120                 125

Leu Met Ile Ser Arg Thr Pro Glu Val Thr Cys Val Val Val Asp Val
130                 135                 140

Ser His Glu Asp Pro Glu Val Gln Phe Asn Trp Tyr Val Asp Gly Val
145                 150                 155                 160

Glu Val His Asn Ala Lys Thr Lys Pro Arg Glu Glu Gln Phe Asn Ser
                165                 170                 175

Thr Phe Arg Val Val Ser Val Leu Thr Val Val His Gln Asp Trp Leu
            180                 185                 190

Asn Gly Lys Glu Tyr Lys Cys Lys Val Ser Asn Lys Gly Leu Pro Ala
        195                 200                 205

Pro Ile Glu Lys Thr Ile Ser Lys Thr Lys Gly Gln Pro Arg Glu Pro
    210                 215                 220

Gln Val Tyr Thr Leu Pro Pro Ser Arg Glu Glu Met Thr Lys Asn Gln
225                 230                 235                 240

Val Ser Leu Thr Cys Leu Val Lys Gly Phe Tyr Pro Ser Asp Ile Ser
                245                 250                 255
```

Val Glu Trp Glu Ser Asn Gly Gln Pro Glu Asn Asn Tyr Lys Thr Thr
              260                 265                 270

Pro Pro Met Leu Asp Ser Asp Gly Ser Phe Phe Leu Tyr Ser Lys Leu
          275                 280                 285

Thr Val Asp Lys Ser Arg Trp Gln Gln Gly Asn Val Phe Ser Cys Ser
      290                 295                 300

Val Met His Glu Ala Leu His Asn Arg Phe Thr Gln Lys Ser Leu Ser
305                 310                 315                 320

Leu Ser Pro Gly Lys
              325

<210> SEQ ID NO 30
<211> LENGTH: 324
<212> TYPE: PRT
<213> ORGANISM: Artificial Sequence
<220> FEATURE:
<223> OTHER INFORMATION: Synthetic

<400> SEQUENCE: 30

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Gly Gly Pro Ser Val Phe Leu Phe Pro Pro Lys Pro Lys Asp Thr Leu
        115                 120                 125

Met Ile Ser Arg Thr Pro Glu Val Thr Cys Val Val Val Asp Val Ser
    130                 135                 140

His Glu Asp Pro Glu Val Gln Phe Asn Trp Tyr Val Asp Gly Val Glu
145                 150                 155                 160

Val His Asn Ala Lys Thr Lys Pro Arg Glu Glu Gln Phe Asn Ser Thr
                165                 170                 175

Phe Arg Val Val Ser Val Leu Thr Val Val His Gln Asp Trp Leu Asn
            180                 185                 190

Gly Lys Glu Tyr Lys Cys Lys Val Ser Asn Lys Gly Leu Pro Ala Pro
        195                 200                 205

Ile Glu Lys Thr Ile Ser Lys Thr Lys Gly Gln Pro Arg Glu Pro Gln
    210                 215                 220

Val Tyr Thr Leu Pro Pro Ser Arg Glu Glu Met Thr Lys Asn Gln Val
225                 230                 235                 240

Ser Leu Thr Cys Leu Val Lys Gly Phe Tyr Pro Ser Asp Ile Ser Val
                245                 250                 255

Glu Trp Glu Ser Asn Gly Gln Pro Glu Asn Asn Tyr Lys Thr Thr Pro
            260                 265                 270

Pro Met Leu Asp Ser Asp Gly Ser Phe Phe Leu Tyr Ser Lys Leu Thr
        275                 280                 285

```
Val Asp Lys Ser Arg Trp Gln Gln Gly Asn Val Phe Ser Cys Ser Val
    290                 295                 300

Met His Glu Ala Leu His Asn Arg Phe Thr Gln Lys Ser Leu Ser Leu
305                 310                 315                 320

Ser Pro Gly Lys

<210> SEQ ID NO 31
<211> LENGTH: 323
<212> TYPE: PRT
<213> ORGANISM: Artificial Sequence
<220> FEATURE:
<223> OTHER INFORMATION: Synthetic

<400> SEQUENCE: 31

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Gly Pro Ser Val Phe Leu Phe Pro Pro Lys Pro Lys Asp Thr Leu Met
        115                 120                 125

Ile Ser Arg Thr Pro Glu Val Thr Cys Val Val Val Asp Val Ser His
    130                 135                 140

Glu Asp Pro Glu Val Gln Phe Asn Trp Tyr Val Asp Gly Val Glu Val
145                 150                 155                 160

His Asn Ala Lys Thr Lys Pro Arg Glu Glu Gln Phe Asn Ser Thr Phe
                165                 170                 175

Arg Val Val Ser Val Leu Thr Val Val His Gln Asp Trp Leu Asn Gly
            180                 185                 190

Lys Glu Tyr Lys Cys Lys Val Ser Asn Lys Gly Leu Pro Ala Pro Ile
        195                 200                 205

Glu Lys Thr Ile Ser Lys Thr Lys Gly Gln Pro Arg Glu Pro Gln Val
    210                 215                 220

Tyr Thr Leu Pro Pro Ser Arg Glu Glu Met Thr Lys Asn Gln Val Ser
225                 230                 235                 240

Leu Thr Cys Leu Val Lys Gly Phe Tyr Pro Ser Asp Ile Ser Val Glu
                245                 250                 255

Trp Glu Ser Asn Gly Gln Pro Glu Asn Asn Tyr Lys Thr Thr Pro Pro
            260                 265                 270

Met Leu Asp Ser Asp Gly Ser Phe Phe Leu Tyr Ser Lys Leu Thr Val
        275                 280                 285

Asp Lys Ser Arg Trp Gln Gln Gly Asn Val Phe Ser Cys Ser Val Met
    290                 295                 300
```

```
His Glu Ala Leu His Asn Arg Phe Thr Gln Lys Ser Leu Ser Leu Ser
305                 310                 315                 320

Pro Gly Lys
```

HEAVY CHAIN CONSTANT REGIONS WITH REDUCED BINDING TO FC GAMMA RECEPTORS

CROSS-REFERENCE TO RELATED APPLICATIONS

This application is a continuation of U.S. application Ser. No. 15/562,881, filed Sep. 28, 2017, which is a § 371 US national stage of PCT/US2016/025051, filed Mar. 30, 2016, which claims the benefit under 35 USC 119(e) of U.S. Provisional Application No. 62/140,350, filed Mar. 30, 2015, each of which is incorporated by reference in its entirety for all purposes.

FIELD OF THE INVENTION

The present invention resides in the field of recombinant protein engineering, and relates to optimized hinge variants of immunoglobulin (Ig) proteins, methods of engineering such Ig variants and suitability of such Ig variants in biopharmaceutical practice.

REFERENCE TO A SEQUENCE LISTING

This application incorporates by reference a sequence listing submitted in computer readable form as file 10140US02-Sequence.txt, created on Dec. 19, 2019, and containing 78,858 bytes.

BACKGROUND

Antibodies of the IgG class are attractive therapeutic agents. IgGs exist as four subclasses in humans, IgG1, IgG2, IgG3, and IgG4. The heavy chain constant (CH) region of IgG comprises three domains, CH1, CH2, CH3, and a hinge linking CH1 and CH2. Although the role of each subclass appears to vary between species, the heavy chain constant domain is responsible for various biological effector functions. The human IgG subclasses mediate several cellular immune responses through their interaction with Fcγ (FcγRs), such as cell killing, phagocytosis and opsonization. Such interaction involves binding of at least functional CH2 and CH3 domains of a heavy chain constant region to an FcγR on the surface of an effector cell, such as a natural killer cell, an activated macrophage or the like. Complement-mediated lysis can also be triggered by the interaction of the Fc region with various complement components.

Effector functions are useful in some antibody therapies, such as treatment of some cancers or pathogens, in which effector function is primarily or at least partially responsible for killing cancer cells or the pathogen. However, other antibody therapies are mediated entirely or predominantly by effector-independent mechanisms, such as inhibiting a receptor-ligand interaction or agonizing a receptor. In such therapies, antibody effector functions serve little or no useful purpose but can result in undesired inflammation. In such circumstances, it may be advantageous to engineer the Fc receptor binding properties of an antibody so as to inhibit some or all of the available effector mechanisms, without substantially affecting the antibody's pharmacokinetic properties, immunogenicity and variable regions specificity and affinity.

IgG heavy chain constant regions have been mutated in various positions to test the effect of amino acids on IgG/FcγR interaction (see e.g. Canfield and Morrison, J Exp Med 73, 1483-1491 (1991); Chappel et al. JSC 268(33), 25124-31 (1993); and Armour et al., Eur. J. Immunol. 29, 2613-24 (1999)). Several amino acid residues in the hinge region and in the CH2 domain of a heavy chain constant region have been proposed as mediating binding to Fcγ receptors (see Sarmay et al., Mol Immunol 29, 633-9 (1992); Greenwood et al., Eur. J. Immunol, 23(5), 1098 (1993), Morgan et al., Immunology 86, 319 (1995), Stevenson, Chemical Immunology, 65, 57-72 (1997)). Glycosylation of a site (N297) in the CH2 domain and variations in the composition of its carbohydrates also strongly affect the IgG/FcγR interaction (Stevenson, Chemical Immunology, 65, 57-72 (1997); Siberil et al, Immunol. Ltrs. 106, 111-118 (2006)).

Alanine residues have usually been the preferred substituent for replacing a natural amino acid with an unnatural one so as to reduce function because alanine has a side chain without any functional groups. For example, the well-known technique of alanine-scanning mutagenesis systematically replaces every natural residue in a protein or protein domain with alanine to identify which natural residues contribute primarily to function. Replacing an amino acid with a functional group with alanine eliminates the functional group and its contribution to binding to any receptor, but the presence of the alanine side chain substantially preserves conformation, reducing the potential for immunogenicity or other complexities due to conformational changes. An alternative strategy replaces amino acids in the hinge region of one IgG isotype with corresponding amino acids from human IgG2 isotype so as to reduce FcγR binding without unacceptable conformational changes and consequent immunogenicity. The resulting chimeric Fc-containing antibodies include a substitution of EFLG at positions 232-236 with PVA (see WO14/121087).

SUMMARY OF THE CLAIMED INVENTION

The invention provides an immunoglobulin heavy chain comprising a constant region, wherein positions 233-236 within a hinge domain are G, G, G and unoccupied; G, G, unoccupied, and unoccupied; G, unoccupied, unoccupied, and unoccupied; or all unoccupied, with positions numbered by EU numbering. Optionally, the immunoglobulin heavy chain of claim 1 that is human IgG4 isotype. Optionally, positions 226-229 are CPPC. Optionally, the hinge domain amino acid sequence comprises CPPCPAPGGG-GPSVF (SEQ ID NO:1), CPPCPAPGG--GPSVF (SEQ ID NO:2), CPPCPAPG---GPSVF (SEQ ID NO:3), or CPPCPAP----GPSVF (SEQ ID NO:4). Optionally, the constant region has an amino acid sequences comprising SEQ ID NO:5, 6, 7 or 8 or a variant thereof having up to five insertions deletions, substitutions or insertions. Optionally, the constant region comprises SEQ ID NO: 5, 6, 7 or 8. Optionally, the constant region consists of SEQ ID NO: 5, 6, 7 or 8. Optionally, the immunoglobulin heavy chain comprises from N-terminal to C-terminal the hinge domain, a CH2 domain and a CH3 domain. Optionally, the immunoglobulin heavy chain comprises from N-terminal to C-terminal a CH1 domain, the hinge domain, a CH2 domain and a CH3 domain. Optionally, the CH1 region, if present, remainder of the hinge region, if any, CH2 region and CH3 region are the same human isotype. Optionally, the CH1 region, if present, remainder of the hinge region, if any, CH2 region and CH3 region are human IgG1. Optionally, the CH1 region, if present, remainder of the hinge region, if any, CH2 region and CH3 region are human IgG2. Optionally, the CH1 region if present, remainder of the hinge region, if any, CH2 region and CH3 region are human IgG4. Optionally, the constant region has a CH3 domain modified to reduce binding to protein A. Optionally, the immunoglobulin heavy chain of any preceding claim linked at the N-terminus to a heavy chain variable region. Optionally, the immunoglobulin heavy chain is duplexed with an immunoglobulin light chain. Optionally, the immunoglobulin heavy chain is duplexed with an immunoglobulin light chain as a heterodimer comprising two immunoglobulin heavy chains and two light chains. The two heavy chains can be the same or different. Optionally, the immunoglobulin heavy chain of any preceding claim linked at the N-terminus to a binding polypeptide. Optionally, the immunoglobulin heavy chain is linked via a linker to the binding polypeptide. Optionally, the binding polypeptide is an extracellular domain.

BRIEF DESCRIPTION OF FIGURES

FIG. 1 shows correspondence of numbering schemes in the hinge region of human IgG1, IgG2, and IgG4.

FIGS. 2-4 show the wild-type sequences of heavy chain constant regions of isotypes IgG1, IgG2, IgG3 and IgG4 with delineation into CH1, hinge, CH2 and CH3 regions.

FIG. 5 is a schematic showing exemplary hinge-modified GGG-(233-236), GG--(233-236), G---(233-236) and no_G (233-236) replacement formats compared with a previously described chimeric heavy chain constant region, all of human IgG4 isotype.

FIGS. 6-10 show binding of various hinge-modified antibodies of human IgG4 isotype (and wild-type IgG1 isotype antibody) to human FcγRI, FcγRIIA, FcγRIIB, FcγRIIIA, and FcRn.

FIGS. 12A-D show that various hinge-modified antibodies show no significant activation of Jurkat cells with a luciferase marker when the activation is dependent on anchoring of the antibody to HEK cells transformed with FcγRIIA (FIG. 12A, FIG. 12B) or RIIB (FIG. 12C, FIG. 12D). The activation by the positive control antibody in FIG. 12A and FIG. 12C is greatly reduced on competition with a blocking antibody, as in FIG. 12B and FIG. 12D.

FIG. 13 shows hinge-modified antibodies activating Jurkat cells with a luciferase marker when the antibodies are anchored to a plate surface instead of by attempted binding to an FcγRIIA or RIIB receptor on the HEK cells.

FIG. 14 shows hinge-modified antibodies having variable regions that bind CD20 display reduced antibody-dependent cellular cytotoxicity (ADCC) in the presence of NK cells cells engineered to express the higher affinity V allele of FcγRIIIa and CD20-expressing Daudi cells.

DEFINITIONS

Figure 11A:
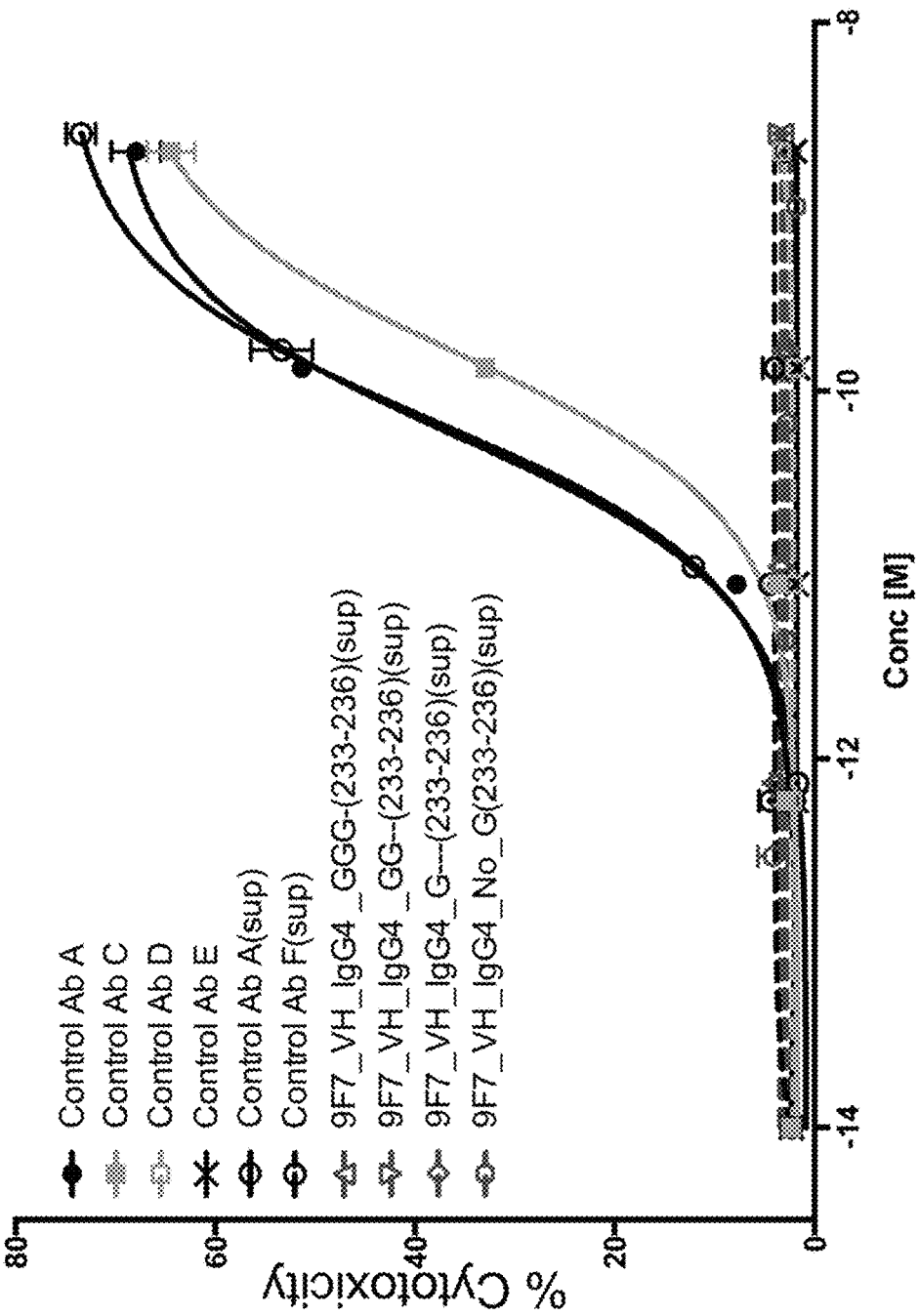
FIG. 11A shows hinge-modified antibodies (as recovered from cell culture supernatants) are unable to recruit human T-cells to lyse U937 cells, which bear FcγRI and FcγRIIA.

Antibodies or fusion proteins are typically provided in isolated form. This means that an antibody or fusion protein is typically at least 50% w/w pure of interfering proteins and other contaminants arising from its production or purification but does not exclude the possibility that an antibody or fusion protein is combined with an excess of pharmaceutical acceptable carrier(s) or other vehicle intended to facilitate its use. Sometimes antibodies or fusion proteins are at least 60, 70, 80, 90, 95 or 99% w/w pure of interfering proteins and contaminants from production or purification. Often an antibody or fusion protein is the predominant macromolecular species remaining after its purification.

A basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region means a light chain variable region without the light chain signal peptide. However, reference to a variable region does not mean that a signal sequence is necessarily present; and in fact signal sequences are cleaved once the antibodies or fusion proteins of the invention have been expressed and secreted. A pair of heavy and light chain variable regions defines a binding region of an antibody. The carboxy-terminal portion of the light and heavy chains respectively defines light and heavy chain constant regions. The heavy chain constant region is primarily responsible for effector function. In IgG antibodies, the heavy chain constant region is divided into CH1, hinge, CH2, and CH3 regions. In IgA, the heavy constant region is divided into CH1, CH2 and CH3. The CH1 region binds to the light chain constant region by disulfide and noncovalent bonding. The hinge region provides flexibility between the binding and effector regions of an antibody and also provides sites for intermolecular disulfide bonding between the two heavy chain constant regions in a tetramer subunit. The CH2 and CH3 regions are the primary site of effector functions and FcRn binding.

Light chains are classified as either kappa or lambda. Heavy chains are classified as γ, mu, alpha, delta, or epsilon, and define the antibody's isotype as IgG, IgM, IgA, IgD and IgE, respectively. Within light and heavy chains, the variable and constant regions are joined by a "J" segment of about 12 or more amino acids, with the heavy chain also including a "D" segment of about 10 or more amino acids. (See generally, *Fundamental Immunology* (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites, i.e., is divalent. In natural antibodies, the binding sites are the same. However, bispecific antibodies can be made in which the two binding sites are different (see, e.g., Songsivilai and Lachmann, Clin. Exp. Immunol., 79:315-321 (1990); Kostelny et al., J. Immunol., 148:1547-53 (1992)). The variable regions all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989). Kabat also provides a widely used numbering convention (Kabat numbering) in which corresponding residues between different heavy chain variable regions or between different light chain variable regions are assigned the same number. Although Kabat numbering can be used for antibody constant regions, the EU index is more commonly used, as is the case in this application.

An antibody or fusion protein of the invention is monospecific if all of its antigen (or ligand) binding regions have the same specificity. An antibody or fusion protein is multispecific if its antigen binding regions include at least two different specificities.

A hinge is a region of consecutive amino acid residues that connect the C-terminus of the $C_H1$ to the N-terminus of the $C_H2$ domain of an immunoglobulin. In human IgG1, IgG2 and IgG4, the hinge region runs from residue 216 to 236 by EU numbering. Residues 231-236 form a lower hinge and residues 216 to 230 form an upper and middle (or core) hinge. The demarcation between upper and middle varies by isotype. The upper and middle hinges of IgG1, IgG2 and IgG4 are 12-15 consecutive amino acids encoded by a distinct hinge exon. The lower hinge includes several N-terminal amino acids of the $C_H2$ domain (encoded by the $C_H2$ exon) (Brekkeet al. Immunology Today 16(2):85-90 (1995)). IgG3 comprises a hinge region consisting of four segments: one upper segment resembling the hinge region of IgG1, and 3 segments that are identical amino acid repeats unique to IgG3.

The term "antibody" includes any form of antibody with at least one binding region including monovalent fragments, divalent tetrameric units of two heavy chains and light chains, and higher order complexes of any of these. An antibody can be mono-specific in which case all binding regions have the same specificity or multi-specific in which the binding sites have at least two specificities. Antibody fragments typically include a heavy chain variable region and a heavy chain constant region and may also include a light chain variable region. For example, an antibody fragment can include from N-terminal to C-terminal a light chain variable region, a peptide spacer, a heavy chain variable region and a heavy chain constant region of the invention. Another fragment includes a heavy chain variable region (the binding region) and a heavy chain constant region and no light chain (i.e., a Dab or nanobody). Likewise, a fusion protein includes a monomeric or dimeric fusion protein unit, or higher order complexes.

A "monoclonal antibody" refers to a preparation of antibody molecules resulting from propagation of a single clone consisting essentially of the same antibody molecules. Minor differences resulting from spontaneous mutations arising in culture or posttranslational processing may be present. A monoclonal antibody composition displays a single binding specificity and affinity for a particular epitope. Accordingly, the term "mouse or murine monoclonal antibody" refers to antibodies displaying a single binding specificity which have variable and constant regions derived from murine or mouse germline immunoglobulin sequences.

A multispecific antibody typically comprises multiple different variable domains (two in the case of bispecific antibody), wherein each variable domain is capable of specifically binding to a separate antigen or to a different epitope on the same antigen. Exemplary bispecific formats that can be used with disclosed constant regions include e.g., scFv-based bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, dual acting Fab (DAF)-IgG, and Mab2 bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al. 2013, J. Am. Chem. Soc. 9; 135(1):340-6 [Epub: Dec. 21, 2012]). Another exemplary multispecific format that can be used with the disclosed constant regions includes a first antigen-binding domain that specifically binds a target molecule, and a second antigen-binding domain that specifically binds an internalizing effector protein, wherein such second antigen-binding domains are capable of activating and internalizing the effector protein, e.g. a receptor. (See US 2013/0243775A1.).

Binding refers to an interaction between at least two entities, or molecular structures, such as an antibody-antigen interaction, or an Fc-containing protein to an FcγR (wherein the Fc-containing protein is an antibody, Ig, antibody-binding fragment, or Fc-fusion protein, e.g. receptor-Fc fusion). For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIAcore 3000 instrument using the antigen or FcR as the ligand and the antibody, Ig, antibody-binding fragment, or Fc-containing protein as the analyte (or antiligand). Accordingly, an antibody or fusion protein binds to a target antigen or receptor with an affinity corresponding to a $K_D$ value that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein). There is an inverse relationship between $K_D$ and binding affinity, therefore the smaller the $K_D$ value, the higher the affinity. Thus, the term "lower affinity" relates to a lower ability to form an interaction and therefore a larger $K_D$ value.

An epitope is an antigenic determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former, but not the latter, is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specific antigen binding peptide (in other words, the amino acid residue is within the footprint of the specific antigen binding peptide).

A humanized antibody is a genetically engineered antibody in which the CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539, Carter, U.S. Pat. No. 6,407,213, Adair, U.S. Pat. Nos. 5,859,205 6,881,557, Foote, U.S. Pat. No. 6,881,557). The acceptor antibody sequences can be, for example, a mature human antibody sequence, a composite of such sequences, a consensus sequence of human antibody sequences, or a germline region sequence. Thus, a humanized antibody is an antibody having some or all CDRs entirely or substantially from a donor antibody and variable region framework sequences and constant regions, if present, entirely or substantially from human antibody sequences. Similarly a humanized heavy chain has at least one, two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least one, two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized antibody is substantially from a corresponding CDR in a non-human antibody when at least 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 85, 90, 95 or 100% of corresponding residues defined by Kabat are identical.

Although humanized antibodies often incorporate all six CDRs (preferably as defined by Kabat) from a mouse antibody, they can also be made with less than all CDRs (e.g., at least 3, 4, or 5 CDRs from a mouse antibody) (e.g., Pascalis et al., J. Immunol. 169:3076, 2002; Vajdos et al., Journal of Molecular Biology, 320: 415-428, 2002; Iwahashi et al., Mol. Immunol. 36:1079-1091, 1999; Tamura et al, Journal of Immunology, 164:1432-1441, 2000).

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

A human antibody refers to antibodies having variable and constant regions derived from human germline immunoglobulin sequences. Such an antibody can be one produced by a human or human B-cells, or a transgenic mouse bearing human immunoglobulin genes, or by from a phage display, retroviral display, ribosomal display and the like (see for instance Hoogenboom et al., J. Mol. Biol. 227, 381 (1991) (phage display), Vaughan et al., Nature Biotech 14, 309 (1996) (phage display), Hanes and Plucthau, PNAS USA 94, 4937-4942 (1997) (ribosomal display), Parmley and Smith, Gene 73, 305-318 (1988) (phage display), Scott TIBS 17, 241-245 (1992), Cwirla et al., PNAS USA 87, 6378-6382 (1990), Russell et al., Nucl. Acids Research 21, 1081-1085 (1993), Hogenboom et al., Immunol. Reviews 130, 43-68 (1992), Chiswell and McCafferty, TIBTECH 10, 80-84 (1992), and U.S. Pat. No. 5,733,743). Human antibodies can include amino acid residues not encoded by human germline immunoglobulin introduced by maturation in vivo, such as by somatic mutation or gene rearrangement in vivo. Human antibodies can also include a small number of mutations (e.g., up to 10 per heavy or light chain) introduced by random or site-specific mutagenesis in vitro).

A transgenic animal for producing human antibodies refers to a non-human animal having a genome comprising one or more human heavy and/or light chain transgenes or transchromosomes (either integrated or non-integrated into the animal's natural genomic DNA) and which is capable of expressing fully human antibodies or at least antibodies with fully human variable regions. For example, a transgenic mouse can have a human light chain transgene and either a human heavy chain transgene or human heavy chain transchromosome, such that the mouse produces human antibody when immunized with target antigen and/or cells expressing the target antigen. The human heavy chain transgene may be integrated into the chromosomal DNA of the mouse, as is the case for transgenic mice, for instance HuMAb mice, such as HCo7 or HCol2 mice, or the human heavy chain transgene may be maintained extrachromosomally, as is the case for transchromosomal KM mice as described in WO02/43478. Such transgenic and transchromosomal mice (collectively referred to as "transgenic mice") are capable of producing multiple isotypes of human monoclonal antibodies to a given antigen (such as IgG, IgA, IgM, IgD and/or IgE) by undergoing V-D-J recombination and isotype switching. VELOCIMMUNE® genetically engineered mice comprise a replacement of unrearranged V(D)J gene segments at endogenous mouse loci with human V(D)J gene segments. VELOCIMMUNE® mice express chimeric antibodies having human variable domains and mouse constant domains (see, e.g., U.S. Pat. No. 7,605,237). Most other reports concern mice that express fully human antibodies from fully human transgenes in mice that have disabled endogenous immunoglobulin loci. The VELOCIMMUNE® mouse includes, in part, having a genome comprising human variable regions operably linked to endogenous mouse constant region loci such that the mouse produces antibodies comprising a human heavy chain variable region and a mouse heavy chain constant region in response to antigenic stimulation. The DNA encoding the variable regions of the heavy chains of the antibodies can be isolated and operably linked to DNA encoding the human heavy chain constant regions of the invention. The DNA can then be expressed in a cell capable of expressing the fully human heavy chain of the antibody.

Several antibody effector functions are mediated at least in part by Fc receptors (FcRs), which bind the Fc region of an antibody in the constant domain (specifically, the CH2 and CH3 domain) of a typical immunoglobulin. There are a number of Fc receptors which are specific for the different classes of immunoglobulins, i.e. IgG, IgE, IgA, IgM, and IgD. The human IgG Fc receptor family is divided into three groups: FcγRI (CD64), which is capable of binding IgG with high affinity, FcγRII (CD32) and FcγRIII (CD16) both of which are low affinity receptors. Each FcγR subclass is encoded by two or three genes, and alternative RNA splicing leads to multiple transcripts, hence, a broad diversity in FcγR isoforms exists (e.g. FcγRIA (CD64; FCGR1A, Swiss Prot P12314), FcγRIB (CD64; FCRG1 B), FcγRIIA (CD32; FCGR2A, Swiss Prot P12318), FcγRIIB (CD32; FCGR2B, Swiss Prot P31994), FcγRIIC (CD32; FCGR2C), FcγRIIIA (CD16a; FCGR3A, Swiss Prot P08637), and FcγRIIIB (CD16b; FCGR3B)). Furthermore, Fc receptors are expressed on a variety of cells, including, e.g., B cells, monocytes, dendritic cells, neutrophils, and certain lymphocytes. For example, U937 cells, a human monocyte cell line, express both FcγRI and FcγRIIA (see e.g., Jones, et al. J Immunol 135(5):3348-53 (1985); and Brooks, et al. J Exp Med 170:1369-85 (October 1989)).

Antibody-dependent cellular cytotoxicity or ADCC is an activity to damage a target cell when an Fcγ receptor-bearing cell (an immune cell or the like) binds to an Fc portion of a specific antibody through the Fcγ receptor, when the specific antibody has attached to a cell-surface antigen of the target cell. Thus, ADCC is a mechanism by which Fc receptor-positive effector cells can lyse target cells that have adherent antigen-specific molecule. The ADCC activity can be evaluated by for example measuring the fluorescent intensity using a fluorescent dye such as calcein AM (Wako Pure Chemical Industries, Ltd., 349-07201). When this approach is employed, the cytotoxic activity (% cell lysis) can be calculated, using the obtained values, according to the equation: (A−C)/(B−C)×100, wherein A is a fluorescent value in each sample, B is an average fluorescent value of the cells lysed and released into a medium with Nonidet P-40 having a final concentration of 1%, and C is an average fluorescent value when only the medium was added.

"Antibody-dependent cellular phagocytosis" or "ADCP" relates to effector function that eliminates (or kills) a target cell by engulfing the target cell rather than inducing cytolysis. ADCP may be an important in vivo mechanism for killing tumor cells. ADCP can be measured by two-color fluorescence flow cytometry methods, for example methods utilizing, e.g. PKH2 (green fluorescent dye) and phycoerythrin-conjugated (red) monoclonal antibodies against different cell surface proteins to differentiate the test cells, thus determining phagocytic activity and rate of phagocytosis. Therapeutic strategies that selectively activate FcγRIIa relative to FcγRIIb may enhance macrophage phagocytic activity (Richards et al. 2008 Mol. Cancer Ther. 7(8):2517-27).

Complement-directed cytotoxicity or CDC refers to cytotoxic activity by the complement system. CDC activity can be measured, for example the target cells, antibody, and complement solution (such as baby rabbit complement (Cedarlane Technologies)) are incubated and are allowed to react, according to standard protocols (NIAID Manual of Tissue Typing Techniques 1979-1980, Edited by J. G. Ray, NIH Publication No. NIH-83-545.) The cytotoxic activity can be calculated in the same manner as the measurement of the ADCC activity. The cytotoxic activity can also be measured using a fluorescent dye (such as calcein) or radioactive dyes similarly to the above with respect to ADCC.

The term "subject" includes human and other mammalian subjects that receive either prophylactic or therapeutic treatment.

Compositions or methods "comprising" one or more recited elements may include other elements not specifically recited. For example, a composition that comprises antibody may contain the antibody alone or in combination with other ingredients.

DETAILED DESCRIPTION

I. General

The invention provides antibody heavy chain constant regions with a hinge region modified to reduce binding to Fcγ receptors. The modification occurs within positions 233-236 by EU numbering by replacement of natural residues by glycine(s) and/or deletion(s). The inventors unexpectedly found that such modifications in the hinge region of antibodies can usefully reduce binding of such antibodies to Fcγ receptors to a greater extent than previous modifications in this region, and particularly can reduce binding to background levels for any or all of FcγRI, FcγRIIA, FcγRIIB, and FcγRIIIA. These modified immunoglobulin constant regions can be incorporated into virtually any format of antibody or Fc fusion protein. Such antibodies or fusion proteins can be used in methods of treatment, particularly those in which the mechanisms of action of the antibody or Fc fusion protein is not primarily or at all dependent on effector functions, as is the case when an antibody inhibits a receptor-ligand interaction or agonizes a receptor.

II. Heavy Chain Constant Regions

Figure 1:
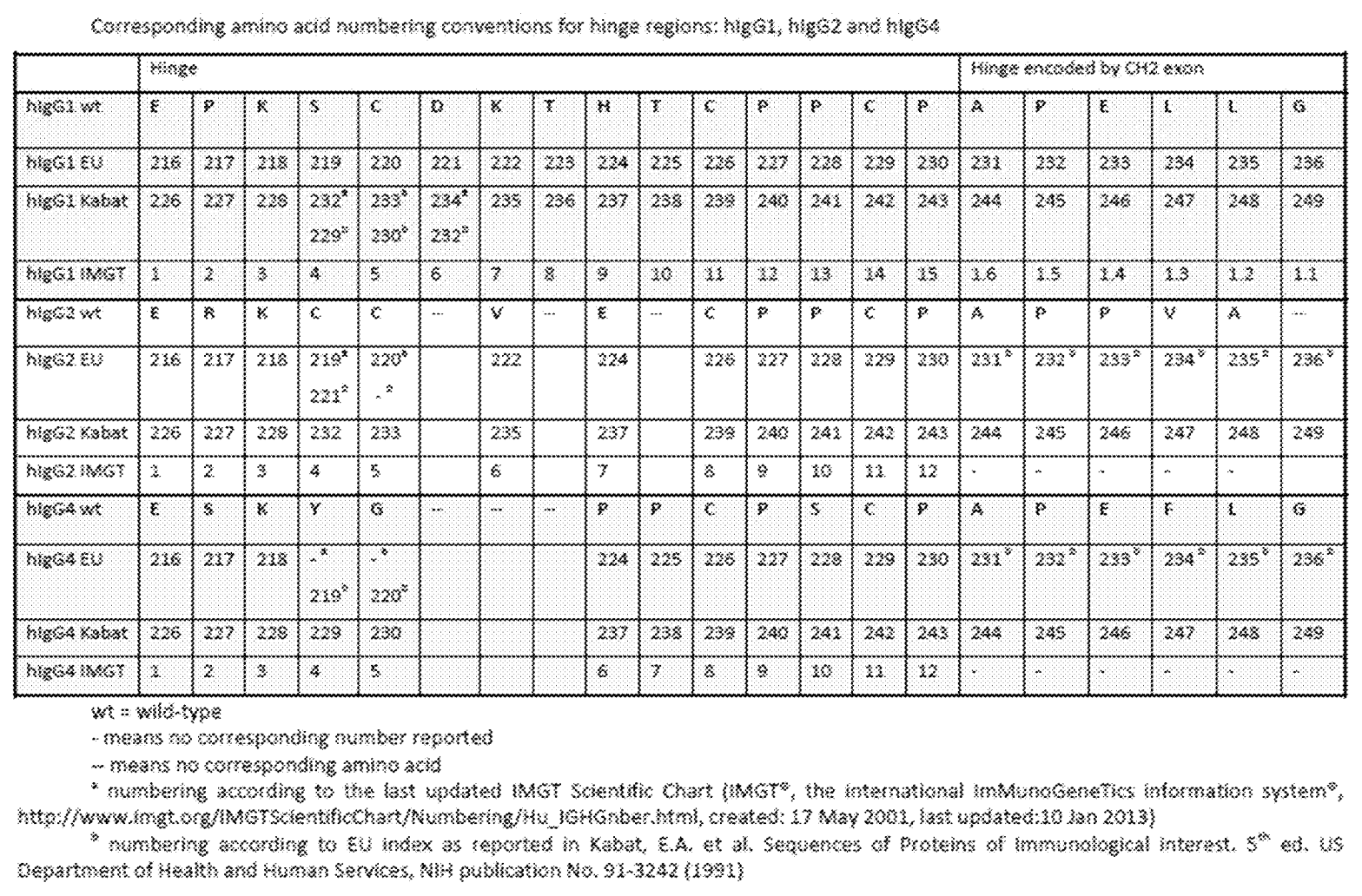

The invention provides modified immunoglobulin heavy chain regions in which each of positions 233-236 by EU number is occupied by G or is unoccupied. Position 236 is unoccupied in canonical human IgG2 but is occupied by in other canonical human IgG isotypes. Positions 233-235 are occupied by residues other than G in all four human isotypes (see FIG. 1). Position 233 is not believed to interact directly with Fcγ receptors but was included in the mutagenesis because removing replacing the wildtype glu residue in IgG1 and IgG4 or pro residue in IgG2 in combination with the other mutations would reduce immunogenicity. In four exemplary modified constant regions, positions 233-236 are gly gly gly unoccupied, gly gly unoccupied, unoccupied; gly, unoccupied, unoccupied, unoccupied and all unoccupied (see FIG. 5). These segments can be represented as GGG-, GG--, G--- or ---- with "-" representing an unoccupied position.

The hinge modification within positions 233-236 can be combined with position 228 being occupied by P. Position 228 is naturally occupied by P in human IgG1 and IgG2 but is occupied by S in human IgG4 and R in human IgG3. An S228P mutation in an IgG4 antibody is advantageous in stabilizing an IgG4 antibody and reducing exchange of heavy chain light chain pairs between exogenous and endogenous antibodies.

Preferably positions 226-229 are occupied by C, P, P and C respectively.

Exemplary hinge regions have residues 226-236, sometimes referred to as middle (or core) and lower hinge, occupied by the modified hinge sequences designated GGG-(233-236), GG--(233-236), G---(233-236) and no G(233-236).

```
hIgG1           CPPCPAPELLGGPSVF hIgG2           CPPCPAPPVA-GPSVF hIgG4           CPSCPAPEFLGGPSVF

GGG-(233-236)   CPPCPAPGGG-GPSVF   (SEQ ID NO: 1)

GG--(233-236)   CPPCPAPGG--GPSVF   (SEQ ID NO: 2)

G---(233-236)   CPPCPAPG---GPSVF   (SEQ ID NO: 3)

no_G(233-236)   CPPCPAP----GPSVF   (SEQ ID NO: 4)
```

The modified hinge regions described above can be incorporated into a heavy chain constant region, which typically include CH2 and CH3 domains, and which may have an additional hinge segment (e.g., an upper hinge) flanking the designated region, and a CH1 region. Such additional constant region segments present are typically of the same isotype, preferably a human isotype, although can be hybrids of different isotypes. The isotype of such additional human constant regions segments is preferably human IgG4 but can also be human IgG1, IgG2, or IgG3 or hybrids thereof in which domains are of different isotypes. Exemplary sequences of human IgG1, IgG2 and IgG4 are shown in FIGS. 2-4. A constant region is considered to be of a designated isotype if it differs from that isotype by no more than 1, 2, 3, 4, 5, 6, 7, 8, 9 or 10 substitutions, deletions or internal insertions, except however, that the CH1 domain can be omitted entirely as can the upper hinge region. CH1, CH2 and CH3 domains are considered to be of IgG1, IgG2 or IgG4 isotype if differing from the CH1, CH2 and CH3 region of the exemplified sequence by no more than 1, 2, 3, 4 or 5 substitutions, deletions or internal insertions. The remainder of a hinge outside the 226-236 region sequences presented above is considered to be of IgG1, IgG2 or IgG4 isotype if it differs from the corresponding part of the hinge region of the exemplified hinge sequences by no more than 1 or 2 substitutions, deletions or internal insertions.

Some preferred heavy chain constant regions have amino acid sequences consisting or comprising SEQ ID NO. 5, 6, 7 and 8. These heavy chain constant regions incorporate the segments SEQ ID NO:1, SEQ ID NO:2, SEQ ID:3 and SEQ ID NO:4 at residues 226-236 shown above in an otherwise-human IgG4 isotype. Other preferred constant regions differ from the designated SEQ ID NO. at up to 1, 2, 3, 4,5, 6, 7, 8, 9 or 10 positions but retain at least GGG-, GG--, G--- or ----- at EU positions 232-236 and P at position 228 and preferably retain of residues 226-236 shown above for SEQ ID NO:1, SEQ ID NO:2, SEQ ID:3 and SEQ ID NO:4. Variations from the designated SEQ ID NOS. can represent one or several natural allotypic or isoallotypic variations, variations to increase or reduce an effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004), for which exemplary substitutions include a Gln at position 250 and/or a Leu at position 428 (EU numbering. Other variations can add or remove sites of post-translational modification, such as N-linked glycosylation at N-X-S/T motifs. Variations can also include introduction of knobs (i.e., replacement of one or more amino acids with larger amino acids) or holes (i.e., replacement of one or more amino acids with smaller amino acids) to promote formation of heterodimers between different heavy chains for production of bispecific antibodies. Exemplary substitutions to form a knob and hole pair are T336Y and Y407T respectively (Ridgeway et al., Protein Engineering vol. 9 no. 7 pp. 617-621, 1996). Variations can also include mutations that reduce protein A interaction (e.g., H435R and Y436F) in the EU numbering system. Bispecific antibodies in which one heavy chain has such a variation, and another does not, can be separated from their parental antibodies by protein-A affinity chromatography. For example, SEQ ID NOS. 9-12 are the same as SEQ ID NOS. 5-8 except for the presence of H435R and Y436F mutations. One or more residues from the C-terminus of constant regions, particularly a C-terminal lysine on the heavy chain, can be lost as a result of post-translational modification.

Other heavy chain constant regions comprise or consist of SEQ ID NOS. 16-19 and 20-23, which correspond to SEQ ID NOS. 5-8 and 9-12 respectively except that the former are of human IgG1 rather than IgG4 isotype. Other heavy chain constant regions comprise or consist of SEQ ID NOS. 24-27 and 28-31, which correspond to SEQ ID NOS. 5-8 and 9-12 respectively except the former are of human IgG2 rather than IgG4 isotype.

Other preferred constant regions differ from any of the above designated SEQ ID NO. at up to 1, 2, 3, 4, 5, 6, 7, 8, 9 or 10 positions but retain at least GGG-, GG--, G--- or ----- at EU positions 232-236 and P at position 228 and preferably retain residues 226-236 shown above for SEQ ID NO:1, SEQ ID NO:2, SEQ ID:3 and SEQ ID NO:4 in the same manner as was discussed for IgG4 isotype constant regions.

Modified constant regions and antibodies or fusion proteins incorporating such constant regions are characterized by reduced affinity for Fcγ receptors compared with isotype matched controls (wildtype constant regions or antibodies or fusion proteins incorporating the same). Binding affinity (Ka) is preferably reduced at least 90, 95 or 99% compared with the isotype matched controls. Preferably binding affinity is reduced to background levels (i.e., same signal within experimental error as in a control reaction with an sc-Fv fragment lacking any constant region or in which an irrelevant receptor is used in place of Fcγ. Preferably, affinity is reduced to a background level or at least 90, 95 or 99% for each of human Fcγ receptors, γRI, γRIIA, γRIIB and γRIIIA.

Likewise, effector functions dependent on Fcγ receptor binding, such as ADCC or ADCP are reduced, preferably by at least 90, 95 or 99% or more preferably to background level. Such functions include cell killing or phagocytosis, B-cell activation, and release of inflammatory mediators, such as cytokines. Some such effects can be quantified by measurement of EC50, which refers to the half maximal effective concentration of an antibody which induces a response halfway between the baseline and maximum after a specified exposure time. The $EC_{50}$ essentially represents the concentration of an antibody where 50% of its maximal effect is observed. Some antibodies or fusion proteins including a modified heavy chain constant region of the invention show cytotoxicity of less than 20% cytolysis (i.e. % cytotoxicity), or less than 10%, or 5%, 4%, 3%, 2%, or even 0% or undetectable cytolysis (cytotoxicity), as measured in an in vitro or ex vivo cell killing assay compared with suitable isotype-matched control antibodies with a wildtype constant region, optionally, measured at an antibody or fusion protein concentration of 10 nM.

However, binding affinity of an antibody or fusion protein incorporating such a heavy chain constant region is preferably not substantially affected by the modified constant region. That is, the binding affinity is typically the same within experimental error or at least within a factor of 2 or 3 of a suitable control antibody with a isotype-matched wild type constant region. The same is the case for functional properties not dependent on FcγR binding, such as ability to inhibit receptor-ligand binding (e.g., EC50), or ability to agonize a receptor.

Immunogenicity of modified constant regions or antibodies or fusion proteins incorporated modified constant regions compared with isotype matched controls can be assessed in vitro from dendrocyte maturation or T-cell proliferation on challenge (Gaitonde et al., Methods Mol. Biol. 2011; 716: 267-80) or in vivo by comparing incidence of reactive antibodies against administered antibodies between populations. The immunogenicity of modified constant regions or antibodies or fusion proteins incorporating the modified constant is preferably not significantly different from the isotype matched controls or not worse than 2, 3, or 5 fold greater than the isotype matched control. Likewise, pharmacokinetic parameters such as Cmax, Cave rage, area under the curve and half-life are preferably not significantly different or at least not lower by a factor of no more than 2, 3 or 5 that isotype matched controls. Such parameters can be measured in a mouse such as described in the Examples, in other animal model or a human. Substantial retention of such PK parameters provides an indication that modified constant regions or antibodies or fusion proteins incorporating them have not undergone substantial conformational changes triggering enhanced removal mechanisms.

III. Antibodies and Fusion Proteins

The modified heavy chain constant regions described above can be incorporated into antibodies or other fusion proteins. For example, for expression of a monospecific antibody, a modified heavy chain constant region is expressed fused to a heavy chain variable region and together with a light chain including a light chain variable region and a light chain constant region. The heavy and light chain bind to one another via the CH1 region of the heavy chain and light chain constant region to a form a heterodimer. Two heterodimers then pair by association of hinge, CH2 and CH3 regions of the IgG heavy chain to form a tetramer unit, as is the case for a conventional antibody. For expression of a bispecific antibody, a modified heavy constant region is expressed fused to each of two heavy chain variable regions of different target specificities. The heavy chains can each assembly with a co-expressed light chain and the heavy chain-light chain complexes form heterodimers in which both heavy chains are present. The light chain variable regions can be the same (see e.g., US 20100331527A1) or different within a unit.

The modified constant regions can be used with any type of engineered antibody including chimeric, humanized, veneered or human antibodies. The antibody can be a monoclonal antibody or a genetically engineered polyclonal antibody preparation (see U.S. Pat. No. 6,986,986).

For fusion protein proteins, a modified constant region is expressed linked to a heterologous polypeptide. A heterologous polypeptide in a fusion protein is a polypeptide not naturally linked to an immunoglobulin constant region. Such a polypeptide can be a full-length protein or any fragment thereof of sufficient length to retain specific binding to the antigen bound by the full-length protein. For example, a heterologous polypeptide can be a receptor extracellular domain or ligand thereto. The heterologous polypeptide provides a binding region at the N-terminus of the constant region and is sometimes referred to simply as a binding region. The IgG CH1 region is not typically included in the constant region for fusion proteins. The upper hinge region is sometimes omitted or replaced by a synthetic linker peptide. Exemplary receptor proteins whose extracellular domains can be combined with modified heavy chain constant regions of the invention are known in the art (see e.g. Klinkert, et al. J Neuroimmunol. 72(2): 163-8 (1997); Milligan et al., Curr Pharm. Des. 10(17): 1989-2001 (2004); and Schwache & Muller-Newen, Eur. J Cell Biol. 91 (6-7):428-34 (2012), doi: 10.1016/j.ejcb.201 1.07.008. Epub 201 1 Sep. 29).

The binding region of a fusion protein can be any of the types of binding regions used in other fusion proteins produced to date (among others).

A multi-specific antibody or fusion protein can include binding specificities for an antigen on a target (e.g., a cancer cell or pathogen) and for an antigen on an effector cell (e.g., CD3 on a T-cell). Such a multi-specific complex forms a bridge between the target cell and effector cell and promotes cytotoxic or opsonization activity of the effector cell. A multi-specific antibody or fusion protein can additionally or alternatively include binding specificities for two different antigens on the same target (e.g., a cancer cell or pathogen). Such an antibody or fusion protein can have greater selective toxicity to the target cell than an antibody or fusion protein with specificity for a single antigen. Other multi-specific antibodies or fusion proteins include binding regions for both a receptor and its ligand or counter-receptor. Such antibodies or fusion proteins can exert greater inhibition than antibodies or fusion proteins binding receptor or ligand/counterreceptor alone. Any of these specificities and others can be combined in the same multi-specific complex.

Antibodies or fusion proteins can also be chemically modified by covalent conjugation to a polymer to, for instance, further increase their circulating half-life. Exemplary polymers, and methods to attach them to peptides, are illustrated in for instance U.S. Pat. NoS. 4,766,106, 4,179, 337, 4,495,285 and 4,609,546. Additional illustrative polymers include polyoxyethylated polyols and polyethylene glycol (PEG) (e.g., a PEG with a molecular weight of between about 1,000 and about 40,000, such as between about 2,000 and about 20,000, e.g., about 3,000-12,000 g/mol).

Antibodies or fusion proteins can be radiolabeled antibody for either diagnostic or therapeutic purposes. Examples of radioisotopes include $^3$H, $^{14}$C, $^{15}$N, $^{35}$S, $^{90}$Y, $^{99}$Tc, and $^{125}$I, $^{131}$I, $^{186}$Re, and $^{225}$Ac. Methods for preparing radiolabeled amino acids and antibodies or fusion proteins containing them are known (see for instance Junghans et al., in Cancer Chemotherapy and Biotherapy 655-686 (2nd edition, Chafner and Longo, eds., Lippincott Raven (1996)) and U.S. Pat. Nos. 4,681,581, 4,735,210, 5,101,827, 5,102,990 (U.S. Pat. No. RE35,500), U.S. Pat. Nos. 5,648,471 and 5,697, 902. For example, a radioisotope may be conjugated by a chloramine T method. Other detectable markers include an enzyme, a chromophore, or a fluorescent label.

Antibodies or fusion proteins can be conjugated to a toxic agent. Toxic agents can be cytotoxic or cytostatic. Some example of toxic agents include antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, camptothecins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

IV. Antibody Expression

Nucleic acids encoding antibody chains or fusion proteins can be made by solid state synthesis, PCR amplification of overlapping oligonucleotide fragments or site-directed mutagenesis of existing nucleic acids. Such nucleic acids are expressed in an expression vector. Vectors can be configured to encode a modified heavy chain constant region and/or human light chain constant region such that they can be expressed as fusions with inserted heavy chain and light chain variable regions or a heterologous polypeptide.

The origin of replication and expression control elements (promoter, enhancer, signal peptide and so forth) in a vector can be configured for use in different cell types, such as bacteria, yeast or other fungi, insect cells, and mammalian cells. Mammalian cells are a preferred host for expressing nucleotide segments encoding antibodies or fusion proteins of the invention (see Winnacker, From Genes to Clones, (VCH Publishers, NY, 1987)). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. Preferably, the cells are nonhuman. Preferably, an antibody or fusion protein of the invention is expressed from a monoclonal cell line.

Expression vectors for these cells can include expression control sequences, such as an origin of replication, a promoter, an enhancer (Queen et al., lmmunol. Rev. 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., J. Immunol. 148:1149 (1992).

Cells are transfected with one or more vectors encoding the antibody or fusion protein to be expressed. For a multi-chain antibody, the heavy and light chains can be expressed on the same or separate vectors. For expression of multi-specific complexes, the DNA encoding the components of the complexes (i.e., different antibodies or fusion proteins) can be on the same or different vectors.

Antibody or fusion protein chains are expressed, processed to remove signal peptides, assembled and secreted from host cells. Antibodies or fusion proteins can be purified from cell culture supernatants by conventional antibody purification methods. If the hybrid constant region includes an IgG portion, then the purification can include a chromatography step using protein A or protein G as the affinity reagent. Conventional antibody purification procedures, such as ion exchange, hydroxyapatite chromatograph or HPLC can also be used (see generally, Scopes, Protein Purification (Springer-Verlag, NY, 1982)).

V. Applications

Although antibodies and fusion proteins incorporating modified heavy chain constant regions of the invention can be generally used in methods of treatment or diagnosis, they are particularly useful in situations in which the mechanism of action of the antibody or fusion protein is entirely or at least predominantly independent of effector functions. Such is the case for example when the therapeutic objective is not to kill a target cell, but to inhibit or activate a cell surface molecule on its surface without triggering cytotoxicity. Another setting in which reduced binding to Fc receptors is desirable is when the antibody is bispecific, and its desired therapeutic properties arise from the different binding specificities. For example, a common usage of bispecific antibodies is to combine a tumor targeting specificity with a T cell activating specificity to trigger tumor-specific T cell killing. In this case, if the Fc portion binds to an Fc receptor, then potentially that could trigger undesirable killing of cells bearing Fc receptors by T cells, or killing of T cells by Fc receptor-bearing cells such as natural killer cells or macrophages. Another setting in which lack of effector functions can be advantageous is inhibiting aggregation of peptides that contribute to pathogenesis, such as in amyloidogenic disease. A further setting is in vivo diagnosis, in which an antibody or fusion protein is intended to bind to a target but not result in clearing the target or cells bearing the target.

VI. Targets

Antibodies or fusion proteins incorporating a modified heavy chain constant region may be directed to any number of cellular target proteins. The antibodies or fusion proteins are particularly useful for surface-bound target proteins. The desired response can be, for example, clearing of a target or cell or virus bearing the same, signal transduction through a receptor, e.g., inducing apoptosis, inhibiting a receptor binding to a ligand or counterreceptor, or internalization of an antibody or fusion protein conjugated to a toxic agent. Antibodies or fusion proteins can be made to the same targets as existing commercial antibodies or fusion proteins or can be derivatized versions of commercial antibodies or fusion proteins in which the existing constant region has been replaced by a modified constant region of the present invention.

Targets of interest include growth factor receptors (e.g., FGFR, HGFR, PDGFR, EFGR, NGFR, and VEGFR) and their ligands. Other targets are G-protein receptors and include substance K receptor, the angiotensin receptor, $\alpha$ and $\beta$ adrenergic receptors, the serotonin receptors, and PAF receptor. See, e.g., Gilman, Ann. Rev. Biochem. 56:625 649 (1987). Other targets are CD (cluster of differentiation markers). Other targets include ion channels (e.g., calcium, sodium, and potassium channels), muscarinic receptors, acetylcholine receptors, GABA receptors, glutamate receptors, and dopamine receptors (see Harpold, U.S. Pat. Nos. 5,401,629 and 5,436,128). Other targets are adhesion proteins such as integrins, selectins, and immunoglobulin superfamily members (see Springer, Nature 346:425 433 (1990). Osborn, Cell 62:3 (1990); Hynes, Cell 69:11 (1992)). Other targets are cytokines, such as interleukins IL-1 through about IL-37 to-date, tumor necrosis factors, interferon, and, tumor growth factor beta, colony stimulating factor (CSF) and granulocyte monocyte colony stimulating factor (GM-CSF). See Human Cytokines: Handbook for Basic & Clinical Research (Aggrawal et al. eds., Blackwell Scientific, Boston, Mass. 1991). Other targets are amyloidogenic peptides, such as Abeta, alpha-synuclein or prion peptide. Other targets are hormones, enzymes, and intracellular and intercellular messengers, such as, adenyl cyclase, guanyl cyclase, and phospholipase C. Target molecules can be human, mammalian or bacterial. Other targets are antigens, such as proteins, glycoproteins and carbohydrates from microbial pathogens, both viral and bacterial, and tumors.

Some examples of commercial antibodies and their targets include alemtuzumab (CD52); rituximab (CD20); trastuzumab (Her/neu); nimotuzumab, cetuximab (EGFR); bevacizumab (VEGF); palivizumab (RSV); abciximab (GpIIb/IIIa); infliximab, adalimumab, certolizumab, golimumab (TNF-alpha); baciliximab, daclizumab (IL-2); omalizumab (IgE); gemtuzumab (CD33); natalizumab (VLA-4); vedolizumab (alpha4beta7); belimumab (BAFF); otelixizumab, teplizumab (CD3); ofatumumab, ocrelizumab (CD20); epratuzumab (CD22); alemtuzumumab (CD52); eculizumab (C5); canakimumab (IL-1beta); mepolizumab (IL-5); reslizumab, tocilizumab (IL-6R); ustekinumab, briakinumab (IL-12, 23). Examples of commercial fusion proteins include etanercept which binds TNF-alpha, alefacept (LFA3-Fc fusion which binds CD2), TACI-Fc fusion which binds BAFF and APRIL, abatacept (CTLA-4-Fc which binds CD80 and CD86), and romiplostim (a peptide analog of thrombopoietin fused to Fc). Any of the commercial antibodies or fusion protein can be modified to replace the existing heavy chain constant region with a modified heavy chain constant region of the invention. Alternatively, a modified heavy chain constant region can be linked to other antibodies with the same target specificity (e.g., as determined by a competition assay) as any of the above commercial antibodies or fusion proteins.

VII. Methods of Treatment and Pharmaceutical Compositions

The antibodies and fusion proteins of the invention can also be used for suppressing various undesirable immune responses including those for the same therapies in which the commercial antibodies mentioned above have been used.

One category of immune disorders treatable by antibodies or fusion proteins of the invention is transplant rejection. When allogeneic cells or organs (e.g., skin, kidney, liver, heart, lung, pancreas and bone marrow) are transplanted into a host (i.e., the donor and donee are different individual from the same species), the host immune system is likely to mount an immune response to foreign antigens in the transplant (host-versus-graft disease) leading to destruction of the transplanted tissue. The antibodies or fusion proteins are useful, inter alia, to block alloantigen-induced immune responses in the donee.

A related use for antibodies or fusion proteins of the present invention is in modulating the immune response involved in "graft versus host" disease (GVHD). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants.

A further situation in which immune suppression is desirable is in treatment of autoimmune diseases such as type 1 diabetes, Crohn's disease, ulcerative colitis, multiple sclerosis, stiff man syndrome, rheumatoid arthritis, myasthenia gravis and lupus erythematosus. In these diseases, the body develops a cellular and/or humoral immune response against one of its own antigens leading to destruction of that antigen, and potentially crippling and/or fatal consequences. Autoimmune diseases are treated by administering one of the antibodies or fusion proteins of the invention. Other immune disorders treatable by antibodies or fusion proteins including modified constant regions of the invention include asthma, allergies, celiac disease, psoriasis, and uveitis. Celiac disease, psoriasis and uveitis are autoimmune diseases.

The antibodies or fusion proteins of the invention can be used for treating cancers in which a target antigen to which the antibody or fusion protein is expressed. The methods can be used to treat solid tumors, and particularly hematological malignancies, such as leukemia (e.g., T cell large granular lymphocyte leukemia), lymphoma (Hodgkin's or Non-Hodgkin's), or multiple myeloma. Solid tumors include skin (e.g., melanoma), ovarian, endometrial, bladder, breast, rectum, colon, gastric, pancreatic, lung, thymus, kidney and brain. Killing of cancer cells can result from mechanism independent of FcγR bindings, such as by induction of apoptosis, inhibition of a receptor-ligand interaction or by action of a conjugated cytotoxic moiety.

The antibodies or fusion protein can also be used for treatment of pathogenic infections, such as viral, bacterial, protozoan or fungal infection. Likewise killing can occur by mechanism independent of FcγR binding such as by inhibiting an interaction between a pathogen and a cell giving other elements of the immune system an opportunity to kill the pathogen or by action of a linked radionucleotide or toxin.

Antibodies or fusion proteins are administered in an effective regime meaning a dosage, route of administration and frequency of administration that delays the onset, reduces the severity, inhibits further deterioration, and/or ameliorates at least one sign or symptom of a disorder. If a subject is already suffering from a disorder, the regime can be referred to as a therapeutically effective regime. If the subject is at elevated risk of the disorder relative to the general population but is not yet experiencing symptoms, the regime can be referred to as a prophylactically effective regime. In some instances, therapeutic or prophylactic efficacy can be observed in an individual subject relative to historical controls or past experience in the same subject. In other instances, therapeutic or prophylactic efficacy can be demonstrated in a preclinical or clinical trial in a population of treated subjects relative to a control population of untreated subjects.

Exemplary dosages for an antibody or fusion protein are 0.01-20, or 0.5-5, or 0.01-1, or 0.01-0.5 or 0.05-0.5 mg/kg body weight (e.g., 0.1, 0.5, 1, 2, 3, 4 or 5 mg/kg) or 10-1500 mg as a fixed dosage. The dosage depends on the condition of the subject and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration into the systemic circulation by intravenous or subcutaneous administration is preferred. Intravenous administration can be, for example, by infusion over a period such as 30-90 min.

The frequency of administration depends on the half-life of the antibody or fusion protein in the circulation, the condition of the subject and the route of administration among other factors. The frequency can be daily, weekly, monthly, quarterly, or at irregular intervals in response to changes in the subject's condition or progression of the disorder being treated. An exemplary frequency for intravenous administration is between weekly and quarterly over a continuous cause of treatment, although more or less frequent dosing is also possible. For subcutaneous administration, an exemplary dosing frequency is daily to monthly, although more or less frequent dosing is also possible.

The number of dosages administered depends on whether the disorder is acute or chronic and the response of the disorder to the treatment. For acute disorders or acute exacerbations of chronic disorders between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the subject.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen. For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use.

Treatment with antibodies of the invention can be combined with other treatments effective against the disorder being treated. For treatment of immune disorders, conventional treatments include mast cell degranulation inhibitors, corticosteroids, nonsteroidal anti-inflammatory drugs, and stronger anti-inflammatory drugs such as azathioprine, cyclophosphamide, leukeran, FK506 and cyclosporine. Biologic anti-inflammatory agents, such as Tysabri® (natalizumab) or Humira® (adalimumab), can also be used. When used in treating cancer, the antibodies of the invention can be combined with chemotherapy, radiation, stem cell treatment, surgery or treatment with other biologics such as Herceptin® (trastuzumab) against the HER2 antigen, Avastin® (bevacizumab) against VEGF, or antibodies to the EGF receptor, such as (Erbitux®, cetuximab), and Vectibix® (panitumumab). Chemotherapy agents include chlorambucil, cyclophosphamide or melphalan, carboplatinum, daunorubicin, doxorubicin, idarubicin, and mitoxantrone, methotrexate, fludarabine, and cytarabine, etoposide or topotecan, vincristine and vinblastine. For infections, treatment can be in combination with antibiotics, anti-virals, anti-fungal or anti-protozoan agents or the like.

VIII. Other Applications

The antibodies or fusion proteins can be used for detecting their target molecule in the context of clinical diagnosis or treatment or in research. For example, the antibodies can be used to detect a cancer-related antigen as an indication a subject is suffering from an immune mediated disorder amenable to treatment. The antibodies can also be sold as research reagents for laboratory research in detecting targets and their response to various stimuli. In such uses, antibodies or fusion proteins can be labeled with fluorescent molecules, spin-labeled molecules, enzymes or radioisotypes, and can be provided in the form of kit with all the necessary reagents to perform the assay. The antibodies or fusion protein can also be used to purify their target antigens e.g., by affinity chromatography.

Presence of labeled antibodies or fusion may be detected in vivo for diagnosis purposes. In one embodiment, diagnosis comprises: a) administering to a subject an effective amount of a labeled antibody or fusion protein; b) waiting for a time interval following administration for permitting labeled antibody or fusion protein to concentrate at sites where antigen may be detected and to allow for unbound labeled antibody to be cleared to background level; c) determining a background level; and d) detecting the labeled antibody or fusion protein in the subject, such that detection of labeled antibody above the background level is indicative that the subject has the disease or disorder, or is indicative of the severity of the disease or disorder. In accordance with such embodiment, the antibody or fusion protein is labeled with an imaging moiety suitable for detection using a particular imaging system known to those skilled in the art. Background levels may be determined by various methods known in the art, including comparing the amount of labeled antibody detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MRI), and sonography.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1

Expression of Hinge-Modified Antibodies

Several of the antibodies described in the following examples are bispecific antibodies in which one arm is that of an anti-hCD3 antibody and the other arm is from an anti-hCD20 antibody as described by WO2014047231.

Antibody 1, 9F7_VH_IgG4_GGG-(233-236), was made by site-directed mutagenesis using QuikChange Lightning Site-Directed Mutagenesis Kit (Agilent Technologies, Inc.; Catalog#210518) following the manufacturer's protocol, and starting with a chimeric IgG4 CH region (which contained the modifications S228P and ELLG233-236PVA; see WO2014047231). After sequence confirmation, the coding region was moved to a parent vector using Xho1-Not1 restriction sites to avoid any mutations in the non-coding region, and subsequently generating a vector construct with the hinge-modified IgG4 CH, having the hinge modifications of SEQ ID NO:1. The anti-CD3(9F7 VH; see "L2K" based on WO2004/106380) variable region nucleic acid sequence was amplified and introduced into the same plasmid as the hinge-modified IgG4 S228P, GGG-(233-236) and the sequence was confirmed using PCR. The final plasmid was used to produce Antibody 1 using standard cell culture methodologies for isolating antibodies.

Antibody 2, 9F7_VH_IgG4_GG-(233-236), was made analogously to Antibody 1 by using site directed mutagenesis to generate a vector construct with the hinge modified IgG4 CH with GG--(233-236) (SEQ ID NO:2). The anti-CD3(9F7 VH; see WO2004/106380) variable region nucleic acid sequence was amplified and introduced into the same plasmid using standard molecular biology methods. Ab 2 was isolated using standard methodologies.

Antibody 3, 9F7_VH_IgG4_G-(233-236), was made analogously to Antibody 1 by using site directed mutagenesis to generate a vector construct with the hinge modified IgG4 CH with G---(233-236) (SEQ ID NO:3). The anti-CD3 (9F7 VH; see WO2004/106380) variable region nucleic acid sequence was amplified and introduced into the same plasmid using standard molecular biology methods. Ab 3 was isolated using standard methodologies.

Antibody 4, 9F7_VH_IgG4_No_G(233-236), was made analogously to Antibody 1 by using site directed mutagenesis to generate a vector construct with the hinge modified IgG4 CH with No_G(233-236) (SEQ ID NO:4). The anti-CD3(9F7 VH; see WO2004/106380) variable region nucleic acid sequence was amplified and introduced into the same plasmid. Ab 4 was isolated using standard methodologies.

Antibody 5, 3B9_VH_IgG4_GGG-(233-236), was made by site-directed mutagenesis using QuikChange Lightning Site-Directed Mutagenesis Kit (Agilent Technologies, Inc.; Catalog#210518) following the manufacturer's protocol, and starting with a chimeric IgG4 CH region (which contained the modifications S228P and ELLG233-236PVA; see WO2014047231). Antibody 5 is a monospecific, bivalent anti-CD20 antibody, and the anti-CD20 variable region nucleic acid sequence (3B9 VH) was isolated using standard methodologies as described in WO2014047231.

Antibody 6, 3B9_VH_IgG4_GG--(233-236), was made analogously to Antibody 5 by using site directed mutagenesis to generate a vector construct with the hinge modified IgG4 CH with GG--(233-236) (SEQ ID NO:2). The anti-CD20 (3B9 VH; see WO2014047231) variable region nucleic acid sequence was isolated using standard methodologies.

Antibody 7, 3B9_VH_IgG4_G---(233-236), was made analogously to Antibody 5 by using site directed mutagenesis to generate a vector construct with the hinge modified IgG4 CH with G---(233-236) (SEQ ID NO:3). The anti-CD20 (3B9 VH; see WO2014047231) variable region nucleic acid sequence was isolated using standard methodologies.

Antibody 8, 3B9_VH_IgG4_No_G(233-236), was made analogously to Antibody 5 by using site directed mutagenesis to generate a vector construct with the hinge modified IgG4 CH with No_G(233-236) (SEQ ID NO:4). The anti-CD20 (3B9 VH; see WO2014047231) variable region nucleic acid sequence was isolated using standard methodologies.

Antibody 9, anti-transmembrane (TM) protein variable domains (B6H12.2, obtained from BioXCell, Cat. No. BE0019-1) were cloned in to a plasmid containing the hinge-modified IgG4 S228P, GGG-(233-236) nucleic acid, by methods similarly described for Antibody 1.

Antibody 10, B6H12.2_VH_IgG4_PVA was made according to protocols described herein, having a chimeric IgG4(S228P and ELLG233-236PVA) Fc domain.

Antibody 11, anti-FELD1_VH_IgG4_PVA antibody, is isotype matched to Antibody 10, having a chimeric IgG4 (S228P and ELLG233-236PVA) Fc domain.

Control Antibody A (Lot-L2), 9F7_VH_IgG4, is an antiCD3 (9F7 VH; see WO2004/106380) human IgG4 isotype antibody (except having a CH3* mutation 435R and 436F, designated the star mutation—see US20100331527A1).

Control Antibody B (Lot-L2), 9F7_VH_IgG1, is an antiCD3 (9F7 VH; see WO2004/106380) human IgG1 isotype antibody.

Control Antibody C: 9F7_VLx3B9_VH_IgG4, was made according to the protocols described in WO2014047231. Control Ab C is a bispecific antiCD3xanti-CD20 monoclonal antibody having a wild-type IgG4 heavy chain (except one arm has the star mutation in the CH3 region for ease of bispecific antibody isolation).

Control Antibody D (Lot-L5): 9F7_VLx3B9_VH_IgG4_PVA, was made according to the protocols described in WO2014047231. Control Ab D is a bispecific anti-CD3xanti-CD20 monoclonal antibody having a modified IgG4 heavy chain [chimeric IgG4(S228P and ELLG233-236PVA), except one heavy chain has the star mutation in the CH3 region for ease of bispecific antibody isolation].

Control Antibody E: Anti-FeID1 monoclonal antibody binds a feline antigen with no cross-reactivity to human CD20 or CD3. This IgG1 non-specific antibody control was obtained by methods described in PCT Publication No. WO2013/166236, published on Nov. 7, 2013.

Control Antibody F: is small batch (supernatant) preparation of 9F7 (anti-CD3) with the chimeric IgG4 Fc (S228P and ELLG233-236PVA) (See also WO2014047231).

Control Ab G: 9F7_VH_IgG4_PVA was made according to the protocols described in WO2014047231 (Lot#2, purified). Control Ab G is a monospecific anti-CD3 monoclonal antibody having a modified IgG4 heavy chain [chimeric IgG4(S228P and ELLG233-236PVA), except one heavy chain has the star mutation in the CH3 region for ease of bispecific antibody isolation].

Control Ab H (Lot #02-091210): 3139_VH_IgG1 is an anti-CD20 (3B9 VH; see WO2004/106380) human IgG1 isotype antibody.

Control Ab I (Lot #01-110607): 3139_VH_IgG4 is an anti-CD20 (3B9 VH; see WO2004/106380) human IgG4 isotype antibody.

Control Ab J (Lot #L1): 9F7_VK x3B9_VH_IgG4_PVA was made according to the protocols described in WO2014047231. Control Ab J is a bispecific anti-CD3xanti-CD20 monoclonal antibody having a modified IgG4 heavy chain [chimeric IgG4 (S228P and ELLG233-236PVA), except one heavy chain has the star mutation in the CH3 region for ease of bispecific antibody isolation].

Example 2

Loss of Affinity to Fcγ Receptors

The hinge-modified antibodies (i.e. GGG-, GG--, G--- or no-G hinge replacement; Antibodies 1-4) and various control antibodies were tested for binding affinity to Fcγ receptors by surface plasmon resonance (SPR). The controls included Control Ab D (antiCD3xantiCD20-sIgG4 (S228P and ELFG233-236PVA), Control Ab B (antiCD3, human IgG1 isotype), and Control Ab A (antiCD3, human IgG4 isotype).

Briefly SPR experiments were performed at 25° C. on a Biacore T200 instrument employing a carboxymethyl dextran-coated (CM-5) chip. A mouse monoclonal anti-pentahistidine antibody (GE Healthcare) was immobilized on the surface of the CM-5 sensor chip using standard amine-coupling chemistry. 140RU-376RU of His-tagged human or monkey FcγR proteins were captured on the anti-pentahistidine amine-coupled CM-5 chip (or in the case of FcRn, about 155-299 RU of FcRn mutant contructs were immobilized on a high density anti-myc coated Biacore chip) and stock solutions of antibodies were injected at 20 µl/min for 2.5 min over the captured proteins and serially diluted. mAb binding response was monitored and, for low affinity receptors, steady-state binding equilibrium was calculated. Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives ($t_{1/2}$) were calculated from the kinetic rate constants as: $K_D$ (M)=$k_d/k_a$; and $t_{1/2}$ (min)=(In2/(60*$k_d$). Some KDs were derived using the steady state equilibrium dissociation constant; NB =no binding observed.

An anti-CD3 antibody designated 9F7 having a heavy chain constant region including hinge segments designated SEQ ID NO:1, SEQ ID NO:2, SEQ ID:3 or SEQ ID NO:4 at residues 226-236, and of human IgG4 isotype, was tested for binding affinity to human FcγRI, RIIA, RIIB and RIII. Controls included the same antibody with wildtype IgG1 or IgG4 isotypes, and the same antibody with IgG4 isotype with a different modification of the hinge region (i.e. the hinge modification has positions 226-236 occupied by CPPCPAPPVA-, the same sequences as in human IgG2, therefore referred to as chimericFc). In the IgG4 chimeric Fc format, the remaining segments of the constant region are human IgG4. In the IgG1 chimeric Fc format, the CH1 and CH3 segments are human IgG1 and CH2 is human IgG4.

The data show binding is reduced to background levels in all of the hinge-modified Antibodies 1-4 to each of human FcγRI, IIA, IIB and III. By contrast, binding of the IgG1 and IgG4 chimericFc antibodies is reduced to background levels for FcγRI and FcγIII, but is still significant to FcγRIIA and RIIB. All of the hinge-modified Antibodies 1-4 maintain binding to FcRn, comparable to IgG4 and chimeric hinge IgG4 formats. See FIGS. 6-10.

Example 3

Cytotoxicity Analysis

U937 cells are a monocyte cell line expressing FcγI and FcγRIIA. U937 cells were used as a positive killer effector control in the following cytotoxicity assay. As such, the ability of antibodies with chimeric CH regions to kill U937 cells via Fc/FcγR interactions was tested. Calcein killing assays were carried out using the following protocol: Human and cynomolgus Peripheral Blood Mononuclear Cells (PBMCs) were isolated over Ficoll-Paque (GE Healthcare Life Sciences) or via Lymphocyte-Mammal density cell separation media (Cedarlane Laboratories), respectively. The isolated PBMCs were activated over a course of several days with media containing recombinant human IL-2 (30 U/ml) and T-cell activation beads (anti-CD3/CD28 for human PBMC, anti-CD2/CD3/CD28 for cynomolgus PBMC). Activated T-cells were isolated from the PBMCs by centrifugation, then resuspended in 1 ml media. The magnetized beads were removed from the T-cells. Target cells (U937) were labeled with calcein, then washed and followed by incubation (10,000 cells per well) with 15-fold serial dilutions of purified Ab/sup and immortal CD8+ human T-cells (100,000 cells/well) for 3 hr at 37 C (effector:target ratio—10:1) Following incubation plates were centrifuged and the supernatant transferred to black clear bottom plates for fluorescence analysis. Each EC50, defined as the molar concentration of antibody that induces 50% cytotoxicity, was determined using Prism (GraphPad Software, San Diego, Calif.). Values were calculated using a 4-parameter non-linear regression analysis (FIG. 11A).

Figure 11B:
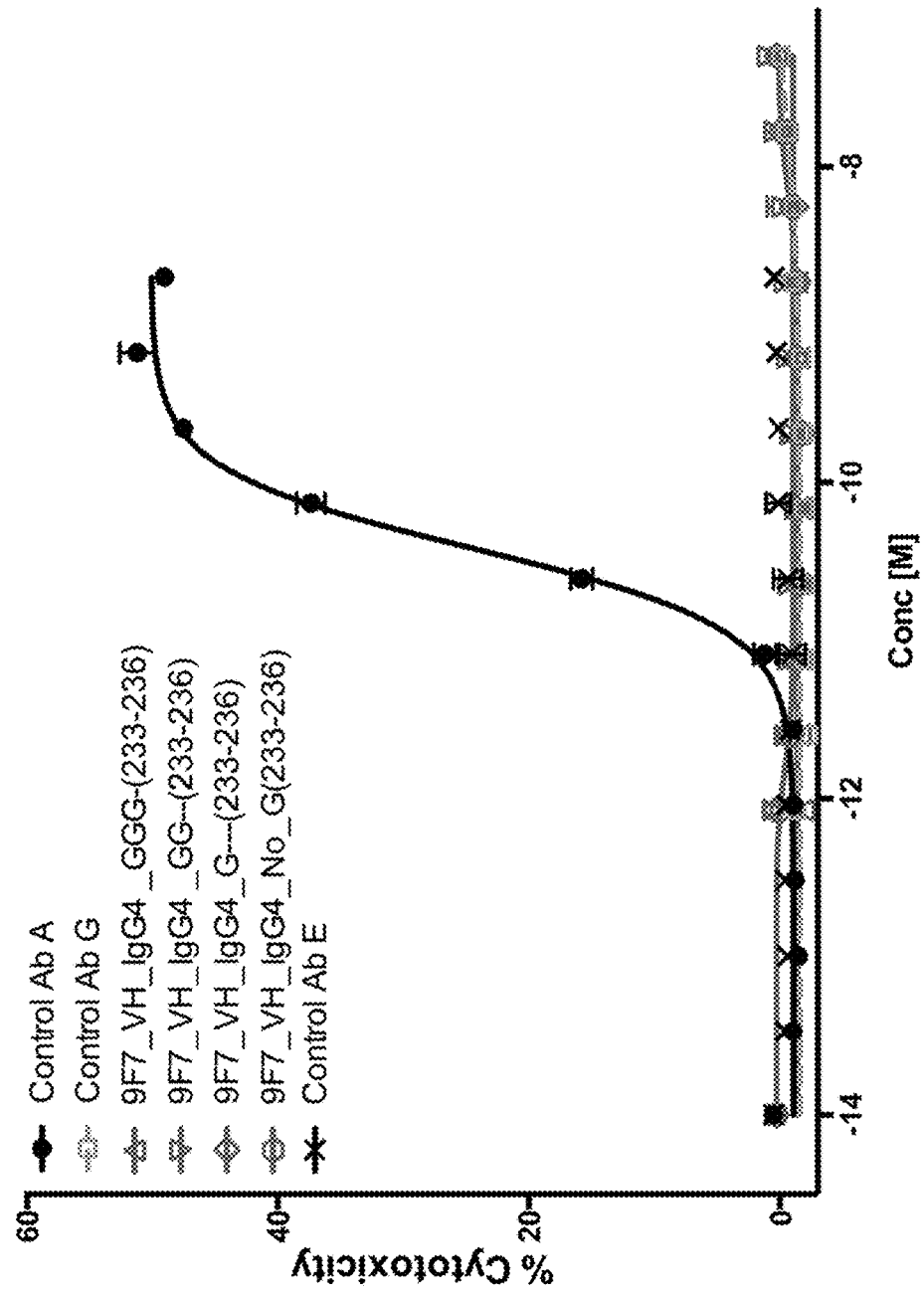
FIG. 11B also shows hinge-modified antibodies, that have been fully purified, and that are unable to recruit human T-cells to lyse U937 cells bearing FcγRI and FcγRIIA.

The above experiments were performed with crude extracts of the antibodies in cell culture supernatants (FIG. 11A). Analogous experiments were done with the same antibodies purified over standard affinity columns or using the method described in Davis et al. (see US2010/0331527) for bispecific antibodies (FIG. 11B).

The data show that all of the hinge-modified antibodies 1-4 had only background levels of cytotoxicity as was also the case for the IgG4 chimericFc antibody. IgG1 and IgG4 wildtype antibodies showed strong cytotoxicity due to their ability to interact with FcγRI and FcγRIIA. See FIG. 11A and FIG. 11B.

Example 4

Activation of Jurkat Cells

This example tests whether an antibody can activate Jurkat cells (T cell leukemia cell line) transformed with an NFAT-luciferase construct that acts as marker of activation. Activation requires an antibody to anchor on a HEK293 cells expressing FcγRIIA or FcγRIIB.

Figure 12A:
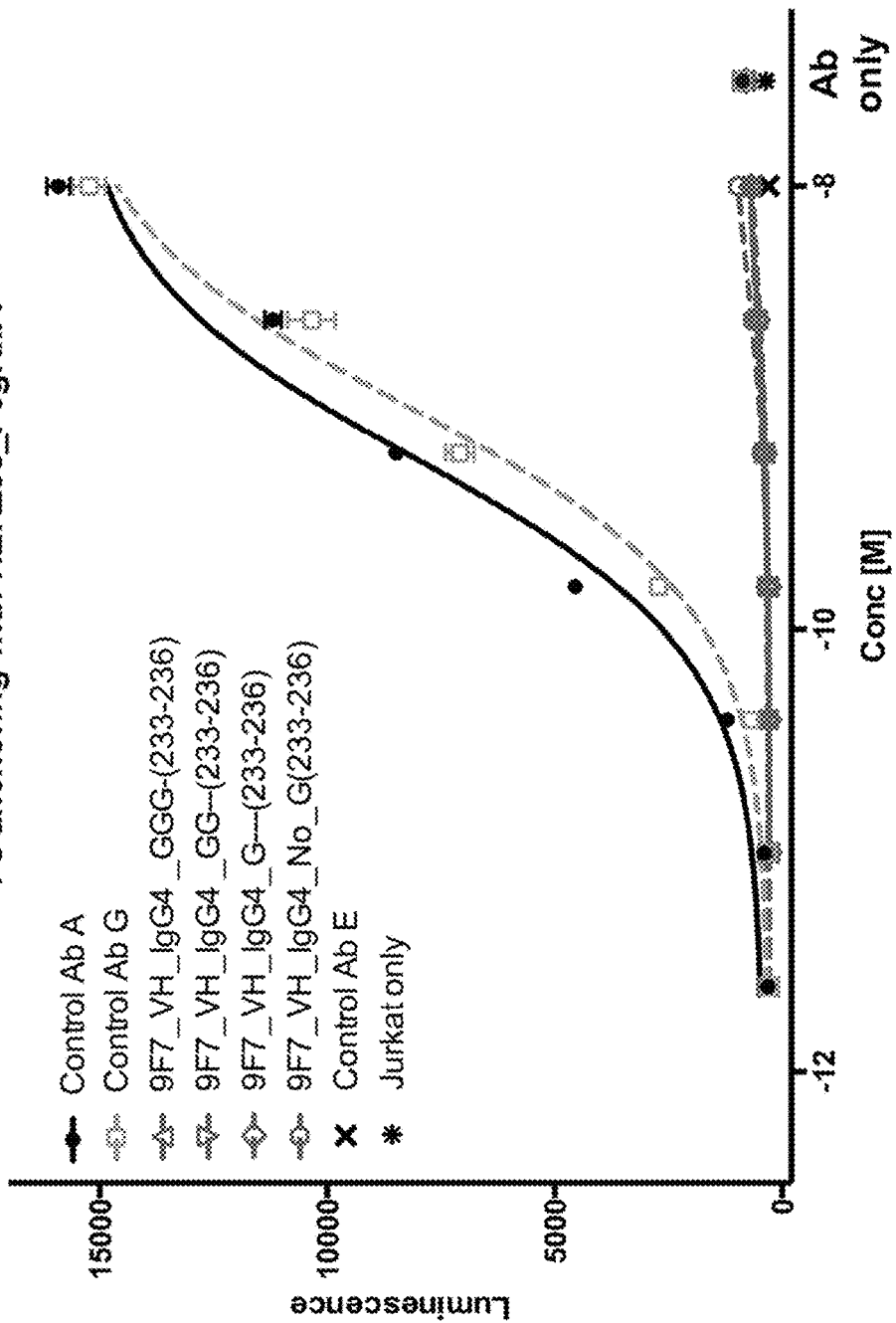
Figure 12B:
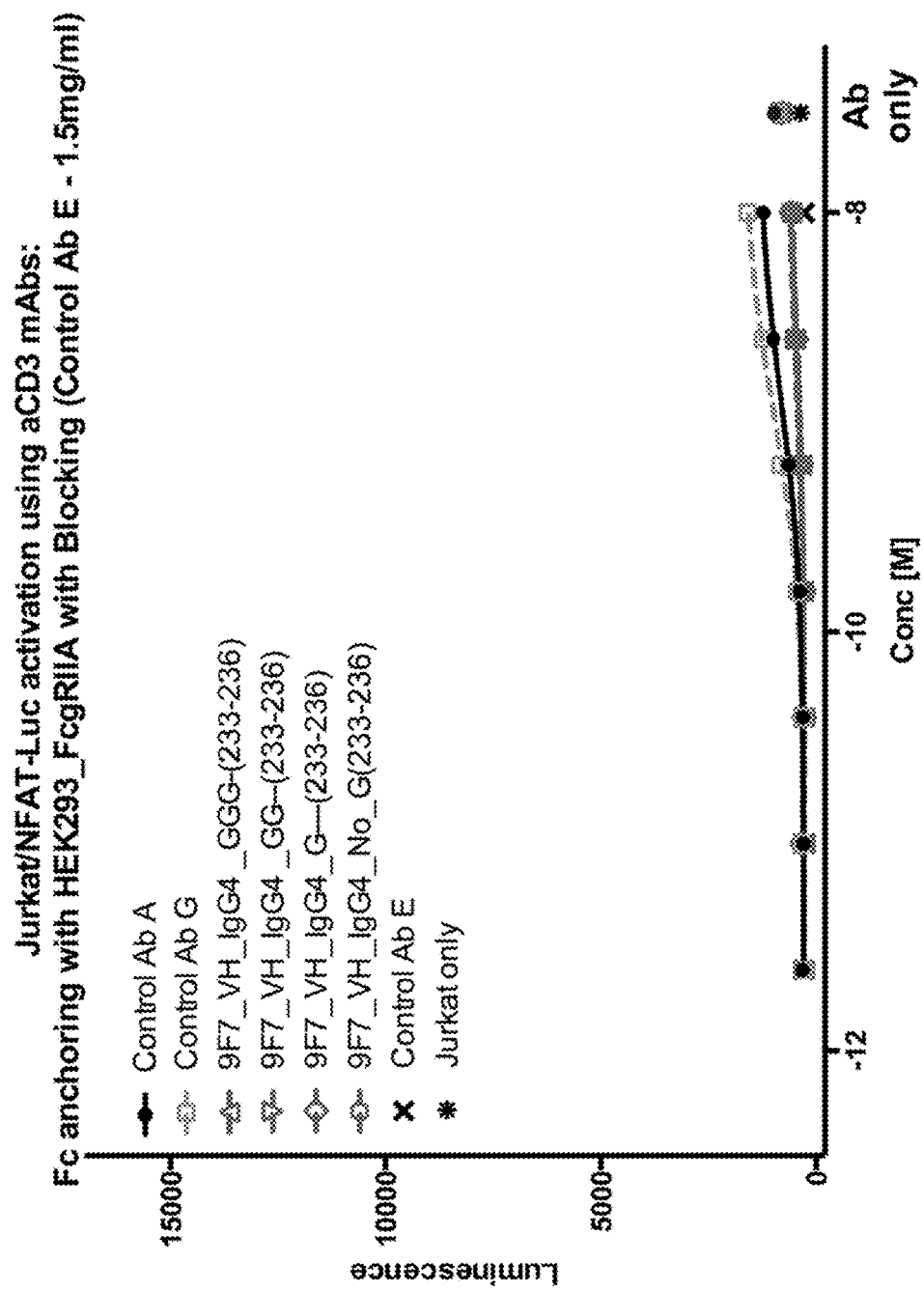

Jurkat/NFAT-Luc cells (50,000/well) were incubated with target cells (50,000/well) in the presence of serial dilutions of different antibodies with (FIG. 12B, 12D) or without (FIG. 12A, 12C) antibody to an irrelevant antigen (FeID1) (1.5 mg/ml) for 4 h at 37 C. One-Glo (Promega) was added to measure luciferase activity.

The data show that all of the hinge-modified Antibodies 1-4 had only background levels of activation. See. FIGS. 12A-12D. Accordingly, all hinge-modified Antibodies 1-4 lack ability to bind to FcγRIIA or IIB on HEC cells.

A positive control antibody of wildtype human IgG4 antibody showed strong activation that was reduced to near background levels by the anti-FeID1 antibody, which competes for an anchoring site on HEK293.

To show that the lack of activation of Jurkat cells resulted from dampening the FcγR binding ability of hinge-modified antibodies rather than an impaired ability of the antibodies to bind their CD3 target, an assay was performed with the antibodies cross-linked to a plate surface. Maxisorp plates were coated with a 2-fold serial dilution of different Abs starting at 10 nM overnight at 4° C. Next day 50,000 Jurkat NFAT Luc cells were added per well and media to make up the total volume to 100 ul/well and incubate at 37° C. for 5 hours. 100 ul One-Glo (Promega) was added to measure luciferase activity. Transfer to opaque white nunc plates before reading luciferase activity. In this experiment all of the hinge-modified antibodies 1-4 showed similar activation to IgG4 isotype matched controls. See FIG. 13.

Example 5

ADCC Assay

In this assay, the hinge-modified antibodies have variable regions (3B9_VH) that bind the cell surface target antigen CD20 (Antibodies 5 through 8, described above). CD20 positive target cells (Daudi) were labeled with calcein, then washed and followed by incubation (10,000 cells per well) with 6-fold serial dilutions of purified antibody and NK92_CD16V cells (NK92 cells engineered to express the higher affinity V allele of FcγRIIIa at 50,000 cells/well) for 4 hr at 37 C (effector:target ratio—5:1). Target cell lysis was determined by measuring the calcein fluorescence in the supernatant. Percent cytotoxicity and EC50 were calculated analogously to that described in Example 3. FIG. 14 shows the hinge-modified antibodies do not mediate ADCC activity (FIG. 14) against Daudi cells.

Example 6

PK Assessment of Anti-TM Monoclonal Antibody with Modified Hinge

Antibodies having variable domains that bind to a multipass transmembrane (TM) protein widely expressed in normal tissues and upregulated in various cancers were produced using well known techniques (see U.S. Pat. No. 5,057,604; WO 2011/143624; and WO 97/27873).

Assessment of the pharmacokinetic (PK) clearance rate: anti-TM antibody having a modified hinge (Antibody 9) and a chimeric IgG4 Fc (Antibody 10), as well as an isotype control with chimeric IgG4 Fc (Antibody 11) were assessed in C57BL/6 Wild-Type (WT) mice. For each anti-TM mAb or isotype control, cohorts of three mice were given a subcutaneous (s.c.) dose at 1 mg/kg. Mice were bled prior to the dosing and the serum samples were designated as a pre-bleed or zero time point. All mice were bled at 6 hours, 1, 3, 7, 10 and 14 days post injection for PK analysis. Serum fractions from the bleeds were separated and frozen at −80° C. until analysis was conducted.

Determination of Total Drug Level in Sera by ELISA: Circulating anti-TM antibody levels were determined by total human antibody analysis using an ELISA immunoassay. Briefly, a goat anti-human IgG polyclonal antibody (Jackson ImmunoResearch, #109-005-098) at 1 μg/ml in PBS was immobilized on 96-well plates overnight and the plates were blocked with 5% BSA. The drug containing serum samples in six-dose serial dilutions and the reference standards of the respective antibodies in 12-dose serial dilutions were transferred to the prepared plates and incubated for one hour. The plate-bound anti-TM antibodies were then detected using a goat anti-human IgG polyclonal antibody conjugated with horseradish peroxidase (Jackson ImmunoResearch, #109-035-098). The plates were developed with TMB substrate (BD Pharmingen, #51-2606KC, #15-2607KC) according to manufacturer's recommend protocol and signals of optical density (OD) at 450 nm were recorded using a Perkin Elmer Victor X4 Multimode Plate Reader. The anti-TM antibody concentrations in the sera were calculated based on the reference standard calibration curve generated using GraphPad Prism software.

C57BL/6 WT mice were given a single s.c. dose of 1 mg/kg of Antibody 9, Antibody 10 or Isotype control (Ab 11). Concentrations of total antibody were determined at 6 time points over a 14-day time period. The total anti-TM antibody concentrations for each antibody are summarized in Table 1.

TABLE 1

Serum Antibody Concentrations (Days 0, 0.25, 1, 3, 7, and 14)

| Antibody | Time (d) | Total mAb concentration in mouse serum | |
|---|---|---|---|
| | | Mean (μg/mL) | +/−SD |
| Antibody 9 | 0 | ND | ND |
| Antibody 9 | 0.25 | 10 | 0.8 |
| Antibody 9 | 1 | 13.3 | 0.8 |
| Antibody 9 | 3 | 10.6 | 0.7 |
| Antibody 9 | 7 | 8.6 | 1 |
| Antibody 9 | 14 | 5.3 | 0.4 |
| Antibody 9 | 0 | ND | ND |
| Antibody 10 | 0.25 | 11.2 | 1.5 |
| Antibody 10 | 1 | 14.4 | 0.9 |
| Antibody 10 | 3 | 11.0 | 1.6 |
| Antibody 10 | 7 | 9.8 | 0.9 |
| Antibody 10 | 14 | 6.4 | 0.5 |
| Antibody 11 | 0 | ND | ND |
| Antibody 11 | 0.25 | 10.1 | 0.9 |
| Antibody 11 | 1 | 12.0 | 0.4 |
| Antibody 11 | 3 | 10 | 0.6 |
| Antibody 11 | 7 | 9 | 0.8 |
| Antibody 11 | 14 | 5.1 | 0.2 |

Time = Time in days post single-dose injection;
Day = Day of study;
SD = Standard deviation;
ND = Not detected The mean concentration versus time profiles show that all three antibodies achieved a maximum serum concentration ($C_{max}$) on day 1. Antibody 9, Antibody 10 and Isotype control had comparable $C_{max}$ values of 13, 14 and 12 μg/mL, respectively. All three antibodies exhibited a linear elimination with overlapping PK profiles. These PK profiles are similar to those seen in previous studies for IgG1 and IgG4(S228P) isotype controls (data not shown). At day 14, Antibody 9 and isotype control has average drug levels around 5 μg/mL while Antibody 10 had average drug levels around 6 μg/mL.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

SEQUENCE LISTING

```
SEQ ID NO: 1 GGG-(233-236)
PPCPAPGGG-GPSVF

SEQ ID NO: 2 GG--(233-236)
CPPCPAPGG--GPSVF

SEQ ID NO: 3 G---(233-236)
CPPCPAPG---GPSVF

SEQ ID NO: 4 No_G-(233-236)
CPPCPAP----GPSVF

SEQ ID NO: 5 IgG4_GGG-(233-236)
ASTKGPSVFP LAPCSRSTSE STAALGCLVK DYFPEPVTVS WNSGALTSGV HTFPAVLQSS GLYSLSSVVT
VPSSSLGTKT YTCNVDHKPS NTKVDKRVES KYGPPCPPCP APGGGGPSVFLFPPKPKDT LMISRTPEVT
CVVVDVSQED PEVQFNWYVD GVEVHNAKTK PREEQFNSTYRVVSVLTVLH QDWLNGKEYK CKVSNKGLPS
SIEKTISKAK GQPREPQVYT LPPSQEEMTK NQVSLTCLVK GFYPSDIAVE WESNGQPENN YKTTPPVLDS
DGSFFLYSRL TVDKSRWQEGNVFSCSVMHE ALHNHYTQKS LSLSLGK

SEQ ID NO: 6 IgG4_GG--(233-236)
ASTKGPSVFP LAPCSRSTSE STAALGCLVK DYFPEPVTVS WNSGALTSGV HTFPAVLQSS GLYSLSSVVT
VPSSSLGTKT YTCNVDHKPS NTKVDKRVES KYGPPCPPCP APGGGPSVFLFPPKPKDT LMISRTPEVT
CVVVDVSQED PEVQFNWYVD GVEVHNAKTK PREEQFNSTYRVVSVLTVLH QDWLNGKEYK CKVSNKGLPS
SIEKTISKAK GQPREPQVYT LPPSQEEMTK NQVSLTCLVK GFYPSDIAVE WESNGQPENN YKTTPPVLDS
DGSFFLYSRL TVDKSRWQEGNVFSCSVMHE ALHNHYTQKS LSLSLGK
```

SEQUENCE LISTING

SEQ ID NO: 7 IgG4_G---(233-236)
ASTKGPSVFP LAPCSRSTSE STAALGCLVK DYFPEPVTVS WNSGALTSGV HTFPAVLQSS GLYSLSSVVT
VPSSSLGTKT YTCNVDHKPS NTKVDKRVES KYGPPCPPCP APGGPSVFLFPPKPKDT LMISRTPEVT CVVVDVSQED
PEVQFNWYVD GVEVHNAKTK PREEQFNSTYRVVSVLTVLH QDWLNGKEYK CKVSNKGLPS SIEKTISKAK
GQPREPQVYT LPPSQEEMTK NQVSLTCLVK GFYPSDIAVE WESNGQPENN YKTTPPVLDS DGSFFLYSRL
TVDKSRWQEGNVFSCSVMHE ALHNHYTQKS LSLSLGK

SEQ ID NO: 8 IgG4_No_G-(233-236)
ASTKGPSVFP LAPCSRSTSE STAALGCLVK DYFPEPVTVS WNSGALTSGV HTFPAVLQSS GLYSLSSVVT
VPSSSLGTKT YTCNVDHKPS NTKVDKRVES KYGPPCPPCP APGPSVFLFPPKPKDT LMISRTPEVT CVVVDVSQED
PEVQFNWYVD GVEVHNAKTK PREEQFNSTYRVVSVLTVLH QDWLNGKEYK CKVSNKGLPS SIEKTISKAK
GQPREPQVYT LPPSQEEMTK NQVSLTCLVK GFYPSDIAVE WESNGQPENN YKTTPPVLDS DGSFFLYSRL
TVDKSRWQEGNVFSCSVMHE ALHNHYTQKS LSLSLGK

SEQ ID NO: 9 IgG4*_GGG-(233-236)
ASTKGPSVFP LAPCSRSTSE STAALGCLVK DYFPEPVTVS WNSGALTSGV HTFPAVLQSS GLYSLSSVVT
VPSSSLGTKT YTCNVDHKPS NTKVDKRVES KYGPPCPPCP APGGGGPSVFLFPPKPKDT LMISRTPEVT
CVVVDVSQED PEVQFNWYVD GVEVHNAKTK PREEQFNSTYRVVSVLTVLH QDWLNGKEYK CKVSNKGLPS
SIEKTISKAK GQPREPQVYT LPPSQEEMTK NQVSLTCLVK GFYPSDIAVE WESNGQPENN YKTTPPVLDS
DGSFFLYSRL TVDKSRWQEGNVFSCSVMHE ALHNRFTQKS LSLSLGK

SEQ ID NO: 10 IgG4*_GG--(233-236)
ASTKGPSVFP LAPCSRSTSE STAALGCLVK DYFPEPVTVS WNSGALTSGV HTFPAVLQSS GLYSLSSVVT
VPSSSLGTKT YTCNVDHKPS NTKVDKRVES KYGPPCPPCP APGGGPSVFLFPPKPKDT LMISRTPEVT
CVVVDVSQED PEVQFNWYVD GVEVHNAKTK PREEQFNSTYRVVSVLTVLH QDWLNGKEYK CKVSNKGLPS
SIEKTISKAK GQPREPQVYT LPPSQEEMTK NQVSLTCLVK GFYPSDIAVE WESNGQPENN YKTTPPVLDS
DGSFFLYSRL TVDKSRWQEGNVFSCSVMHE ALHNRFTQKS LSLSLGK

SEQ ID NO: 11 IgG4*_G---(233-236)
ASTKGPSVFP LAPCSRSTSE STAALGCLVK DYFPEPVTVS WNSGALTSGV HTFPAVLQSS GLYSLSSVVT
VPSSSLGTKT YTCNVDHKPS NTKVDKRVES KYGPPCPPCP APGGPSVFLFPPKPKDT LMISRTPEVT CVVVDVSQED
PEVQFNWYVD GVEVHNAKTK PREEQFNSTYRVVSVLTVLH QDWLNGKEYK CKVSNKGLPS SIEKTISKAK
GQPREPQVYT LPPSQEEMTK NQVSLTCLVK GFYPSDIAVE WESNGQPENN YKTTPPVLDS DGSFFLYSRL
TVDKSRWQEGNVFSCSVMHE ALHNRFTQKS LSLSLGK

SEQ ID NO: 12 IgG4*_No_G-(233-236)
ASTKGPSVFP LAPCSRSTSE STAALGCLVK DYFPEPVTVS WNSGALTSGV HTFPAVLQSS GLYSLSSVVT
VPSSSLGTKT YTCNVDHKPS NTKVDKRVES KYGPPCPPCP APGPSVFLFPPKPKDT LMISRTPEVT
CVVVDVSQED PEVQFNWYVD GVEVHNAKTK PREEQFNSTYRVVSVLTVLH QDWLNGKEYK
CKVSNKGLPS SIEKTISKAK GQPREPQVYT LPPSQEEMTK NQVSLTCLVK GFYPSDIAVE WESNGQPENN
YKTTPPVLDS DGSFFLYSRL TVDKSRWQEGNVFSCSVMHE ALHNRFTQKS LSLSLGK

SEQ ID NOS. 13-15 are wildtype human IgG1, IgG2 and IgG4 as shown in FIGS. 2-4.

SEQ ID NO: 16 IgG1 GGG
ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP
KSCDKTHTCPPCP APGGGG PSVFLFPPKP KDTLMISRTP EVTCVVVDVS
HEDPEVKFNW YVDGVEVHNA KTKPREEQYN STYRVVSVLT VLHQDWLNGK
EYKCKVSNKA LPAPIEKTIS KAKGQPREPQ VYTLPPSRDE LTKNQVSLTC
LVKGFYPSDI AVEWESNGQP ENNYKTTPPV LDSDGSFFLY SKLTVDKSRW
QQGNVFSCSV MHEALHNHYT QKSLSLSPGK

SEQ ID NO: 17 IgG1 GG
ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP
KSCDKTHTCPPCP APGGG PSVFLFPPKP KDTLMISRTP EVTCVVVDVS
HEDPEVKFNW YVDGVEVHNA KTKPREEQYN STYRVVSVLT VLHQDWLNGK
EYKCKVSNKA LPAPIEKTIS KAKGQPREPQ VYTLPPSRDE LTKNQVSLTC
LVKGFYPSDI AVEWESNGQP ENNYKTTPPV LDSDGSFFLY SKLTVDKSRW
QQGNVFSCSV MHEALHNHYT QKSLSLSPGK

SEQ ID NO: 18 IgG1 G
ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP
KSCDKTHTCPPCP APGG PSVFLFPPKP KDTLMISRTP EVTCVVVDVS
HEDPEVKFNW YVDGVEVHNA KTKPREEQYN STYRVVSVLT VLHQDWLNGK
EYKCKVSNKA LPAPIEKTIS KAKGQPREPQ VYTLPPSRDE LTKNQVSLTC
LVKGFYPSDI AVEWESNGQP ENNYKTTPPV LDSDGSFFLY SKLTVDKSRW
QQGNVFSCSV MHEALHNHYT QKSLSLSPGK

SEQ ID NO: 19 IgG1 no G
ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP
KSCDKTHTCPPCP APG PSVFLFPPKP KDTLMISRTP EVTCVVVDVS
HEDPEVKFNW YVDGVEVHNA KTKPREEQYN STYRVVSVLT VLHQDWLNGK

```
EYKCKVSNKA LPAPIEKTIS KAKGQPREPQ VYTLPPSRDE LTKNQVSLTC
LVKGFYPSDI AVEWESNGQP ENNYKTTPPV LDSDGSFFLY SKLTVDKSRW
QQGNVFSCSV MHEALHNHYT QKSLSLSPGK

SEQ ID NO: 20 IgG1* GGG
ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP
KSCDKTHTCPPCP APGGGG PSVFLFPPKP KDTLMISRTP EVTCVVVDVS
HEDPEVKFNW YVDGVEVHNA KTKPREEQYN STYRVVSVLT VLHQDWLNGK
EYKCKVSNKA LPAPIEKTIS KAKGQPREPQ VYTLPPSRDE LTKNQVSLTC
LVKGFYPSDI AVEWESNGQP ENNYKTTPPV LDSDGSFFLY SKLTVDKSRW
QQGNVFSCSV MHEALHNRFT QKSLSLSPGK

SEQ ID NO: 21 IgG1* GG
ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP
KSCDKTHTCPPCP APGGG PSVFLFPPKP KDTLMISRTP EVTCVVVDVS
HEDPEVKFNW YVDGVEVHNA KTKPREEQYN STYRVVSVLT VLHQDWLNGK
EYKCKVSNKA LPAPIEKTIS KAKGQPREPQ VYTLPPSRDE LTKNQVSLTC
LVKGFYPSDI AVEWESNGQP ENNYKTTPPV LDSDGSFFLY SKLTVDKSRW
QQGNVFSCSV MHEALHNRFT QKSLSLSPGK

SEQ ID NO: 22 IgG1* G
ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP
KSCDKTHTCPPCP APGG PSVFLFPPKP KDTLMISRTP EVTCVVVDVS
HEDPEVKFNW YVDGVEVHNA KTKPREEQYN STYRVVSVLT VLHQDWLNGK
EYKCKVSNKA LPAPIEKTIS KAKGQPREPQ VYTLPPSRDE LTKNQVSLTC
LVKGFYPSDI AVEWESNGQP ENNYKTTPPV LDSDGSFFLY SKLTVDKSRW
QQGNVFSCSV MHEALHNRFT QKSLSLSPGK

SEQ ID NO: 23 IgG1* no G
ASTKGPSVFP LAPSSKSTSG GTAALGCLVK DYFPEPVTVS WNSGALTSGV
HTFPAVLQSS GLYSLSSVVT VPSSSLGTQT YICNVNHKPS NTKVDKKVEP
KSCDKTHTCPPCP APG PSVFLFPPKP KDTLMISRTP EVTCVVVDVS
HEDPEVKFNW YVDGVEVHNA KTKPREEQYN STYRVVSVLT VLHQDWLNGK
EYKCKVSNKA LPAPIEKTIS KAKGQPREPQ VYTLPPSRDE LTKNQVSLTC
LVKGFYPSDI AVEWESNGQP ENNYKTTPPV LDSDGSFFLY SKLTVDKSRW
QQGNVFSCSV MHEALHNRFT QKSLSLSPGK

SEQ ID NO: 24: IgG2 GGG
ASTKGPSVFP LAPCSRSTSE STAALGCLVK DYFPEPVTVS WNSGALTSGV
HTFPAVLQSS GLYSLSSVVT VPSSNFGTQT YTCNVDHKPS NTKVDKTVER
KCCVECPPCP APGGGPSVF LFPPKPKDTL MISRTPEVTC VVVDVSHEDP
EVQFNWYVDG VEVHNAKTKP REEQFNSTFR VVSVLTVVHQ DWLNGKEYKC
KVSNKGLPAP IEKTISKTKG QPREPQVYTL PPSREEMTKN QVSLTCLVKG
FYPSDISVEW ESNGQPENNY KTTPPMLDSD GSFFLYSKLT VDKSRWQQGN
VFSCSVMHEA LHNHYTQKSL SLSPGK

SEQ ID NO: 25: IgG2 GG
ASTKGPSVFP LAPCSRSTSE STAALGCLVK DYFPEPVTVS WNSGALTSGV
HTFPAVLQSS GLYSLSSVVT VPSSNFGTQT YTCNVDHKPS NTKVDKTVER
KCCVECPPCP APGGPSVF LFPPKPKDTL MISRTPEVTC VVVDVSHEDP
EVQFNWYVDG VEVHNAKTKP REEQFNSTFR VVSVLTVVHQ DWLNGKEYKC
KVSNKGLPAP IEKTISKTKG QPREPQVYTL PPSREEMTKN QVSLTCLVKG
FYPSDISVEW ESNGQPENNY KTTPPMLDSD GSFFLYSKLT VDKSRWQQGN
VFSCSVMHEA LHNHYTQKSL SLSPGK

SEQ ID NO: 26 IgG2 G
ASTKGPSVFP LAPCSRSTSE STAALGCLVK DYFPEPVTVS WNSGALTSGV
HTFPAVLQSS GLYSLSSVVT VPSSNFGTQT YTCNVDHKPS NTKVDKTVER
KCCVECPPCP APGGPSVF LFPPKPKDTL MISRTPEVTC VVVDVSHEDP
EVQFNWYVDG VEVHNAKTKP REEQFNSTFR VVSVLTVVHQ DWLNGKEYKC
KVSNKGLPAP IEKTISKTKG QPREPQVYTL PPSREEMTKN QVSLTCLVKG
FYPSDISVEW ESNGQPENNY KTTPPMLDSD GSFFLYSKLT VDKSRWQQGN
VFSCSVMHEA LHNHYTQKSL SLSPGK

SEQ ID NO: 27 IgG2 No G
ASTKGPSVFP LAPCSRSTSE STAALGCLVK DYFPEPVTVS WNSGALTSGV
HTFPAVLQSS GLYSLSSVVT VPSSNFGTQT YTCNVDHKPS NTKVDKTVER
KCCVECPPCP APGPSVF LFPPKPKDTL MISRTPEVTC VVVDVSHEDP
EVQFNWYVDG VEVHNAKTKP REEQFNSTFR VVSVLTVVHQ DWLNGKEYKC
KVSNKGLPAPIEKTISKTKG QPREPQVYTL PPSREEMTKN QVSLTCLVKG
FYPSDISVEW ESNGQPENNY KTTPPMLDSD GSFFLYSKLT VDKSRWQQGN
VFSCSVMHEA LHNHYTQKSL SLSPGK
```

SEQUENCE LISTING

SEQ ID NO: 28: IgG2* GGG
ASTKGPSVFP LAPCSRSTSE STAALGCLVK DYFPEPVTVS WNSGALTSGV
HTFPAVLQSS GLYSLSSVVT VPSSNFGTQT YTCNVDHKPS NTKVDKTVER
KCCVECPPCP APGGGGPSVF LFPPKPKDTL MISRTPEVTC VVVDVSHEDP
EVQFNWYVDG VEVHNAKTKP REEQFNSTFR VVSVLTVVHQ DWLNGKEYKC
KVSNKGLPAPIEKTISKTKG QPREPQVYTL PPSREEMTKN QVSLTCLVKG
FYPSDISVEW ESNGQPENNY KTTPPMLDSD GSFFLYSKLT VDKSRWQQGN
VFSCSVMHEA LHNRFTQKSL SLSPGK

SEQ ID NO: 29: IgG2* GG
ASTKGPSVFP LAPCSRSTSE STAALGCLVK DYFPEPVTVS WNSGALTSGV
HTFPAVLQSS GLYSLSSVVT VPSSNFGTQT YTCNVDHKPS NTKVDKTVER
KCCVECPPCP APGGGPSVF LFPPKPKDTL MISRTPEVTC VVVDVSHEDP
EVQFNWYVDG VEVHNAKTKP REEQFNSTFR VVSVLTVVHQ DWLNGKEYKC
KVSNKGLPAPIEKTISKTKG QPREPQVYTL PPSREEMTKN QVSLTCLVKG
FYPSDISVEW ESNGQPENNY KTTPPMLDSD GSFFLYSKLT VDKSRWQQGN
VFSCSVMHEA LHNRFTQKSL SLSPGK

SEQ ID NO: 30 IgG2* G
ASTKGPSVFP LAPCSRSTSE STAALGCLVK DYFPEPVTVS WNSGALTSGV
HTFPAVLQSS GLYSLSSVVT VPSSNFGTQT YTCNVDHKPS NTKVDKTVER
KCCVECPPCP APGGPSVF LFPPKPKDTL MISRTPEVTC VVVDVSHEDP
EVQFNWYVDG VEVHNAKTKP REEQFNSTFR VVSVLTVVHQ DWLNGKEYKC
KVSNKGLPAP IEKTISKTKG QPREPQVYTL PPSREEMTKN QVSLTCLVKG
FYPSDISVEW ESNGQPENNY KTTPPMLDSD GSFFLYSKLT VDKSRWQQGN
VFSCSVMHEA LHNRFTQKSL SLSPGK

SEQ ID NO: 31 IgG2* No G
ASTKGPSVFP LAPCSRSTSE STAALGCLVK DYFPEPVTVS WNSGALTSGV
HTFPAVLQSS GLYSLSSVVT VPSSNFGTQT YTCNVDHKPS NTKVDKTVER
KCCVECPPCP APGPSVF LFPPKPKDTL MISRTPEVTC VVVDVSHEDP
EVQFNWYVDG VEVHNAKTKP REEQFNSTFR VVSVLTVVHQ DWLNGKEYKC
KVSNKGLPAP IEKTISKTKG QPREPQVYTL PPSREEMTKN QVSLTCLVKG
FYPSDISVEW ESNGQPENNY KTTPPMLDSD GSFFLYSKLT VDKSRWQQGN
VFSCSVMHEA LHNRFTQKSL SLSPGK

---

What is claimed is:

1. A monoclonal antibody comprising a heavy chain constant region that is human IgG4 isotype, wherein amino acid positions 233-236 of a hinge domain are G, G, G and unoccupied; G, G, unoccupied, and unoccupied; G, unoccupied, unoccupied, and unoccupied; or all unoccupied, with amino acid positions numbered by EU numbering.

2. The antibody of claim 1, wherein the heavy chain constant region comprises the amino acid sequence of SEQ ID NO: 5.

3. The antibody of claim 1, wherein the heavy chain constant region comprises the amino acid sequence of SEQ ID NO: 6.

4. The antibody of claim 1, wherein the heavy chain constant region comprises the amino acid sequence of SEQ ID NO: 7.

5. The antibody of claim 1, wherein the heavy chain constant region comprises the amino acid sequence of SEQ ID NO: 8.

6. The antibody of claim 1, wherein the antibody is a monospecific antibody.

7. The antibody of claim 2, wherein the antibody is a bispecific antibody comprising a first heavy chain constant region comprising SEQ ID NO: 5, and a second heavy chain constant region comprising SEQ ID NO: 9.

8. The antibody of claim 3, wherein the antibody is a bispecific antibody comprising a first heavy chain constant region comprising SEQ ID NO: 6, and a second heavy chain constant region comprising SEQ ID NO: 10.

9. The antibody of claim 4, wherein the antibody is a bispecific antibody comprising a first heavy chain constant region comprising SEQ ID NO: 7, and a second heavy chain constant region comprising SEQ ID NO: 11.

10. The antibody of claim 5, wherein the antibody is a bispecific antibody comprising a first heavy chain constant region comprising SEQ ID NO: 8, and a second heavy chain constant region comprising SEQ ID NO: 12.

11. A monoclonal antibody comprising a heavy chain constant region that is human IgG1 isotype, wherein amino acid positions 233-236 of a hinge domain are G, G, G and unoccupied; G, G, unoccupied, and unoccupied; G, unoccupied, unoccupied, and unoccupied; or all unoccupied, with amino acid positions numbered by EU numbering.

12. The antibody of claim 11, wherein the heavy chain constant region comprises the amino acid sequence of SEQ ID NO: 16.

13. The antibody of claim 11, wherein the heavy chain constant region comprises the amino acid sequence of SEQ ID NO: 17.

14. The antibody of claim 11, wherein the heavy chain constant region comprises the amino acid sequence of SEQ ID NO: 18.

15. The antibody of claim 11, wherein the heavy chain constant region comprises the amino acid sequence of SEQ ID NO: 19.

16. The antibody of claim 11, wherein the antibody is a monospecific antibody.

17. The antibody of claim 12, wherein the antibody is a bispecific antibody comprising a first heavy chain constant region comprising SEQ ID NO: 16, and a second heavy chain constant region comprising SEQ ID NO: 20.

18. The antibody of claim 13, wherein the antibody is a bispecific antibody comprising a first heavy chain constant region comprising SEQ ID NO: 17, and a second heavy chain constant region comprising SEQ ID NO: 21.

19. The antibody of claim 14, wherein the antibody is a bispecific antibody comprising a first heavy chain constant region comprising SEQ ID NO: 18, and a second heavy chain constant region comprising SEQ ID NO: 22.

20. The antibody of claim 15, wherein the antibody is a bispecific antibody comprising a first heavy chain constant region comprising SEQ ID NO: 19, and a second heavy chain constant region comprising SEQ ID NO: 23.

21. A monoclonal antibody comprising a heavy chain constant region that is human IgG2 isotype, wherein amino acid positions 233-236 of a hinge domain are G, G, G and unoccupied; G, G, unoccupied, and unoccupied; G, unoccupied, unoccupied, and unoccupied; or all unoccupied, with amino acid positions numbered by EU numbering.

22. The antibody of claim 21, wherein the heavy chain constant region comprises the amino acid sequence of SEQ ID NO: 24.

23. The antibody of claim 21, wherein the heavy chain constant region comprises the amino acid sequence of SEQ ID NO: 25.

24. The antibody of claim 21, wherein the heavy chain constant region comprises the amino acid sequence of SEQ ID NO: 26.

25. The antibody of claim 21, wherein the heavy chain constant region comprises the amino acid sequence of SEQ ID NO: 27.

26. The antibody of claim 21, wherein the antibody is a monospecific antibody.

27. The antibody of claim 22, wherein the antibody is a bispecific antibody comprising a first heavy chain constant region comprising SEQ ID NO: 24, and a second heavy chain constant region comprising SEQ ID NO: 28.

28. The antibody of claim 23, wherein the antibody is a bispecific antibody comprising a first heavy chain constant region comprising SEQ ID NO: 25, and a second heavy chain constant region comprising SEQ ID NO: 29.

29. The antibody of claim 24, wherein the antibody is a bispecific antibody comprising a first heavy chain constant region comprising SEQ ID NO: 26, and a second heavy chain constant region comprising SEQ ID NO: 30.

30. The antibody of claim 25, wherein the antibody is a bispecific antibody comprising a first heavy chain constant region comprising SEQ ID NO: 27, and a second heavy chain constant region comprising SEQ ID NO: 31.

31. An antibody drug conjugate (ADC) comprising an antibody conjugated to a cytotoxic or cytostatic agent, wherein the antibody comprises an immunoglobulin heavy chain constant region, wherein amino acid positions 233-236 of a hinge domain are G, G, G and unoccupied; G, G, unoccupied, and unoccupied; G, unoccupied, unoccupied, and unoccupied; or all unoccupied, with amino acid positions numbered by EU numbering.

32. The ADC of claim 31, wherein cytotoxic or cytostatic agent is an antitubulin agent, an auristatin, a DNA minor groove binder, a DNA replication inhibitor, an alkylating agent, a platinum complex, cis-platin, mono(platinum), bis (platinum), a tri-nuclear platinum complex, carboplatin, an anthracycline, an antibiotic, an antifolate, an antimetabolite, a chemotherapy sensitizer, a duocarmycin, a camptothecin, an etoposide, a fluorinated pyrimidine, an ionophore, a lexitropsin, a nitrosourea, a platinol, a purine antimetabolite, a puromycin, a radiation sensitizer, a steroid, a taxane, a topoisomerase inhibitor, or a vinca alkaloid.

33. A fusion protein comprising an immunoglobulin heavy chain constant region, wherein amino acid positions 233-236 of a hinge domain are G, G, G and unoccupied; G, G, unoccupied, and unoccupied; G, unoccupied, unoccupied, and unoccupied; or all unoccupied, with amino acid positions numbered by EU numbering.

34. The fusion protein of claim 33, comprising an extracellular domain of a receptor, or a ligand that binds an extracellular domain of a receptor.

35. The antibody of claim 1, wherein the heavy chain constant region comprises the amino acid sequence of SEQ ID NO: 5, SEQ ID NO: 6, SEQ ID NO: 7, or SEQ ID NO: 8, and wherein the antibody binds to FcγRI, FcγRIIA, FcγRIIB and FcγRIIIA at background levels in a surface plasmon resonance assay at 25° C.

36. The antibody of claim 11, wherein the heavy chain constant region comprises the amino acid sequence of SEQ ID NO: 16, SEQ ID NO: 17, SEQ ID NO: 18, or SEQ ID NO: 19, and wherein the antibody binds to FcγRI, FcγRIIA, FcγRIIB and FcγRIIIA at background levels in a surface plasmon resonance assay at 25° C.

37. The antibody of claim 21, wherein the heavy chain constant region comprises the amino acid sequence of SEQ ID NO: 24, SEQ ID NO: 25, SEQ ID NO: 26, or SEQ ID NO: 27, and wherein the antibody binds to FcγRI, FcγRIIA, FcγRIIB and FcγRIIIA at background levels in a surface plasmon resonance assay at 25° C.

38. The antibody of claim 35, wherein the antibody exhibits antibody-dependent cellular cytotoxicity (ADCC) activity at background levels.

39. The antibody of claim 36, wherein the antibody exhibits antibody-dependent cellular cytotoxicity (ADCC) activity at background levels.

40. The antibody of claim 37, wherein the antibody exhibits antibody-dependent cellular cytotoxicity (ADCC) activity at background levels.

* * * * *